US011858900B2

(12) United States Patent
Edwards et al.

(10) Patent No.: US 11,858,900 B2
(45) Date of Patent: Jan. 2, 2024

(54) FLUORINATED 2-AMINO-4-(SUBSTITUTED AMINO)PHENYL CARBAMATE DERIVATIVES

(71) Applicant: OcuTerra Therapeutics, Inc., Boston, MA (US)

(72) Inventors: D. Scott Edwards, Bedford, MA (US); Ben C. Askew, Marshfield, MA (US); Takeru Furuya, Cambridge, MA (US)

(73) Assignee: OcuTerra Therapeutics, Inc., Boston, MA (US)

( * ) Notice: Subject to any disclaimer, the term of this patent is extended or adjusted under 35 U.S.C. 154(b) by 0 days.

(21) Appl. No.: 17/145,453

(22) Filed: Jan. 11, 2021

(65) Prior Publication Data
US 2021/0309612 A1 Oct. 7, 2021

Related U.S. Application Data

(63) Continuation of application No. 16/888,893, filed on Jun. 1, 2020, now abandoned, which is a continuation of application No. 16/599,203, filed on Oct. 11, 2019, now abandoned, which is a continuation of application No. 15/618,937, filed on Jun. 9, 2017, now abandoned.

(60) Provisional application No. 62/348,481, filed on Jun. 10, 2016.

(51) Int. Cl.
*C07D 217/04* (2006.01)
*C07C 233/43* (2006.01)
*C07C 271/28* (2006.01)
*C07D 209/44* (2006.01)

(52) U.S. Cl.
CPC .......... *C07D 217/04* (2013.01); *C07C 233/43* (2013.01); *C07C 271/28* (2013.01); *C07D 209/44* (2013.01)

(58) Field of Classification Search
None
See application file for complete search history.

(56) References Cited

U.S. PATENT DOCUMENTS

| | | | |
|---|---|---|---|
| 5,384,330 | A | 1/1995 | Dieter et al. |
| 8,916,133 | B2 | 12/2014 | Duggan et al. |
| 9,353,048 | B2 | 5/2016 | Nan et al. |
| 9,556,114 | B2 | 1/2017 | Duggan et al. |
| 10,676,437 | B2 | 6/2020 | Furuya et al. |
| 2006/0182697 | A1 | 8/2006 | Lalleman et al. |
| 2013/0287686 | A1 | 10/2013 | Duggan et al. |
| 2014/0336252 | A1 | 11/2014 | Nan et al. |
| 2017/0081301 | A1 | 3/2017 | Nan et al. |
| 2017/0355679 | A1 | 12/2017 | Edwards et al. |

FOREIGN PATENT DOCUMENTS

| | | |
|---|---|---|
| EP | 2772481 A1 | 9/2014 |
| EP | 3138833 A1 | 3/2017 |
| WO | WO-200101970 A2 | 1/2001 |
| WO | WO-200201970 A2 | 1/2002 |
| WO | WO-2003106454 A1 | 12/2003 |
| WO | WO-2006029623 A1 | 3/2006 |
| WO | WO-2008024398 A2 | 2/2008 |
| WO | WO-2009015667 A1 | 2/2009 |
| WO | WO-2009037001 A2 | 3/2009 |
| WO | WO-2011094186 A1 | 8/2011 |
| WO | WO-2013060097 A1 | 5/2013 |
| WO | WO-2013165575 A1 | 11/2013 |
| WO | WO-2014048165 A1 | 4/2014 |
| WO | WO-2015165352 A1 | 11/2015 |
| WO | WO-2016077724 A1 | 5/2016 |
| WO | WO-2017214539 A1 | 12/2017 |

OTHER PUBLICATIONS

Chen, L., et al., "Design and Synthesis of Novel 5-Acetylthiomethyl Oxazolidinone Analogs," *Synthetic Communication*, vol. 40, No. 6, pp. 789-798 (2010).
Database Registry [Online] Service, Columbus, Ohio, US; May 19, 2015, "Aurora Fine Chemicals; propanamide, N-[3-aminio-4-(1-piperidinyl)phenyl]-", retrieved from STN Database accession No. 1707593-17-6.
Duan, H., et al. "Identification of 5-nitrofuran-2-amide derivatives that induce apoptosis in triple negative breast cancer cells by activating C/EBP-homologous protecin expression," *Bioorg. Med. Chem.*, pp. 4514-4521 (2015).
Hoestgaard-Jensen, K. et al., Pharmacological characterization of a novel positive modulator at a4B38-containing extrasynaptic GABAA receptors, *Neuropharmacology*, vol. 58, pp. 702-711 (2010).
International Search Report and Written Opinion for International Patent Application No. PCT/US2017/036802, dated Sep. 25, 2017, 14 pages.
International Search Report and Written Opinion for International Patent Application No. PCT/US2018/065325, dated Apr. 1, 2019, 14 pages.
Gurry, M., et al. "One-Pot Hydrogen Peroxide and Hydrohaic Acid Induced Ring Closure and Selective Aromatic Halogenation to Give New Ring-Fused Benzimidazoles," *Org. Letters*, vol. 17, No. 11, pp. 2856-2859 (2015).
Paget, S.D., et al., "Synthesis and antibacterial activity of pyrroloaryl-substituted oxazolidinones," *Bioorganic & Medicinal Chemistry Letters*, vol. 13, No. 23, pp. 4173-4177 (2013).

*Primary Examiner* — Po-Chih Chen
(74) *Attorney, Agent, or Firm* — Dechert LLP; Chad E. Davis

(57) ABSTRACT

The application relates to 2-amino-4-(substituted amino) phenyl carbamate derivatives, or pharmaceutically acceptable salts or solvates thereof, as KCNQ2/3 potassium channel modulators, and methods of their uses.

18 Claims, 5 Drawing Sheets

FLUORINATED 2-AMINO-4-(SUBSTITUTED AMINO)PHENYL CARBAMATE DERIVATIVES

RELATED APPLICATION

This application is a continuation of U.S. application Ser. No. 16/888,893, filed on Jun. 1, 2020, which is a continuation of U.S. application Ser. No. 16/599,203, filed on Oct. 11, 2019, which is a continuation of U.S. application Ser. No. 15/618,937, filed on Jun. 9, 2017, which claims priority to, and the benefit of, U.S. Application No. 62/348,481, filed on Jun. 10, 2016, the entire contents of each of which are incorporated herein by reference.

BACKGROUND

Epilepsy is one of the most common chronic neurological disorders, and affects approximately 50 million people worldwide. Epilepsy patients have significantly increased morbidity, including closed head injury, fractures, burns, dental injury and soft tissue injury. Decline in or worsening of memory, cognition, depression and sexual function and other lifestyle limitations occur frequently in epilepsy patients. Epilepsy patients also have an increased risk of mortality compared to the general population.

Although various pharmacologic agents are approved to treat epilepsy, many patients are not adequately treated with the currently available options. It is estimated that nearly a third of patients with epilepsy have either intractable or uncontrolled seizures or significant adverse side effects.

Ezogabine or retigabine, also known as ethyl N-[2-amino-4-[(4-fluorophenyl) methylamino]phenyl]carbamate, is an anticonvulsant used as a treatment for partial epilepsies. Ezogabine works primarily as a potassium channel opener, i.e., by activating KCNQ2/3 voltage-gated potassium channels in the brain. Ezogabine was approved by the FDA and is marketed as Potiga™ and Trobalt™. U.S. Pat. No. 5,384,330 and WO 01/01970 describe ezogabine and its use. The most common adverse events with ezogabine are central nervous system effects, particularly dizziness and somnolence. Occasional instances of urinary difficulty may require surveillance. Ezogabine is predominantly metabolized via glucuronidation, with a half-life of 8 hours.

Despite the beneficial activities of ezogabine, there is a continuing need for new compounds to treat epilepsy and other conditions ameliorated by KCNQ2/3 potassium channel opening.

SUMMARY OF THE APPLICATION

The present application provides a compound of formula A:

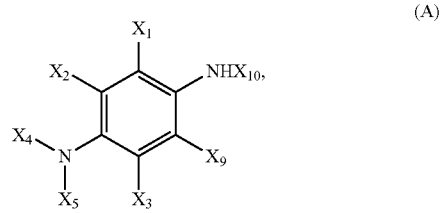

(A)

or a pharmaceutically acceptable salt or solvate thereof, wherein the compound of formula A is disclosed in detail herein below.

The application also relates to a pharmaceutical composition comprising a compound of formula A, or a pharmaceutically acceptable salt or solvate thereof, and a pharmaceutically acceptable carrier.

The application also relates to a method of modulating a KCNQ2/3 potassium channel, comprising administering to a subject in need thereof, a therapeutically effective amount of a compound of formula A, or a pharmaceutically acceptable salt or solvate thereof.

The application also relates to a compound of formula A, or a pharmaceutically acceptable salt or solvate thereof, for use in modulating a KCNQ2/3 potassium channel.

The application also relates to a compound of formula A, or a pharmaceutically acceptable salt or solvate thereof, for use in the manufacture of a medicament for modulating a KCNQ2/3 potassium channel.

The present application also relates to use of a compound of formula A, or a pharmaceutically acceptable salt or solvate thereof, in the manufacture of a medicament for modulation of a KCNQ2/3 potassium channel.

The application further relates to a method of treating or preventing a disease or disorder which can be ameliorated by KCNQ2/3 potassium channel opening, comprising administering to a subject in need thereof, a therapeutically effective amount of a compound of formula A, or a pharmaceutically acceptable salt or solvate thereof.

The application also relates to a compound of formula A, or a pharmaceutically acceptable salt or solvate thereof, for use in treating or preventing a disease or disorder which can be ameliorated by KCNQ2/3 potassium channel opening.

The application also relates to a compound of formula A, or a pharmaceutically acceptable salt or solvate thereof, for use in the manufacture of a medicament for treating or preventing a disease or disorder which can be ameliorated by KCNQ2/3 potassium channel opening.

The present application also relates to use of a compound of formula A, or a pharmaceutically acceptable salt or solvate thereof, in the manufacture of a medicament for the treatment or prevention of a disease or disorder which can be ameliorated by KCNQ2/3 potassium channel opening.

The application further relates to a method of treating or preventing epilepsy, comprising administering to a subject in need thereof, a therapeutically effective amount of a compound of formula A, or a pharmaceutically acceptable salt or solvate thereof.

The application also relates to a compound of formula A, or a pharmaceutically acceptable salt or solvate thereof, for use in treating or preventing epilepsy.

The application also relates to a compound of formula A, or a pharmaceutically acceptable salt or solvate thereof, for use in the manufacture of a medicament for treating or preventing epilepsy.

The present application also relates to the use of a compound of formula A, or a pharmaceutically acceptable salt or solvate thereof, in the manufacture of a medicament for the treatment or prevention of epilepsy.

Unless otherwise defined, all technical and scientific terms used herein have the same meaning as commonly understood by one of ordinary skill in the art to which this application belongs. In the case of conflict, the present specification, including definitions, will control. In the specification, the singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the present application. In addition, the materials, methods, and examples are illustrative only and are not intended to be limiting.

Other features and advantages of the application will be apparent from the following detailed description and claims.

DETAILED DESCRIPTION OF THE APPLICATION

Figure 1:
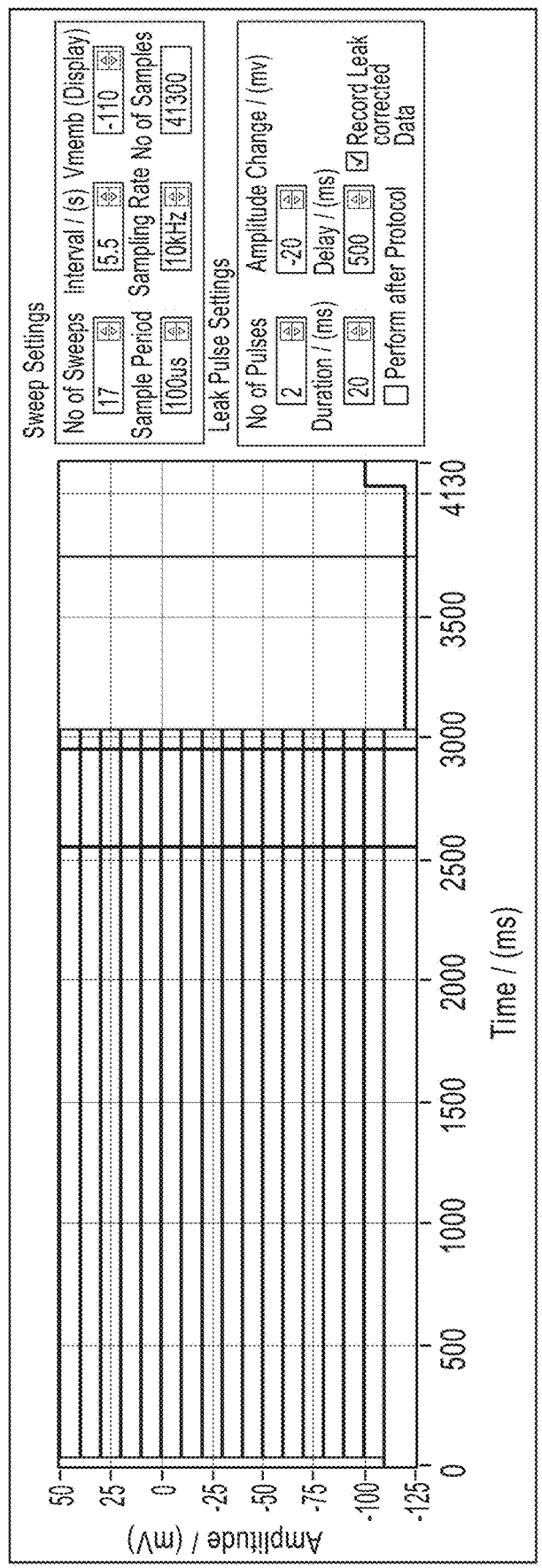
FIG. 1 is a graph showing the schematic of voltage protocol and sweep settings for SyncroPatch Recordings in the assessment of exemplified compounds of the application.
Figure 2A:
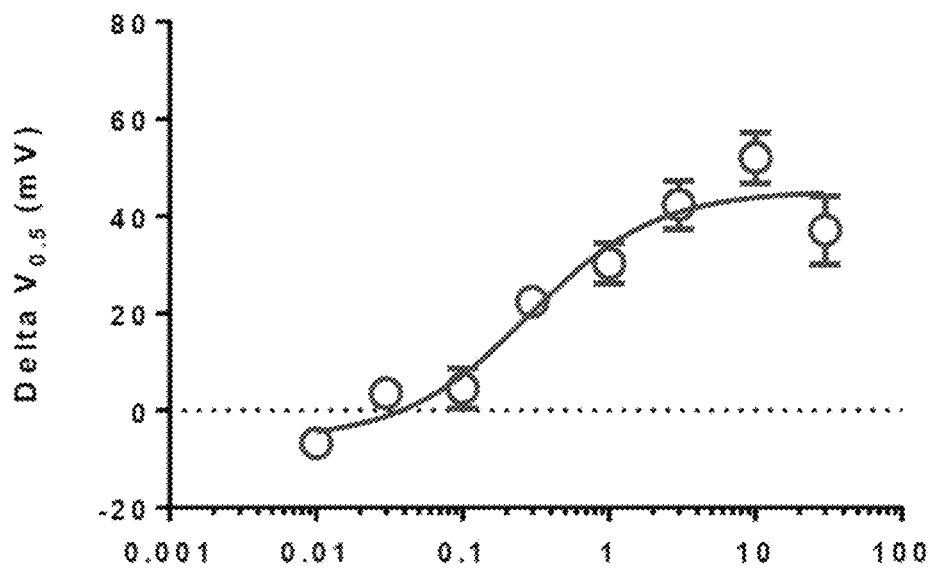
FIG. 2A is a plot showing dose-dependent activation of Kv7.2/7.3 channels by Compound 4 as measured by the SyncroPatch platform.
Figure 2B:
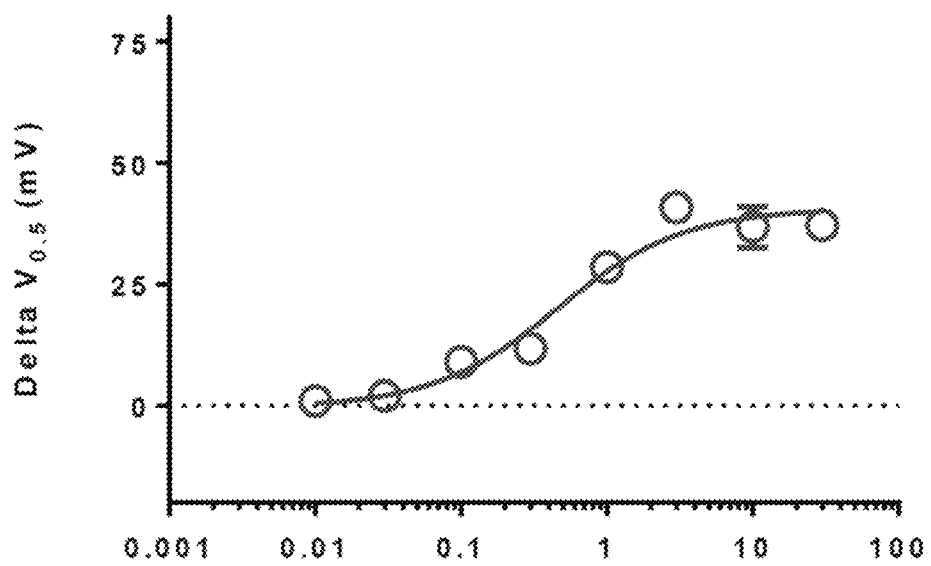
FIG. 2B is a plot showing dose-dependent activation of Kv7.2/7.3 channels by Compound 6 as measured by the SyncroPatch platform.
Figure 2C:
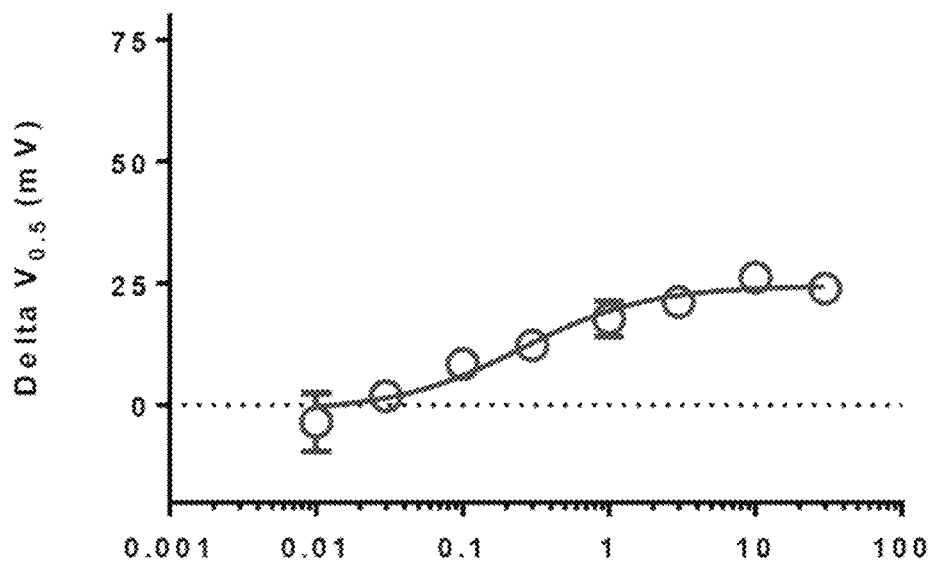
FIG. 2C is a plot showing dose-dependent activation of Kv7.2/7.3 channels by Compound 7 as measured by the SyncroPatch platform.
Figure 2D:
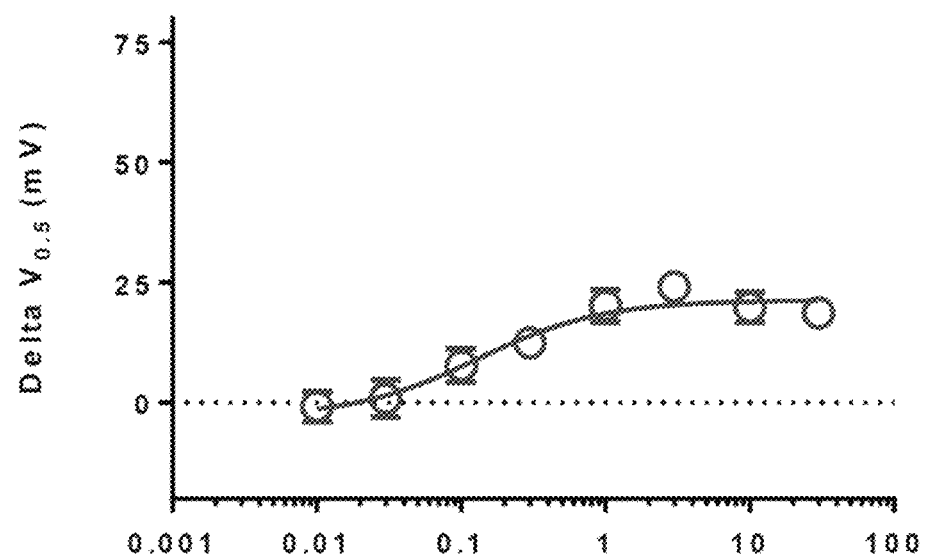
FIG. 2D is a plot showing dose-dependent activation of Kv7.2/7.3 channels by Compound 8 as measured by the SyncroPatch platform.
Figure 2E:
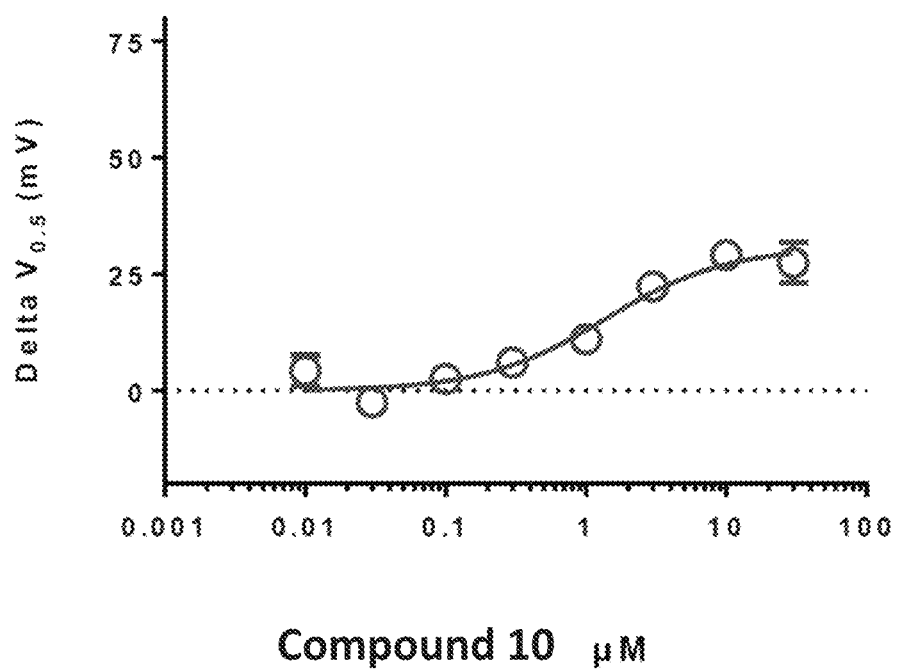
FIG. 2E is a plot showing dose-dependent activation of Kv7.2/7.3 channels by Compound 10 (control) as measured by the SyncroPatch platform.
Figure 2F:
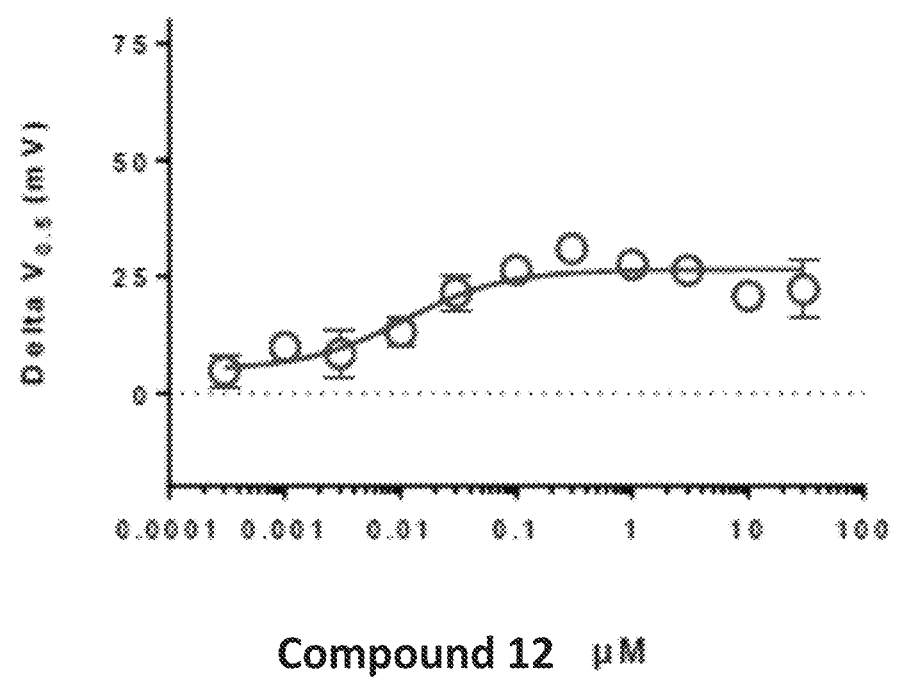
FIG. 2F is a plot showing dose-dependent activation of Kv7.2/7.3 channels by Compound 12 as measured by the SyncroPatch platform.
Figure 2G:
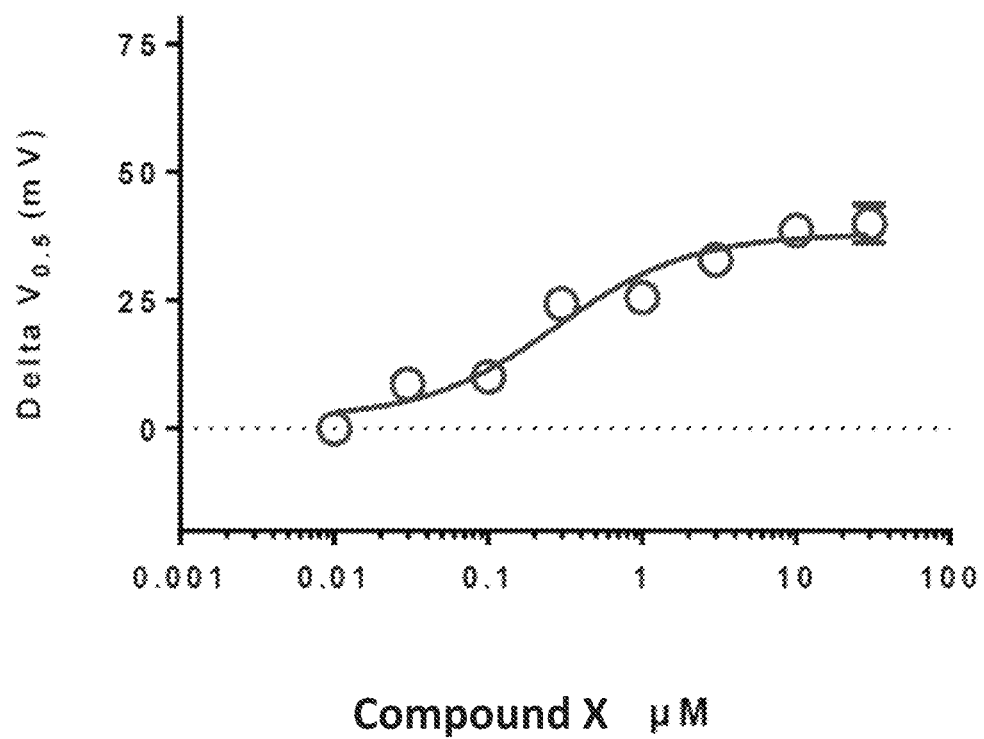
FIG. 2G is a plot showing dose-dependent activation of Kv7.2/7.3 channels by Compound X (control) as measured by the SyncroPatch platform.

For purposes of the present application, the following definitions will be used (unless expressly stated otherwise):

The term "a compound of the application" or "compounds of the application" refers to any compound disclosed herein, e.g., a compound of any of the formulae described herein, including formulae A, I, Ia, II, IIIa-IIIc, IVa-IVc, V, VI, and VII, and/or an individual compound explicitly disclosed herein. Whenever the term is used in the context of the present application it is to be understood that the reference is being made to the free base, a deuterium labeled compound, and the corresponding pharmaceutically acceptable salts or solvates thereof, provided that such is possible and/or appropriate under the circumstances.

The term "pharmaceutical" or "pharmaceutically acceptable" when used herein as an adjective, means substantially non-toxic and substantially non-deleterious to the recipient.

By "pharmaceutical formulation" it is further meant that the carrier, solvent, excipient, and salt must be compatible with the active ingredient of the formulation (e.g., a compound of the application). It is understood by those of ordinary skill in this art that the terms "pharmaceutical formulation" and "pharmaceutical composition" are generally interchangeable, and they are so used for the purposes of this application.

Some of the compounds of the present application may exist in unsolvated as well as solvated forms such as, for example, hydrates.

"Solvate" means a solvent addition form that contains either a stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate.

Hydrates are formed by the combination of one or more molecules of water with one of the substances in which the water retains its molecular state as $H_2O$, such combination being able to form one or more hydrate. In the hydrates, the water molecules are attached through secondary valencies by intermolecular forces, in particular hydrogen bridges. Solid hydrates contain water as so-called crystal water in stoichiometric ratios, where the water molecules do not have to be equivalent with respect to their binding state. Examples of hydrates are sesquihydrates, monohydrates, dihydrates or trihydrates. Equally suitable are the hydrates of salts of the compounds of the application.

Physiologically acceptable, i.e., pharmaceutically compatible or pharmaceutically acceptable, salts can be salts of the compounds of the application with inorganic or organic acids. Preference is given to salts with inorganic acids, such as, for example, hydrochloric acid, hydrobromic acid, phosphoric acid or sulphuric acid, or to salts with organic carboxylic or sulphonic acids, such as, for example, acetic acid, trifluoroacetic acid, propionic acid, maleic acid, fumaric acid, malic acid, citric acid, tartaric acid, lactic acid, benzoic acid, or methanesulphonic acid, ethanesulphonic acid, benzenesulphonic acid, toluenesulphonic acid or naphthalenedisulphonic acid. Other pharmaceutically compatible salts which may be mentioned are salts with customary bases, such as, for example, alkali metal salts (for example sodium or potassium salts), alkaline earth metal salts (for example calcium or magnesium salts) or ammonium salts, derived from ammonia or organic amines, such as, for example, diethylamine, triethylamine, ethyldiisopropylamine, procaine, dibenzylamine, N-methylmorpholine, dihydroabietylamine or methylpiperidine. Representative salts include the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamottle (embonate), palmitate, pantothenate, phosphate/diphosphate, polygalacturonate, salicylate, stearate, sulfate, subacetate, succinate, tannate, tartrate, teoclate, tosylate, triethiodide, and valerate.

The compounds of the application may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers. It is intended that all of the possible optical isomers and diastereomers in mixtures and as pure or partially purified compounds are included within the ambit of the application. The application is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

In the present specification, the structural formula of the compound represents a certain isomer for convenience in some cases, but the present application includes all isomers, such as geometrical isomers, optical isomers based on an asymmetrical carbon, stereoisomers, tautomers, and the like.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. In one example,

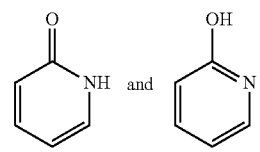 [SMILES: O=c1cccc[nH]1 ; Oc1ccccn1]

are tautomers to each other.

It is to be understood that the compounds of the present application may be depicted as different tautomers. It should also be understood that when compounds have tautomeric forms, all tautomeric forms are intended to be included in the scope of the present application, and the naming of the compounds does not exclude any tautomer form.

If desired, racemic mixtures of the compounds may be separated so that the individual enantiomers are isolated. The separation can be carried out by methods well known in the art, such as contacting a racemic mixture of compounds with an enantiomerically pure compound to form a diastereomeric mixture, followed by separation of the individual diastereomers by standard methods, such as fractional crystallization or chromatography. The diastereomeric mixture is often a mixture of diasteriomeric salts formed by contacting a racemic mixture of compounds with an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which are well known in the art.

The application also includes one or more metabolites of a compound of the application.

The present application also comprehends deuterium labeled compounds of each of the formulae described herein or the individual compounds specifically disclosed, wherein a hydrogen atom is replaced by a deuterium atom. The deuterium labeled compounds comprise a deuterium atom having an abundance of deuterium that is substantially greater than the natural abundance of deuterium, e.g., 0.015%.

The term "deuterium enrichment factor" as used herein means the ratio between the deuterium abundance and the natural abundance of a deuterium. In one aspect, a compound of the application has a deuterium enrichment factor for each deuterium atom of at least 3500 (52.5% deuterium incorporation at each deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Deuterium labeled compounds can be prepared using any of a variety of art-recognized techniques. For example, deuterium labeled compounds of each of the formulae described herein or the compounds listed in Table 1 can generally be prepared by carrying out the procedures described herein, by substituting a readily available deuterium labeled reagent for a non-deuterium labeled reagent.

A compound of the application or a pharmaceutically acceptable salt or solvate thereof that contains the aforementioned deuterium atom(s) is within the scope of the application. Further, substitution with deuterium, i.e., $^2$H, can afford certain therapeutic advantages resulting from greater metabolic stability, for example, increased in vivo half-life and/or reduced dosage requirements.

As used herein, the term "treat", "treating", or "treatment" herein, is meant decreasing the symptoms, markers, and/or any negative effects of a disease, disorder or condition in any appreciable degree in a patient who currently has the condition. The term "treat", "treating", or "treatment" includes alleviating symptoms of a disease, disorder, or condition, e.g., alleviating the symptoms of epilepsy. In some embodiments, treatment may be administered to a subject who exhibits only early signs of the condition for the purpose of decreasing the risk of developing the disease, disorder, and/or condition.

As used herein, the term "prevent", "prevention", or "preventing" refers to any method to partially or completely prevent or delay the onset of one or more symptoms or features of a disease, disorder, and/or condition. Prevention may be administered to a subject who does not exhibit signs of a disease, disorder, and/or condition.

As used herein, "subject" means a human or animal (in the case of an animal, more typically a mammal). In one embodiment, the subject is a human. In one embodiment, the subject is a male. In one embodiment, the subject is a female.

As used herein, the term a "fluorinated derivative" is a derivative compound that has the same chemical structure as the original compound, except that at least one atom is replaced with a fluorine atom or with a group of atoms containing at least one fluorine atom.

The problem to be solved by the present application is the identification of novel compounds for the treatment and/or prevention of epilepsy and/or other diseases or disorders ameliorated by KCNQ2/3 potassium channel opening. Although drugs for epilepsy and related disorders are available, these drugs are often not suitable for many patients for a variety of reasons. Many epilepsy drugs are associated with adverse effects. For example, many of the available epilepsy drugs are believed to significantly increase the risk of birth defects if taken during the first trimester of pregnancy. Other adverse side effects include urinary retention, neuro-psychiatric symptoms including hallucinations and psychosis, dizziness and somnolence, QT-prolonging effect, and increased risk of suicidal behavior and ideation. Some epilepsy drugs require administration of high doses due to extensive metabolism into inactive or less potent metabolites. The present application provides the solution of new fluorinated 2-amino-4-(benzylamino)phenylcarbamate compounds for treating epilepsy and other diseases or disorders ameliorated by KCNQ2/3 potassium channel opening. The compounds described herein have the advantage of providing improved potency, selectivity, tissue penetration, half-life, and/or metabolic stability.

Compounds of the Application

The present application relates to a compound of formula A:

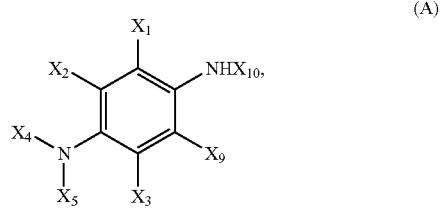

(A)

or a pharmaceutically acceptable salt or solvate thereof, wherein:

$X_1$, $X_2$, $X_3$, and $X_9$ are each independently H, deuterium, F, $NH_2$, or a $C_1$-$C_4$ alkyl optionally substituted with one or more F;

$X_{10}$ is $C(O)(C_7X_7)_nX_6$ or $CO_2(C_7X_7)_nX_6$;

$X_4$ is H, $C_1$-$C_4$ alkyl, $C_2$-$C_6$ alkenyl, or $C_2$-$C_6$ alkynyl;

$X_5$ is phenyl-$(CX_8X_8)_m$, wherein the phenyl is substituted with one or more substituents independently selected from deuterium, $C_1$-$C_4$ alkyl, $C_1$-$C_4$ alkyl substituted with one or more F, F, and $SF_5$, and wherein at least one substituent is selected from $C_1$-$C_4$ alkyl substituted with one or more F, F, and $SF_5$, or $X_4$ and $X_5$, together with the nitrogen atom to which they are attached, form a 5- to 7-membered heterocyclic ring comprising 1 or 2 heteroatoms selected from N, O, and S, wherein the heterocyclic ring is optionally substituted with one or more substituents independently selected from deuterium, $C_1$-$C_4$ alkyl, $C_1$-$C_4$ alkyl substituted with one or more F, F, and $SF_5$, wherein at least one substituent is selected from $C_1$-$C_4$ alkyl substituted with one or more F, F, and $SF_5$, or two substituents attached to adjacent carbon atoms on the heterocyclic ring, together with the carbon atoms to which they are attached, form a phenyl substituted with one or more substituents independently selected from deuterium, $C_1$-$C_4$ alkyl, $C_1$-$C_4$ alkyl substituted with one or more F, F, and $SF_5$, wherein the phenyl is substituted with at least one substituent selected from $C_1$-$C_4$ alkyl substituted with one or more F, F, and $SF_5$;

$X_6$ is H or deuterium;

each $X_7$ is independently H, $C_1$-$C_4$ alkyl, or deuterium, or two $X_7$, together with the carbon atom to which they are attached, form a 3- to 6-membered carbocyclic ring or a 3- to 6-membered heterocyclic ring comprising 1 or 2 heteroatoms selected from N, O, and S;

each $X_8$ is independently H, deuterium, $C_1$-$C_4$ alkyl, $C_1$-$C_4$ alkyl substituted with one or more F, or F;

m is 1, 2, or 3; and n is 1, 2, or 3, wherein when $X_1$, $X_2$, $X_3$, and $X_6$ are each H, n is 2, each $X_7$ is H, $X_5$ is 4-fluorobenzyl, $X_9$ is $NH_2$, and $X_{10}$ is $CO_2(C_7X_7)_nX_6$, then $X_4$ is not propenyl or propynyl.

In one embodiment, the compound of the present application is a compound of formula A, wherein when $X_1$, $X_2$, $X_3$, and $X_6$ are each H, n is 2, each $X_7$ is H, and $X_5$ is 4-fluorobenzyl, then $X_4$ is not propenyl or propynyl.

In one embodiment, the compound of the present application is a compound of formula A, wherein when $X_{10}$ is $CO_2(C_7X_7)_nX_6$, then $X_4$ is not H.

In one embodiment, the compound of formula A is of formula I:

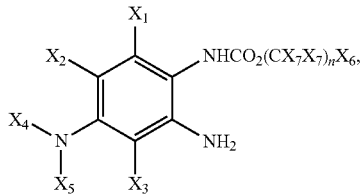

or a pharmaceutically acceptable salt or solvate thereof, wherein $X_1$, $X_2$, and $X_3$ are each independently H, deuterium, or F, and $X_4$, $X_5$, $X_6$, $X_7$, $X_8$, m, and n are each as defined above in formula A, wherein when $X_1$, $X_2$, $X_3$, and $X_6$ are each H, n is 2, each $X_7$ is H, and $X_5$ is 4-fluorobenzyl, then $X_4$ is not propenyl or propynyl.

In one embodiment, the compound of formula A is of formula Ia:

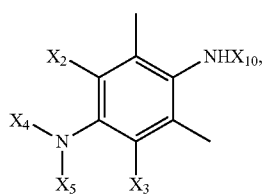

or a pharmaceutically acceptable salt or solvate thereof, wherein $X_2$, $X_3$, $X_4$, $X_5$, $X_6$, $X_7$, $X_8$, m, and n are each as defined above in formula A.

For a compound of formula A, I, or Ia, $X_1$, $X_2$, $X_3$, $X_4$, $X_5$, $X_6$, $X_7$, $X_8$, $X_9$, $X_{10}$, m, and n can each be, where applicable, selected from the groups described herein below, and any group described herein for any of $X_1$, $X_2$, $X_3$, $X_4$, $X_5$, $X_6$, $X_7$, $X_8$, $X_9$, $X_{10}$, m, and n can be combined, where applicable, with any group described herein for one or more of the remainder of $X_1$, $X_2$, $X_3$, $X_4$, $X_5$, $X_6$, $X_7$, $X_8$, $X_9$, $X_{10}$, m, and n.

In one embodiment, at least one of $X_1$, $X_2$, $X_3$, and $X_9$ is $NH_2$. In one embodiment, one of $X_1$, $X_2$, $X_3$, and $X_9$ is $NH_2$. In one embodiment, $X_9$ is $NH_2$. In one embodiment, one of $X_1$, $X_2$, $X_3$, and $X_9$ is $NH_2$, and the remainder of $X_1$, $X_2$, $X_3$, and $X_9$ are each independently H, deuterium, F, $C_1$-$C_4$ alkyl (e.g., methyl, ethyl, propyl, i-propyl, butyl, i-butyl, or t-butyl), or $C_1$-$C_4$ alkyl substituted with one or more F (e.g., methyl, ethyl, propyl, i-propyl, butyl, i-butyl, or t-butyl, each of which is substituted with one or more F). In one embodiment, $X_9$ is $NH_2$, and $X_1$, $X_2$, and $X_3$ are each independently H, deuterium, F, $C_1$-$C_4$ alkyl (e.g., methyl, ethyl, propyl, propyl, butyl, i-butyl, or t-butyl), or $C_1$-$C_4$ alkyl substituted with one or more F (e.g., methyl, ethyl, propyl, i-propyl, butyl, i-butyl, or t-butyl, each of which is substituted with one or more F). In one embodiment, $X_9$ is $NH_2$, and $X_1$, $X_2$, and $X_3$ are each independently H, deuterium, or F. In one embodiment, $X_9$ is $NH_2$, and $X_3$ is F. In one embodiment, $X_9$ is $NH_2$, $X_3$ is F, and $X_1$ and $X_2$ are each independently H or deuterium.

In one embodiment, at least one of $X_1$, $X_2$, $X_3$, and $X_9$ is $C_1$-$C_4$ alkyl (e.g., methyl, ethyl, propyl, i-propyl, butyl, i-butyl, or t-butyl) or $C_1$-$C_4$ alkyl substituted with one or more F (e.g., methyl, ethyl, propyl, i-propyl, butyl, i-butyl, or t-butyl, each of which is substituted with one or more F). In one embodiment, at least two of $X_1$, $X_2$, $X_3$, and $X_9$ is $C_1$-$C_4$ alkyl (e.g., methyl, ethyl, propyl, i-propyl, butyl, i-butyl, or t-butyl) or $C_1$-$C_4$ alkyl substituted with one or more F (e.g., methyl, ethyl, propyl, i-propyl, butyl, i-butyl, or t-butyl, each of which is substituted with one or more F). In one embodiment, $X_1$ and $X_9$ are each independently $C_1$-$C_4$ alkyl (e.g., methyl, ethyl, propyl, i-propyl, butyl, i-butyl, or t-butyl) or $C_1$-$C_4$ alkyl substituted with one or more F (e.g., methyl, ethyl, propyl, i-propyl, butyl, i-butyl, or t-butyl, each of which is substituted with one or more F), and $X_2$ and $X_3$ are each independently H, deuterium, F, or $NH_2$. In one embodiment, $X_1$ and $X_9$ are each independently $C_1$-$C_4$ alkyl (e.g., methyl, ethyl, propyl, i-propyl, butyl, i-butyl, or t-butyl) or $C_1$-$C_4$ alkyl substituted with one or more F (e.g., methyl, ethyl, propyl, i-propyl, butyl, i-butyl, or t-butyl, each of which is substituted with one or more F), and $X_2$ and $X_3$ are each independently H, deuterium, or F. In one embodiment, $X_1$ and $X_9$ are each independently methyl, $CF_3$, $CHF_2$, or $CH_2F$, and $X_2$ and $X_3$ are each independently H, deuterium, or F. In one embodiment, at least one of $X_1$ and $X_9$ is methyl. In one embodiment, $X_1$ and $X_9$ are each methyl. In one embodiment, $X_1$ and $X_9$ are each methyl, and $X_2$ and $X_3$ are each independently H, deuterium, or F.

In one embodiment, $X_{10}$ is $CO_2(C_7X_7)_nX_6$. In one embodiment, $X_{10}$ is $C(O)(C_7X_7)_nX_6$.

In one embodiment, $X_1$, $X_2$, and $X_3$ are each H.

In one embodiment, at least one of $X_1$, $X_2$, and $X_3$ is deuterium or F. In one embodiment, $X_1$ is deuterium or F, and $X_2$ and $X_3$ are each H. In one embodiment, $X_1$ is F, and $X_2$ and $X_3$ are each H. In one embodiment, $X_2$ is deuterium or F, and $X_1$ and $X_3$ are each H. In one embodiment, $X_2$ is F, and $X_1$ and $X_3$ are each H. In one embodiment, $X_3$ is deuterium or F, and $X_1$ and $X_2$ are each H. In one embodiment, $X_3$ is F, and $X_1$ and $X_2$ are each H.

In one embodiment, at least two of $X_1$, $X_2$, and $X_3$ are deuterium or F. In one embodiment, $X_1$ and $X_2$ are each independently deuterium or F, and $X_3$ is H. In one embodiment, $X_1$ and $X_2$ are each F, and $X_3$ is H. In one embodiment, $X_1$ and $X_3$ are each independently deuterium or F, and $X_2$ is H. In one embodiment, $X_1$ and $X_3$ are each F, and $X_2$ is H. In one embodiment, $X_2$ and $X_3$ are each independently deuterium or F, and $X_1$ is H. In one embodiment, $X_2$ and $X_3$ are each F, and $X_1$ is H.

In one embodiment, $X_4$ is H. In one embodiment, $X_4$ is H, only when $X_{10}$ is $C(O)(C_7X_7)_nX_6$.

In one embodiment, $X_4$ is $C_1$-$C_4$ alkyl, $C_2$-$C_6$ alkenyl, or $C_2$-$C_6$ alkynyl. In one embodiment, $X_4$ is $C_1$-$C_4$ alkyl, $C_2$-$C_6$ alkenyl, or $C_2$-$C_6$ alkynyl, when $X_{10}$ is $CO_2(C_7X_7)_nX_6$.

In one embodiment, $X_4$ is $C_1$-$C_4$ alkyl selected from methyl, ethyl, propyl, i-propyl, butyl, i-butyl, and t-butyl.

In one embodiment, $X_4$ is $C_2$-$C_6$ alkenyl or $C_2$-$C_6$ alkynyl.

In one embodiment, $X_4$ is $C_2$-$C_6$ alkenyl selected from ethenyl, propenyl (e.g., 1-propenyl or 2-propenyl), butenyl (e.g., 1-butenyl, 2-butenyl, or 3-butenyl), pentenyl (e.g., 1-pentenyl, 2-pentenyl, 3-pentenyl, or 4-pentenyl), and hexenyl (e.g., 1-hexenyl, 2-hexenyl, 3-hexenyl, 4-hexenyl, or 5-hexenyl). In one embodiment, $X_4$ is 1-propenyl or 2-propenyl.

In one embodiment, $X_4$ is $C_2$-$C_6$ alkynyl selected from ethynyl, propynyl (e.g., 1-propynyl or 2-propynyl), butynyl (e.g., 1-butynyl, 2-butynyl, or 3-butynyl), pentynyl (e.g., 1-pentynyl, 2-pentynyl, 3-pentynyl, or 4-pentynyl), and hexynyl (e.g., 1-hexynyl, 2-hexynyl, 3-hexynyl, 4-hexynyl, or 5-hexynyl). In one embodiment, $X_4$ is 1-propynyl or 2-propynyl.

In one embodiment, $X_5$ is phenyl-$(CX_8X_8)$, phenyl-$(CX_8X_8)_2$, or phenyl-$(CX_8X_8)_3$, wherein the phenyl is substituted with one or more substituents independently selected from deuterium, $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), F, and $SF_5$. In one embodiment, the phenyl is substituted with one or more substituents independently selected from $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), and F. In one embodiment, the phenyl is substituted with one or more substituents independently selected from $C_1$-$C_4$ alkyl (e.g., methyl, ethyl, propyl, i-propyl, butyl, i-butyl, or t-butyl) and $C_1$-$C_4$ alkyl substituted with one or more F (e.g., methyl, ethyl, propyl, i-propyl, butyl, i-butyl, or t-butyl, each of which is substituted with one or more F). In one embodiment, the phenyl is substituted with one or more substituents independently selected from $C_1$-$C_4$ alkyl substituted with one or more F (e.g., methyl, ethyl, propyl, i-propyl, butyl, i-butyl, or t-butyl, each of which is substituted with one or more F) and F. In one embodiment, the phenyl is substituted with one or more substituents independently selected from $CF_3$, $CHF_2$, $CH_2F$, $CH_2CF_3$, $CH_2CHF_2$, $CH_2CH_2F$, F, and $SF_5$. In one embodiment, the phenyl is substituted with one or more substituents independently selected from $CF_3$, $CHF_2$, $CH_2F$, $CH_2CF_3$, $CH_2CHF_2$, $CH_2CH_2F$, and F. In one embodiment, the phenyl is substituted with one or more groups independently selected from $CF_3$, $CHF_2$, $CH_2F$, and F. In one embodiment, the phenyl is substituted with one or more substituents independently selected from $CF_3$ and F. In one embodiment, the substituent is attached at the para-position on the phenyl ring. In one embodiment, the substituent(s) are attached at the meta-position(s) on the phenyl ring. In one embodiment, the substituent(s) are attached at the ortho-position(s) on the phenyl ring. In one embodiment, $X_5$ is 4-fluoro-benzyl, 4-trifluoromethyl-benzyl, or 3-trifluoromethyl-benzyl.

In one embodiment, each $X_5$ is H. In one embodiment, at least one $X_5$ is deuterium, $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), or F. In one embodiment, at least one $X_5$ is deuterium. In one embodiment, at least one $X_5$ is $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), or F. In one embodiment, at least one $X_5$ is $C_1$-$C_4$ alkyl (e.g., methyl, ethyl, propyl, i-propyl, butyl, i-butyl, or t-butyl) or $C_1$-$C_4$ alkyl substituted with one or more F (e.g., methyl, ethyl, propyl, i-propyl, butyl, i-butyl, or t-butyl, each of which is substituted with one or more F). In one embodiment, at least one $X_5$ is $C_1$-$C_4$ alkyl substituted with one or more F (e.g., methyl, ethyl, propyl, i-propyl, butyl, i-butyl, or t-butyl, each of which is substituted with one or more F) or F. In one embodiment, at least one $X_5$ is $C_1$-$C_4$ alkyl (e.g., methyl, ethyl, propyl, i-propyl, butyl, i-butyl, or t-butyl). In one embodiment, at least one $X_5$ is $C_1$-$C_4$ alkyl substituted with one or more F (e.g., methyl, ethyl, propyl, i-propyl, butyl, i-butyl, or t-butyl, each of which is substituted with one or more F). In one embodiment, at least one $X_5$ is F.

In one embodiment, $X_4$ and $X_5$, together with the nitrogen atom to which they are attached, form a 5- to 7-membered heterocyclic ring comprising 1 or 2 heteroatoms selected from N, O, and S (e.g., pyrrolidinyl, tetrahydrofuranyl, tetrahydrothiophenyl, oxazolidinyl, isoxazolidinyl, thiazolidinyl, isothiazolidinyl, piperidinyl, piperazinyl, tetrahydropyranyl, tetrahydrothiapyranyl, dioxanyl, morpholinyl, oxazinanyl, thiazinanyl, or oxathianyl). In one embodiment, $X_4$ and $X_5$, together with the nitrogen atom to which they are attached, form a 5- to 7-membered heterocyclic ring comprising 1 heteroatom selected from N, O, and S. In one embodiment, $X_4$ and $X_5$, together with the nitrogen atom to which they are attached, form a 5- or 6-membered heterocyclic ring comprising 1 heteroatom selected from N, O, and S. In one embodiment, $X_4$ and $X_5$, together with the nitrogen atom to which they are attached, form a 5- or 6-membered heterocyclic ring comprising 1 heteroatom selected from N and O. In one embodiment, $X_4$ and $X_5$, together with the nitrogen atom to which they are attached, form a pyrrolidinyl or piperidinyl ring.

In one embodiment, $X_4$ and $X_5$, together with the nitrogen atom to which they are attached, form a 5- to 7-membered heterocyclic ring substituted with one or more substituents independently selected from deuterium, $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), F, and $SF_5$. In one embodiment, the heterocyclic ring is substituted with one or more substituents independently selected from $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), and F. In one embodiment, the heterocyclic ring is substituted with one or more substituents independently selected from $C_1$-$C_4$ alkyl (e.g., methyl, ethyl, propyl, i-propyl, butyl, i-butyl, or t-butyl) and $C_1$-$C_4$ alkyl substituted with one or more F (e.g., methyl, ethyl, propyl, i-propyl, butyl, i-butyl, or t-butyl, each of which is substituted with one or more F). In one embodiment, the heterocyclic ring is substituted with one or more substituents independently selected from $C_1$-$C_4$ alkyl substituted with one or more F (e.g., methyl, ethyl, propyl, i-propyl, butyl, i-butyl, or t-butyl, each of which is substituted with one or more F) and F. In one embodiment, the heterocyclic ring is substituted with one or more substituents independently selected from $CF_3$, $CHF_2$, $CH_2F$, $CH_2CF_3$, $CH_2CHF_2$, $CH_2CH_2F$, F, and $SF_5$. In one embodiment, the heterocyclic ring is substituted with one or more substituents independently selected from $CF_3$, $CHF_2$, $CH_2F$, $CH_2CF_3$, $CH_2CHF_2$, $CH_2CH_2F$, and F. In one embodiment, the heterocyclic ring is substituted with one or more groups independently selected from $CF_3$, $CHF_2$, $CH_2F$, and F. In one embodiment, the heterocyclic ring is substituted with one or more substituents independently selected from $CF_3$ and F.

In one embodiment, $X_4$ and $X_5$, together with the nitrogen atom to which they are attached, form a 5- to 7-membered heterocyclic ring substituted with two or more substituents, wherein two substituents attached to adjacent carbon atoms on the heterocyclic ring, together with the carbon atoms to which they are attached, form a phenyl substituted with one or more substituents independently selected from deuterium, $C_1$-$C_4$ alkyl (e.g., methyl, ethyl, propyl, propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), F, and $SF_5$. In one embodiment, the phenyl is substituted with one or more substituents independently selected from $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), and F. In one embodiment, the phenyl is substituted with one or more substituents independently selected from $C_1$-$C_4$ alkyl (e.g., methyl, ethyl, propyl, i-propyl, butyl, i-butyl, or t-butyl) and $C_1$-$C_4$ alkyl substituted with one or more F (e.g., methyl, ethyl, propyl, i-propyl, butyl, i-butyl, or t-butyl, each of which is substituted with one or more F). In one embodiment, the phenyl is substituted with one or more substituents independently selected from $C_1$-$C_4$ alkyl substituted with one or more F (e.g., methyl, ethyl, propyl, i-propyl, butyl, i-butyl, or t-butyl, each of which is substituted with one or more F) and F. In one embodiment, the phenyl is substituted with one or more substituents independently selected from $CF_3$, $CHF_2$, $CH_2F$, $CH_2CF_3$, $CH_2CHF_2$, $CH_2CH_2F$, F, and $SF_5$. In one embodiment, the phenyl is substituted with one or more substituents independently selected from $CF_3$, $CHF_2$, $CH_2F$, $CH_2CF_3$, $CH_2CHF_2$, $CH_2CH_2F$, and F. In one embodiment, the phenyl is substituted with one or more groups independently selected from $CF_3$, $CHF_2$, $CH_2F$, and F. In one embodiment, the phenyl is substituted with one or more substituents independently selected from $CF_3$ and F.

In one embodiment, $X_4$ and $X_5$, together with the nitrogen atom to which they are attached, form a heterocyclic ring selected from

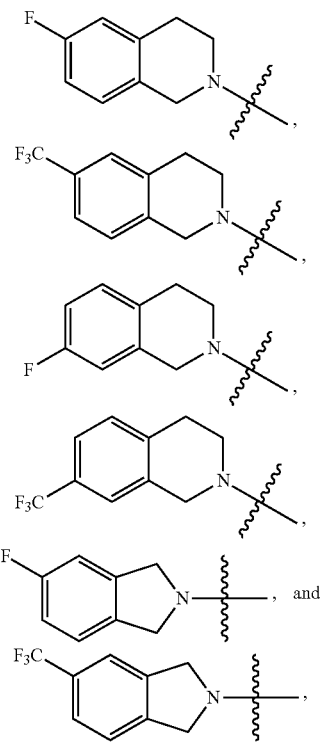

wherein the nitrogen atom is the nitrogen atom bonded to $X_4$ and $X_5$.

In one embodiment, $X_6$ is H. In one embodiment, $X_6$ is deuterium.

In one embodiment, each $X_7$ is H. In one embodiment, at least one $X_7$ is deuterium. In one embodiment, at least one $X_7$ is $C_1$-$C_4$ alkyl (e.g., methyl, ethyl, propyl, i-propyl, butyl, i-butyl, or t-butyl). In one embodiment, at least two $X_7$, together with the carbon atom to which they are attached, form a 3- to 6-membered carbocyclic ring (e.g., cyclopropyl, cyclobutyl, cyclopentyl, or cyclohexyl). In one embodiment, at least two $X_7$, together with the carbon atom to which they are attached, form a 3- to 6-membered heterocyclic ring comprising 1 or 2 heteroatoms selected from N, O, and S (e.g., aziridinyl, oxiranyl, thiiranyl, azetidinyl, oxetanyl, thietanyl, pyrrolidinyl, tetrahydrofuranyl, tetrahydrothiophenyl, oxazolidinyl, isoxazolidinyl, thiazolidinyl, isothiazolidinyl, piperidinyl, piperazinyl, tetrahydropyranyl, tetrahydrothiapyranyl, dioxanyl, morpholinyl, oxazinanyl, thiazinanyl, or oxathianyl). In one embodiment, at least two $X_7$, together with the carbon atom to which they are attached, form a 3- to 6-membered heterocyclic ring comprising 1 heteroatom selected from N, O, and S. In one embodiment, at least two $X_7$, together with the carbon atom to which they are attached, form a 3- or 4-membered heterocyclic ring comprising 1 heteroatom selected from N, O, and S. In one embodiment, at least two $X_7$, together with the carbon atom to which they are attached, form a 3- or 4-membered heterocyclic ring comprising 1 heteroatom selected from N and O.

In one embodiment, m is 1. In one embodiment, m is 2. In one embodiment, m is 3.

In one embodiment, n is 1. In one embodiment, n is 2. In one embodiment, n is 3.

Any of the substituent groups described above for any of $X_1$, $X_2$, $X_3$, $X_4$, $X_5$, $X_6$, $X_7$, $X_8$, $X_9$, $X_{10}$, m, and n can be combined with any of the substituent groups described above for one or more of the remainder of $X_1$, $X_2$, $X_3$, $X_4$, $X_5$, $X_6$, $X_7$, $X_8$, $X_9$, $X_{10}$, m, and n.

(1a) In one embodiment, $X_1$, $X_2$, and $X_3$ are each H.
(1b) In one embodiment, $X_1$ and $X_2$ are each H, and $X_3$ is deuterium or F.
(1c) In one embodiment, $X_1$ and $X_2$ are each H, and $X_3$ is F.
(1d) In one embodiment, $X_1$ and $X_9$ are each methyl, and $X_3$ is F.
(2a) In one embodiment, $X_6$ is H.
(2b) In one embodiment, $X_6$ is deuterium.
(3a) In one embodiment, each $X_7$ is H.
(3b) In one embodiment, at least one $X_7$ is $C_1$-$C_4$ alkyl.
(3c) In one embodiment, at least two $X_7$, together with the carbon atom to which they are attached, form a 3- to 6-membered carbocyclic ring or a 3- to 6-membered heterocyclic ring comprising 1 to 2 heteroatoms selected from N, O, and S. In one embodiment, at least two $X_7$, together with the carbon atom to which they are attached, form a 3- to 6-membered heterocyclic ring comprising 1 heteroatom selected from N, O, and S. In one embodiment, at least two $X_7$, together with the carbon atom to which they are attached, form a 3- or 4-membered heterocyclic ring comprising 1 heteroatom selected from N, O, and S. In one embodiment, at least two $X_7$, together with the carbon atom to which they are attached, form a 3- or 4-membered heterocyclic ring comprising 1 heteroatom selected from N and O.
(4a) In one embodiment, n is 1.
(4b) In one embodiment, n is 2.
(4c) In one embodiment, n is 3.
(A1) In one embodiment, $X_1$, $X_2$, and $X_3$ are each as defined in (1a), and $X_7$ is as defined in (3a).
(A2) In one embodiment, $X_1$, $X_2$, and $X_3$ are each as defined in (1b), and $X_7$ is as defined in (3a).

(A3) In one embodiment, $X_1$, $X_2$, and $X_3$ are each as defined in (1c), and $X_7$ is as defined in (3a).
(A4) In one embodiment, $X_1$, $X_3$, and $X_9$ are each as defined in (1d), and $X_7$ is as defined in (3a).
(B1) In one embodiment, $X_1$, $X_2$, and $X_3$ are each as defined in (1a), and $X_7$ is as defined in (3b).
(B2) In one embodiment, $X_1$, $X_2$, and $X_3$ are each as defined in (1b), and $X_7$ is as defined in (3b).
(B3) In one embodiment, $X_1$, $X_2$, and $X_3$ are each as defined in (1c), and $X_7$ is as defined in (3b).
(B4) In one embodiment, $X_1$, $X_3$, and $X_9$ are each as defined in (1d), and $X_7$ is as defined in (3b).
(C1) In one embodiment, $X_1$, $X_2$, and $X_3$ are each as defined in (1a), and $X_7$ is as defined in (3c).
(C2) In one embodiment, $X_1$, $X_2$, and $X_3$ are each as defined in (1b), and $X_7$ is as defined in (3c).
(C3) In one embodiment, $X_1$, $X_2$, and $X_3$ are each as defined in (1c), and $X_7$ is as defined in (3c).
(C4) In one embodiment, $X_1$, $X_3$, and $X_9$ are each as defined in (1d), and $X_7$ is as defined in (3c).
(D1) In one embodiment, $X_1$, $X_2$, $X_3$, $X_7$, and $X_9$ are each as defined in any one of (A1)-(A4), and $X_6$ is as defined in (2a) or (2b). In one embodiment, $X_6$ is as defined in (2a).
(D2) In one embodiment, $X_1$, $X_2$, $X_3$, $X_7$, and $X_9$ are each as defined in any one of (B1)-(B4), and $X_6$ is as defined in (2a) or (2b). In one embodiment, $X_6$ is as defined in (2a).
(D3) In one embodiment, $X_1$, $X_2$, $X_3$, $X_7$, and $X_9$ are each as defined in any one of (C1)-(C4), and $X_6$ is as defined in (2a) or (2b). In one embodiment, $X_6$ is as defined in (2a).
(E1) In one embodiment, $X_1$, $X_2$, $X_3$, $X_7$, and $X_9$ are each as defined in any one of (A1)-(A4), (B1)-(B4), or (C1)-(C4), and n is as defined in (4a).
(E2) In one embodiment, $X_1$, $X_2$, $X_3$, $X_7$, and $X_9$ are each as defined in any one of (A1)-(A4), (B1)-(B4), or (C1)-(C4), and n is as defined in (4b).
(E3) In one embodiment, $X_1$, $X_2$, $X_3$, $X_7$, and $X_9$ are each as defined in any one of (A1)-(A4), (B1)-(B4), or (C1)-(C4), and n is as defined in (4c).
(5a) In one embodiment, $X_4$ is $C_1$-$C_4$ alkyl, and $X_5$ is phenyl-$(CX_8X_8)_m$. In a further embodiment, the phenyl is substituted with one or more groups independently selected from $C_1$-$C_4$ alkyl, $C_1$-$C_4$ alkyl substituted with one or more F, F, and $SF_5$. In one embodiment, the phenyl is substituted with one or more substituents independently selected from $C_1$-$C_4$ alkyl, $C_1$-$C_4$ alkyl substituted with one or more F, and F. In one embodiment, the phenyl is substituted with one or more substituents independently selected from $C_1$-$C_4$ alkyl and $C_1$-$C_4$ alkyl substituted with one or more F. In one embodiment, the phenyl is substituted with one or more substituents independently selected from $C_1$-$C_4$ alkyl substituted with one or more F and F. In a further embodiment, the phenyl is substituted with one or more groups independently selected from $CF_3$, $CHF_2$, $CH_2F$, $CH_2CF_3$, $CH_2CHF_2$, $CH_2CH_2F$, F, and $SF_5$. In a further embodiment, the phenyl is substituted with one or more groups independently selected from $CF_3$, $CHF_2$, $CH_2F$, $CH_2CF_3$, $CH_2CHF_2$, $CH_2CH_2F$, and F. In a further embodiment, the phenyl is substituted with one or more groups independently selected from $CF_3$, $CHF_2$, $CH_2F$, and F. In a further embodiment, the phenyl is substituted with one or more groups independently selected from $CF_3$ and F.

(5b) In one embodiment, $X_4$ is $C_2$-$C_6$ alkenyl, and $X_5$ is phenyl-$(CX_8X_8)_m$. In a further embodiment, the phenyl is substituted with one or more groups independently selected from $C_1$-$C_4$ alkyl, $C_1$-$C_4$ alkyl substituted with one or more F, F, and $SF_5$. In one embodiment, the phenyl is substituted with one or more substituents independently selected from $C_1$-$C_4$ alkyl, $C_1$-$C_4$ alkyl substituted with one or more F, and F. In one embodiment, the phenyl is substituted with one or more substituents independently selected from $C_1$-$C_4$ alkyl and $C_1$-$C_4$ alkyl substituted with one or more F. In one embodiment, the phenyl is substituted with one or more substituents independently selected from $C_1$-$C_4$ alkyl substituted with one or more F and F. In a further embodiment, the phenyl is substituted with one or more groups independently selected from $CF_3$, $CHF_2$, $CH_2F$, $CH_2CF_3$, $CH_2CHF_2$, $CH_2CH_2F$, F, and $SF_5$. In a further embodiment, the phenyl is substituted with one or more groups independently selected from $CF_3$, $CHF_2$, $CH_2F$, $CH_2CF_3$, $CH_2CHF_2$, $CH_2CH_2F$, and F. In a further embodiment, the phenyl is substituted with one or more groups independently selected from $CF_3$, $CHF_2$, $CH_2F$, and F. In a further embodiment, the phenyl is substituted with one or more groups independently selected from $CF_3$ and F.

(5c) In one embodiment, $X_4$ is $C_2$-$C_6$ alkynyl, and $X_5$ is phenyl-$(CX_8X_8)_m$. In a further embodiment, the phenyl is substituted with one or more groups independently selected from $C_1$-$C_4$ alkyl, $C_1$-$C_4$ alkyl substituted with one or more F, F, and $SF_5$. In one embodiment, the phenyl is substituted with one or more substituents independently selected from $C_1$-$C_4$ alkyl, $C_1$-$C_4$ alkyl substituted with one or more F, and F. In one embodiment, the phenyl is substituted with one or more substituents independently selected from $C_1$-$C_4$ alkyl and $C_1$-$C_4$ alkyl substituted with one or more F. In one embodiment, the phenyl is substituted with one or more substituents independently selected from $C_1$-$C_4$ alkyl substituted with one or more F and F. In a further embodiment, the phenyl is substituted with one or more groups independently selected from $CF_3$, $CHF_2$, $CH_2F$, $CH_2CF_3$, $CH_2CHF_2$, $CH_2CH_2F$, F, and $SF_5$. In a further embodiment, the phenyl is substituted with one or more groups independently selected from $CF_3$, $CHF_2$, $CH_2F$, $CH_2CF_3$, $CH_2CHF_2$, $CH_2CH_2F$, and F. In a further embodiment, the phenyl is substituted with one or more groups independently selected from $CF_3$, $CHF_2$, $CH_2F$, and F. In a further embodiment, the phenyl is substituted with one or more groups independently selected from $CF_3$ and F.

(5d) In one embodiment, $X_4$ and $X_5$, together with the nitrogen atom to which they are attached, form a 5- to 7-membered heterocyclic ring comprising 1 to 2 heteroatoms selected from N, O, and S, optionally substituted with one or more substituents independently selected from $C_1$-$C_4$ alkyl, $C_1$-$C_4$ alkyl substituted with one or more F, F, and $SF_5$. In one embodiment, the heterocyclic ring is optionally substituted with one or more substituents independently selected from $C_1$-$C_4$ alkyl, $C_1$-$C_4$ alkyl substituted with one or more F, and F. In one embodiment, the heterocyclic ring is optionally substituted with one or more substituents independently selected from $C_1$-$C_4$ alkyl and $C_1$-$C_4$ alkyl substituted with one or more F. In one embodiment, the heterocyclic ring is optionally substituted with one or more substituents independently selected from $C_1$-$C_4$ alkyl substituted with one or more F and F. In one embodiment, the heterocyclic ring is optionally substituted with one or more substituents independently selected from $CF_3$, $CHF_2$, $CH_2F$, $CH_2CF_3$, $CH_2CHF_2$, $CH_2CH_2F$, F, and $SF_5$. In one embodiment, the heterocyclic ring is optionally substituted with one or more substituents independently selected from $CF_3$, $CHF_2$, $CH_2F$, $CH_2CF_3$, $CH_2CHF_2$, $CH_2CH_2F$, and F. In one embodiment, the heterocyclic ring is optionally substituted with one or more groups independently selected from $CF_3$, $CHF_2$, $CH_2F$, and F. In one embodiment, the heterocyclic ring is optionally substituted with one or more substituents independently selected from $CF_3$ and F.

(5e) In one embodiment, $X_4$ and $X_5$, together with the nitrogen atom to which they are attached, form a 5- to 7-membered heterocyclic ring comprising 1 to 2 heteroatoms selected from N, O, and S, substituted with two or more substituents, wherein two substituents attached to adjacent carbon atoms on the heterocyclic ring, together with the carbon atoms to which they are attached, form a phenyl substituted with one or more substituents independently selected from $C_1$-$C_4$ alkyl, $C_1$-$C_4$ alkyl substituted with one or more F, F, and $SF_5$. In one embodiment, the phenyl is substituted with one or more substituents independently selected from $C_1$-$C_4$ alkyl, $C_1$-$C_4$ alkyl substituted with one or more F, and F. In one embodiment, the phenyl is substituted with one or more substituents independently selected from $C_1$-$C_4$ alkyl and $C_1$-$C_4$ alkyl substituted with one or more F. In one embodiment, the phenyl is substituted with one or more substituents independently selected from $C_1$-$C_4$ alkyl substituted with one or more F and F. In a further embodiment, the phenyl is substituted with one or more groups independently selected from $CF_3$, $CHF_2$, $CH_2F$, $CH_2CF_3$, $CH_2CHF_2$, $CH_2CH_2F$, F, and $SF_5$. In a further embodiment, the phenyl is substituted with one or more groups independently selected from $CF_3$, $CHF_2$, $CH_2F$, $CH_2CF_3$, $CH_2CHF_2$, $CH_2CH_2F$, and F. In a further embodiment, the phenyl is substituted with one or more groups independently selected from $CF_3$, $CHF_2$, $CH_2F$, and F. In one embodiment, the phenyl is substituted with one or more substituents independently selected from $CF_3$ and F.

(6a) In one embodiment, m is 1.
(6b) In one embodiment, m is 2.
(6c) In one embodiment, m is 3.
(7a) In one embodiment, each $X_5$ is H.
(7b) In one embodiment, at least one $X_5$ is deuterium.
(7c) In one embodiment, at least one $X_5$ is $C_1$-$C_4$ alkyl, $C_1$-$C_4$ alkyl substituted with one or more F, or F.
(F1a) In one embodiment, $X_4$ and $X_5$ are each as defined in (5a), and m is as defined in any one of (6a)-(6c). In a further embodiment, m is as defined in (6a).
(F1b) In one embodiment, $X_4$ and $X_5$ are each as defined in (5b), and m is as defined in any one of (6a)-(6c). In a further embodiment, m is as defined in (6a).
(F1c) In one embodiment, $X_4$ and $X_5$ are each as defined in (5c), and m is as defined in any one of (6a)-(6c). In a further embodiment, m is as defined in (6a).
(G1a) In one embodiment, $X_4$, $X_5$, and m are each as defined in any one of (F1a)-(F1c), and $X_5$ is as defined in (7a).
(G1b) In one embodiment, $X_4$, $X_5$, and m are each as defined in any one of (F1a)-(F1c), and $X_5$ is as defined in (7b).
(G1c) In one embodiment, $X_4$, $X_5$, and m are each as defined in any one of (F1a)-(F1c), and $X_5$ is as defined in (7c).
(H1a) In one embodiment, $X_4$ and $X_5$ are each as defined in any one of (5a)-(5e), and $X_1$, $X_2$, and $X_3$ are each as defined in (1a).
(H1b) In one embodiment, $X_4$ and $X_5$ are each as defined in any one of (5a)-(5e), and $X_1$, $X_2$, and $X_3$ are each as defined in (1b).
(H1c) In one embodiment, $X_4$ and $X_5$ are each as defined in any one of (5a)-(5e), and $X_1$, $X_2$, and $X_3$ are each as defined in (1c).
(H1d) In one embodiment, $X_4$ and $X_5$ are each as defined in any one of (5a)-(5e), and $X_1$, $X_3$, and $X_9$ are each as defined in (1d).
(H1e) In one embodiment, $X_4$ and $X_5$ are each as defined in any one of (5a)-(5e), and $X_7$ is as defined in (3a).
(H1f) In one embodiment, $X_4$ and $X_5$ are each as defined in any one of (5a)-(5e), and $X_7$ is as defined in (3b).
(H1g) In one embodiment, $X_4$ and $X_5$ are each as defined in any one of (5a)-(5e), and $X_7$ is as defined in (3c).
(H1h) In one embodiment, $X_4$ and $X_5$ are each as defined in any one of (5a)-(5e), and $X_1$, $X_2$, $X_3$, and $X_7$ are each as defined in (A1).
(H1i) In one embodiment, $X_4$ and $X_5$ are each as defined in any one of (5a)-(5e), and $X_1$, $X_2$, $X_3$, and $X_7$ are each as defined (A2).
(H1j) In one embodiment, $X_4$ and $X_5$ are each as defined in any one of (5a)-(5e), and $X_1$, $X_2$, $X_3$, and $X_7$ are each as defined (A3).
(H1k) In one embodiment, $X_4$ and $X_5$ are each as defined in any one of (5a)-(5e), and $X_1$, $X_3$, $X_7$, and $X_9$ are each as defined (A4).
(H1l) In one embodiment, $X_4$ and $X_5$ are each as defined in any one of (5a)-(5e), and $X_1$, $X_2$, $X_3$, and $X_7$ are each as defined (B1).
(H1m) In one embodiment, $X_4$ and $X_5$ are each as defined in any one of (5a)-(5e), and $X_1$, $X_2$, $X_3$, and $X_7$ are each as defined (B2).
(H1n) In one embodiment, $X_4$ and $X_5$ are each as defined in any one of (5a)-(5e), and $X_1$, $X_2$, $X_3$, and $X_7$ are each as defined (B3).
(H1o) In one embodiment, $X_4$ and $X_5$ are each as defined in any one of (5a)-(5e), and $X_1$, $X_3$, $X_7$, and $X_9$ are each as defined (B4).
(H1p) In one embodiment, $X_4$ and $X_5$ are each as defined in any one of (5a)-(5e), and $X_1$, $X_2$, $X_3$, and $X_7$ are each as defined (C1).
(H1q) In one embodiment, $X_4$ and $X_5$ are each as defined in any one of (5a)-(5e), and $X_1$, $X_2$, $X_3$, and $X_7$ are each as defined (C2).
(H1r) In one embodiment, $X_4$ and $X_5$ are each as defined in any one of (5a)-(5e), and $X_1$, $X_2$, $X_3$, and $X_7$ are each as defined (C3).
(H1s) In one embodiment, $X_4$ and $X_5$ are each as defined in any one of (5a)-(5e), and $X_1$, $X_3$, $X_7$, and $X_9$ are each as defined (C4).
(H1t) In one embodiment, $X_4$ and $X_5$ are each as defined in any one of (5a)-(5e), and $X_1$, $X_2$, $X_3$, $X_6$, $X_7$, and $X_9$ are each as defined (D1).
(H1u) In one embodiment, $X_4$ and $X_5$ are each as defined in any one of (5a)-(5e), and $X_1$, $X_2$, $X_3$, $X_6$, $X_7$, and $X_9$ are each as defined (D2).
(H1v) In one embodiment, $X_4$ and $X_5$ are each as defined in any one of (5a)-(5e), and $X_1$, $X_2$, $X_3$, $X_6$, $X_7$, and $X_9$ are each as defined (D3).

(H1w) In one embodiment, $X_4$ and $X_5$ are each as defined in any one of (5a)-(5e), and $X_1$, $X_2$, $X_3$, $X_7$, $X_9$, and n are each as defined (E1).

(H1x) In one embodiment, $X_4$ and $X_5$ are each as defined in any one of (5a)-(5e), and $X_1$, $X_2$, $X_3$, $X_7$, $X_9$, and n are each as defined (E2).

(H1y) In one embodiment, $X_4$ and $X_5$ are each as defined in any one of (5a)-(5e), and $X_1$, $X_2$, $X_3$, $X_7$, $X_9$, and n are each as defined (E3).

(I1a) In one embodiment, $X_1$, $X_2$, and $X_3$ are each as defined in (1a), and $X_4$, $X_5$, and m are each as defined in any one of (F1a)-(F1c).

(I1b) In one embodiment, $X_1$, $X_2$, and $X_3$ are each as defined in (1b), and $X_4$, $X_5$, and m are each as defined in any one of (F1a)-(F1c).

(I1c) In one embodiment, $X_1$, $X_2$, and $X_3$ are each as defined in (1c), and $X_4$, $X_5$, and m are each as defined in any one of (F1a)-(F1c).

(I1d) In one embodiment, $X_1$, $X_3$, and $X_9$ are each as defined in (1d), and $X_4$, $X_5$, and m are each as defined in any one of (F1a)-(F1c).

(I1e) In one embodiment, $X_1$, $X_2$, and $X_3$ are each as defined in (1a), and $X_4$, $X_5$, $X_8$, and m are each as defined in any one of (G1a)-(G1c).

(I1f) In one embodiment, $X_1$, $X_2$, and $X_3$ are each as defined in (1b), and $X_4$, $X_5$, $X_8$, and m are each as defined in any one of (G1a)-(G1c).

(I1g) In one embodiment, $X_1$, $X_2$, and $X_3$ are each as defined in (1c), and $X_4$, $X_5$, $X_8$, and m are each as defined in any one of (G1a)-(G1c).

(I1h) In one embodiment, $X_1$, $X_3$, and $X_9$ are each as defined in (1d), and $X_4$, $X_5$, $X_8$, and m are each as defined in any one of (G1a)-(G1c).

(I1i) In one embodiment, $X_1$, $X_2$, $X_3$, and $X_7$ are each as defined (A1), and $X_4$, $X_5$, and m are each as defined in any one of (F1a)-(F1c).

(I1j) In one embodiment, $X_1$, $X_2$, $X_3$, and $X_7$ are each as defined (A2), and $X_4$, $X_5$, and m are each as defined in any one of (F1a)-(F1c).

(I1k) In one embodiment, $X_1$, $X_2$, $X_3$, and $X_7$ are each as defined (A3), and $X_4$, $X_5$, and m are each as defined in any one of (F1a)-(F1c).

(I1l) In one embodiment, $X_1$, $X_3$, $X_7$, and $X_9$ are each as defined (A4), and $X_4$, $X_5$, and m are each as defined in any one of (F1a)-(F1c).

(I1m) In one embodiment, $X_1$, $X_2$, $X_3$, and $X_7$ are each as defined (B1), and $X_4$, $X_5$, and m are each as defined in any one of (F1a)-(F1c).

(I1n) In one embodiment, $X_1$, $X_2$, $X_3$, and $X_7$ are each as defined (B2), and $X_4$, $X_5$, and m are each as defined in any one of (F1a)-(F1c).

(I1o) In one embodiment, $X_1$, $X_2$, $X_3$, and $X_7$ are each as defined (B3), and $X_4$, $X_5$, and m are each as defined in any one of (F1a)-(F1c).

(I1p) In one embodiment, $X_1$, $X_3$, $X_7$, and $X_9$ are each as defined (B4), and $X_4$, $X_5$, and m are each as defined in any one of (F1a)-(F1c).

(I1q) In one embodiment, $X_1$, $X_2$, $X_3$, and $X_7$ are each as defined (C1), and $X_4$, $X_5$, and m are each as defined in any one of (F1a)-(F1c).

(I1r) In one embodiment, $X_1$, $X_2$, $X_3$, and $X_7$ are each as defined (C2), and $X_4$, $X_5$, and m are each as defined in any one of (F1a)-(F1c).

(I1s) In one embodiment, $X_1$, $X_2$, $X_3$, and $X_7$ are each as defined (C3), and $X_4$, $X_5$, and m are each as defined in any one of (F1a)-(F1c).

(I1t) In one embodiment, $X_1$, $X_3$, $X_7$, and $X_9$ are each as defined (C4), and $X_4$, $X_5$, and m are each as defined in any one of (F1a)-(F1c).

(I1u) In one embodiment, $X_1$, $X_2$, $X_3$, $X_6$, $X_7$, and $X_9$ are each as defined (D1), and $X_4$, $X_5$, and m are each as defined in any one of (F1a)-(F1c).

(I1v) In one embodiment, $X_1$, $X_2$, $X_3$, $X_6$, $X_7$, and $X_9$ are each as defined (D2), and $X_4$, $X_5$, and m are each as defined in any one of (F1a)-(F1c).

(I1w) In one embodiment, $X_1$, $X_2$, $X_3$, $X_6$, $X_7$, and $X_9$ are each as defined (D3), and $X_4$, $X_5$, and m are each as defined in any one of (F1a)-(F1c).

(I1x) In one embodiment, $X_1$, $X_2$, $X_3$, $X_7$, $X_9$, and n are each as defined (E1), and $X_4$, $X_5$, and m are each as defined in any one of (F1a)-(F1c).

(I1y) In one embodiment, $X_1$, $X_2$, $X_3$, $X_7$, $X_9$, and n are each as defined (E2), and $X_4$, $X_5$, and m are each as defined in any one of (F1a)-(F1c).

(I1z) In one embodiment, $X_1$, $X_2$, $X_3$, $X_7$, $X_9$, and n are each as defined (E3), and $X_4$, $X_5$, and m are each as defined in any one of (F1a)-(F1c).

(J1) In one embodiment, $X_1$, $X_2$, $X_3$, $X_4$, $X_5$, $X_6$, $X_7$, $X_8$, $X_9$, m, and n are each, where applicable, as defined in any one of (1a)-(I1z), $X_{10}$ is $C(O)(C_7X_7)_nX_6$.

(J2) In one embodiment, $X_1$, $X_2$, $X_3$, $X_4$, $X_5$, $X_6$, $X_7$, $X_8$, $X_9$, m, and n are each, where applicable, as defined in any one of (1a)-(I1z), $X_{10}$ is $CO_2(C_7X_7)_nX_6$.

In one embodiment, the compound of formula A is of formula II or VI:

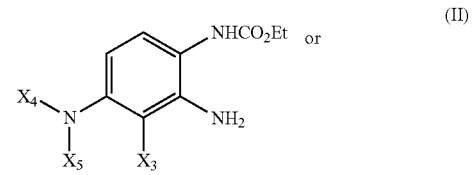

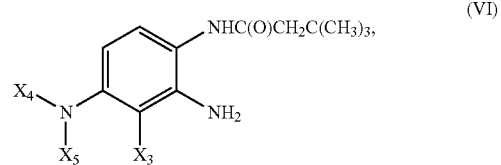

or a pharmaceutically acceptable salt or solvate thereof, wherein $X_3$, $X_4$, $X_5$, $X_8$, and m are each as defined above in formula A.

$X_3$, $X_4$, $X_5$, $X_8$, and m can each be selected from any of the substituents described above in formula A, and any of the substituents described above for any of $X_3$, $X_4$, $X_5$, $X_8$, and m can be combined with any of the substituents described above for one or more of the remainder of $X_3$, $X_4$, $X_5$, $X_8$, and m.

In one embodiment, the compound of formula A is of formula V or VII:

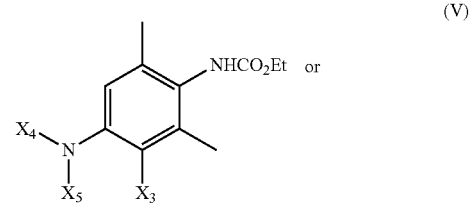

-continued

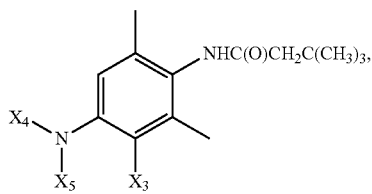
(VII)

or a pharmaceutically acceptable salt or solvate thereof, wherein $X_3$, $X_4$, $X_5$, $X_8$, and m are each as defined above in formula A.

$X_3$, $X_4$, $X_5$, $X_8$, and m can each be selected from any of the substituents described above in formula A, and any of the substituents described above for any of $X_3$, $X_4$, $X_5$, $X_8$, and m can be combined with any of the substituents described above for one or more of the remainder of $X_3$, $X_4$, $X_5$, $X_8$, and m.

In one embodiment, the compound of formula A is of formula IIIa:

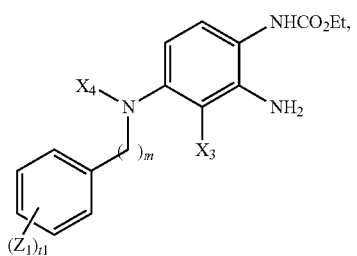
(IIIa)

or a pharmaceutically acceptable salt or solvate thereof, wherein:

$X_3$, $X_4$, and m are each as defined above in formula A;

t1 is 1, 2, 3, 4, or 5; and each $Z_1$ is independently $C_1$-$C_4$ alkyl, $C_1$-$C_4$ alkyl substituted with one or more F, F, or $SF_5$, wherein at least one $Z_1$ is $C_1$-$C_4$ alkyl substituted with one or more F, F, or $SF_5$, wherein when $X_3$ is H, t1 is 1, and $Z_1$ is 4-fluoro, then $X_4$ is not propenyl or propynyl.

In one embodiment, the compound of formula A is of formula IIIb or IIIc:

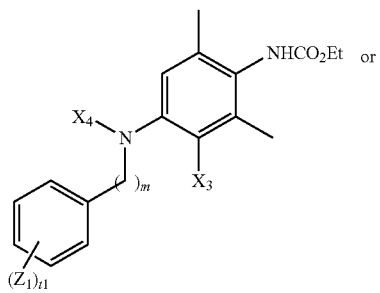
(IIIb)

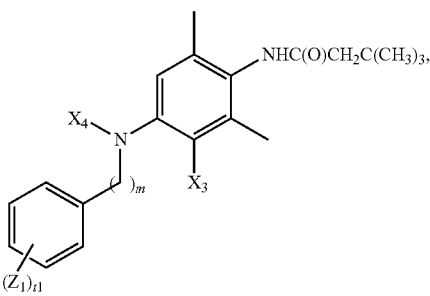
(IIIc)

or a pharmaceutically acceptable salt or solvate thereof, wherein:

$X_3$, $X_4$, and m are each as defined above in formula A;

t1 is 1, 2, 3, 4, or 5; and each $Z_1$ is independently $C_1$-$C_4$ alkyl, $C_1$-$C_4$ alkyl substituted with one or more F, F, or $SF_5$, wherein at least one $Z_1$ is $C_1$-$C_4$ alkyl substituted with one or more F, F, or $SF_5$.

For a compound of formula IIIa, IIIb, or IIIc, t1 and $Z_1$ can each be, where applicable, selected from the groups described herein below, and any group described herein for any of t1 and $Z_1$ can be combined, where applicable, with any group described herein for the remainder of t1 and $Z_1$.

In one embodiment, t1 is 1, 2, or 3.

In one embodiment, t1 is 1 or 2.

In one embodiment, t1 is 1.

In one embodiment, t1 is 2.

In one embodiment, t1 is 3.

In one embodiment, t1 is 4.

In one embodiment, t1 is 5.

In one embodiment, at least one $Z_1$ is $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), F, or $SF_5$.

In one embodiment, at least one $Z_1$ is $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), or F.

In one embodiment, at least one $Z_1$ is $C_1$-$C_4$ alkyl (e.g., methyl, ethyl, propyl, i-propyl, butyl, i-butyl, or t-butyl) or $C_1$-$C_4$ alkyl substituted with one or more F (e.g., methyl, ethyl, propyl, i-propyl, butyl, i-butyl, or t-butyl, each of which is substituted with one or more F).

In one embodiment, at least one $Z_1$ is $C_1$-$C_4$ alkyl substituted with one or more F (e.g., methyl, ethyl, propyl, i-propyl, butyl, i-butyl, or t-butyl, each of which is substituted with one or more F) or F.

In one embodiment, at least one $Z_1$ is $CF_3$, $CHF_2$, $CH_2F$, $CH_2CF_3$, $CH_2CHF_2$, $CH_2CH_2F$, F, or $SF_5$. In a further embodiment, at least one $Z_1$ is $CF_3$, $CHF_2$, $CH_2F$, $CH_2CF_3$, $CH_2CHF_2$, $CH_2CH_2F$, or F. In a further embodiment, at least one $Z_1$ is $CF_3$, $CHF_2$, $CH_2F$, or F. In a further embodiment, at least one $Z_1$ is $CF_3$ or F.

$X_3$, $X_4$, and m can each be selected from any of the substituents described above in formula A, and any of the substituents described above for any of $X_3$, $X_4$, and m can be combined with any of the substituents described above for one or more of the remainder of $X_3$, $X_4$, and m, and can further be combined with any of the substituents described for any of t1 and $Z_1$.

In one embodiment, t1 is 1, and $Z_1$ is $CF_3$ or F.

In one embodiment, t1 is 1, $Z_1$ is $CF_3$ or F, and m is 1.

In one embodiment, t1 is 1, $Z_1$ is $CF_3$ or F, and $X_4$ is propenyl or propynyl.

In one embodiment, t1 is 1, $Z_1$ is $CF_3$ or F, m is 1, and $X_4$ is propenyl or propynyl.

In one embodiment, t1 is 1, $Z_1$ is $CF_3$ or F, $X_4$ is propenyl or propynyl, and $X_3$ is H or F.

In one embodiment, t1 is 1, $Z_1$ is $CF_3$, m is 1, $X_4$ is propenyl or propynyl, and $X_3$ is H or F.

In one embodiment, t1 is 1, $Z_1$ is $CF_3$ or F, m is 1, $X_4$ is propenyl or propynyl, and $X_3$ is F.

In one embodiment, the compound of formula A is of formula IVa, IVb, or IVc:

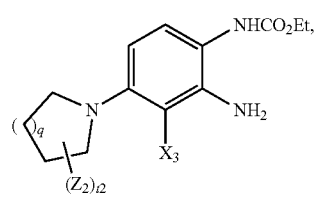

(IVa)

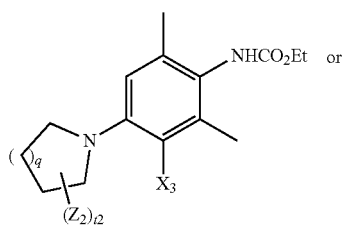

(IVb)

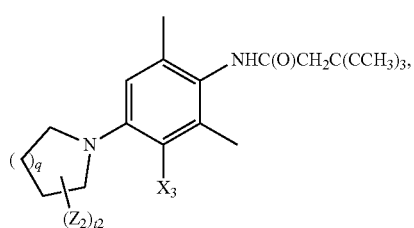

(IVc)

or a pharmaceutically acceptable salt or solvate thereof, wherein:

$X_3$ is as defined above in formula A;

q is 1, 2, or 3;

t2 is 1, 2, 3, or 4; and each $Z_2$ is independently $C_1$-$C_4$ alkyl, $C_1$-$C_4$ alkyl substituted with one or more F, F, or $SF_5$, wherein at least one $Z_2$ is $C_1$-$C_4$ alkyl substituted with one or more F, F, or $SF_5$, or two $Z_2$, together with adjacent carbon atoms to which they are attached, form a phenyl substituted with one or more substituents independently selected from $C_1$-$C_4$ alkyl, $C_1$-$C_4$ alkyl substituted with one or more F, F, and $SF_5$, wherein the phenyl is substituted with at least one substituent selected from $C_1$-$C_4$ alkyl substituted with one or more F, F, and $SF_5$.

For a compound of formula IVa, IVb, or IVc, q, t2, and $Z_2$ can each be, where applicable, selected from the groups described herein below, and any group described herein for any of q, t2, and $Z_2$ can be combined, where applicable, with any group described herein for one or more of the remainder of q, t2, and $Z_2$.

In one embodiment, q is 1.
In one embodiment, q is 2.
In one embodiment, q is 3.
In one embodiment, t2 is 1, 2, or 3.
In one embodiment, t2 is 1 or 2.
In one embodiment, t2 is 1.
In one embodiment, t2 is 2.
In one embodiment, t2 is 3.
In one embodiment, t2 is 4.

In one embodiment, at least one $Z_2$ is $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), F, or $SF_5$.

In one embodiment, at least one $Z_2$ is $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), or F.

In one embodiment, at least one $Z_2$ is $C_1$-$C_4$ alkyl (e.g., methyl, ethyl, propyl, i-propyl, butyl, i-butyl, or t-butyl) or $C_1$-$C_4$ alkyl substituted with one or more F (e.g., methyl, ethyl, propyl, i-propyl, butyl, i-butyl, or t-butyl, each of which is substituted with one or more F).

In one embodiment, at least one $Z_2$ is $C_1$-$C_4$ alkyl substituted with one or more F (e.g., methyl, ethyl, propyl, i-propyl, butyl, i-butyl, or t-butyl, each of which is substituted with one or more F) or F.

In one embodiment, at least one $Z_2$ is $CF_3$, $CHF_2$, $CH_2F$, $CH_2CF_3$, $CH_2CHF_2$, $CH_2CH_2F$, F, or $SF_5$. In a further embodiment, at least one $Z_2$ is $CF_3$, $CHF_2$, $CH_2F$, $CH_2CF_3$, $CH_2CHF_2$, $CH_2CH_2F$, or F. In a further embodiment, at least one $Z_2$ is $CF_3$, $CHF_2$, $CH_2F$, or F. In a further embodiment, at least one $Z_2$ is $CF_3$ or F.

In one embodiment, two $Z_2$, together with adjacent carbon atoms to which they are attached, form a phenyl substituted with one or more substituents independently selected from $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), F, and $SF_5$. In one embodiment, the phenyl is substituted with one or more substituents independently selected from $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), and F. In one embodiment, the phenyl is substituted with one or more substituents independently selected from $C_1$-$C_4$ alkyl (e.g., methyl, ethyl, propyl, i-propyl, butyl, i-butyl, or t-butyl) and $C_1$-$C_4$ alkyl substituted with one or more F (e.g., methyl, ethyl, propyl, i-propyl, butyl, i-butyl, or t-butyl, each of which is substituted with one or more F). In one embodiment, the phenyl is substituted with one or more substituents independently selected from $C_1$-$C_4$ alkyl substituted with one or more F (e.g., methyl, ethyl, propyl, i-propyl, butyl, i-butyl, or t-butyl, each of which is substituted with one or more F) and F. In one embodiment, the phenyl is substituted with one or more substituents independently selected from $CF_3$, $CHF_2$, $CH_2F$, $CH_2CF_3$, $CH_2CHF_2$, $CH_2CH_2F$, F, and $SF_5$. In one embodiment, the phenyl is substituted with one or more substituents independently selected from $CF_3$, $CHF_2$, $CH_2F$, $CH_2CF_3$, $CH_2CHF_2$, $CH_2CH_2F$, and F. In one embodiment, the phenyl is substituted with one or more groups independently selected from $CF_3$, $CHF_2$, $CH_2F$, and F. In one embodiment, the phenyl is substituted with one or more substituents independently selected from $CF_3$ and F.

Any of the substituents described above for any of q, t2, and $Z_2$ can be combined with any of the substituents described above for any of the remainder of q, t2, and $Z_2$, and can further be combined with any of the substituents described above for $X_3$.

In one embodiment, a compound of the present application is selected from the compounds in Tables 1a and 1b.

TABLE 1a

| Cpmd No. | Structure |
|---|---|
| 1 | *(chemical structure: ethyl carbamate-NH-phenyl with NH2, F, and N-allyl-N-(4-fluorobenzyl) substituents)* |
| 2 | *(chemical structure: ethyl carbamate-NH-phenyl with NH2, F, and N-allyl-N-(4-trifluoromethylbenzyl) substituents)* |
| 3 | *(chemical structure: ethyl carbamate-NH-phenyl with NH2, F, and N-allyl-N-(3-trifluoromethylbenzyl) substituents)* |
| 4 | *(chemical structure: ethyl carbamate-NH-phenyl with NH2, and N-allyl-N-(4-fluorobenzyl) substituents)* |

TABLE 1a-continued

| Cpmd No. | Structure |
|---|---|
| 5 | *(chemical structure: ethyl carbamate-NH-phenyl with NH2, and N-allyl-N-(4-trifluoromethylbenzyl) substituents)* |
| 6 | *(chemical structure: ethyl carbamate-NH-phenyl with NH2, and N-allyl-N-(3-trifluoromethylbenzyl) substituents)* |
| 7 | *(chemical structure: ethyl carbamate-NH-phenyl with NH2, F, and N-propargyl-N-(4-fluorobenzyl) substituents)* |
| 8 | *(chemical structure: ethyl carbamate-NH-phenyl with NH2, F, and N-propargyl-N-(4-trifluoromethylbenzyl) substituents)* |

TABLE 1a-continued

| Cpmd No. | Structure |
|---|---|
| 9 | *ethyl (2-amino-4-(N-(3-(trifluoromethyl)benzyl)-N-(prop-2-yn-1-yl)amino)-3-fluorophenyl)carbamate* |
| 11 | *ethyl (2-amino-4-(N-(4-(trifluoromethyl)benzyl)-N-(prop-2-yn-1-yl)amino)phenyl)carbamate* |
| 12 | *ethyl (2-amino-4-(N-(3-(trifluoromethyl)benzyl)-N-(prop-2-yn-1-yl)amino)phenyl)carbamate* |
| 13 | *ethyl (2-amino-3-fluoro-4-(5-fluoroisoindolin-2-yl)phenyl)carbamate* |
| 14 | *ethyl (2-amino-3-fluoro-4-(5-(trifluoromethyl)isoindolin-2-yl)phenyl)carbamate* |
| 15 | *ethyl (2-amino-4-(5-fluoroisoindolin-2-yl)phenyl)carbamate* |
| 16 | *ethyl (2-amino-4-(5-(trifluoromethyl)isoindolin-2-yl)phenyl)carbamate* |
| 17 | *ethyl (2-amino-3-fluoro-4-(6-fluoro-3,4-dihydroisoquinolin-2(1H)-yl)phenyl)carbamate* |
| 18 | *ethyl (2-amino-3-fluoro-4-(7-(trifluoromethyl)-3,4-dihydroisoquinolin-2(1H)-yl)phenyl)carbamate* |
| 19 | *ethyl (2-amino-3-fluoro-4-(6-(trifluoromethyl)-3,4-dihydroisoquinolin-2(1H)-yl)phenyl)carbamate* |
| 20 | *ethyl (2-amino-3-fluoro-4-(7-fluoro-3,4-dihydroisoquinolin-2(1H)-yl)phenyl)carbamate* |

TABLE 1a-continued

| Cpmd No. | Structure |
|---|---|
| 21 | 4-(6-fluoro-3,4-dihydroisoquinolin-2(1H)-yl)-2-amino-phenyl ethylcarbamate |
| 22 | 4-(7-(trifluoromethyl)-3,4-dihydroisoquinolin-2(1H)-yl)-2-amino-phenyl ethylcarbamate |
| 23 | 4-(6-(trifluoromethyl)-3,4-dihydroisoquinolin-2(1H)-yl)-2-amino-phenyl ethylcarbamate |
| 24 | 4-(7-fluoro-3,4-dihydroisoquinolin-2(1H)-yl)-2-amino-phenyl ethylcarbamate |
| 25 | 4-(6-fluoro-3,4-dihydroisoquinolin-2(1H)-yl)-3-fluoro-2,6-dimethylphenyl ethylcarbamate |
| 26 | 4-((4-fluorobenzyl)(prop-2-yn-1-yl)amino)-3-fluoro-2,6-dimethylphenyl ethylcarbamate |

TABLE 1b

| Cpmd No. | Structure |
|---|---|
| 27 | N-(4-(6-fluoro-3,4-dihydroisoquinolin-2(1H)-yl)-3-fluoro-2,6-dimethylphenyl)-3,3-dimethylbutanamide |
| 28 | N-(4-((4-fluorobenzyl)(prop-2-yn-1-yl)amino)-3-fluoro-2,6-dimethylphenyl)-3,3-dimethylbutanamide |
| 29 | N-(4-((4-fluorobenzyl)amino)-3-fluoro-2-aminophenyl)-3,3-dimethylbutanamide |
| 30 | N-(4-((4-fluorobenzyl)(prop-2-yn-1-yl)amino)-3-fluoro-2-aminophenyl)-3,3-dimethylbutanamide |
| 31 | N-(4-((4-(trifluoromethyl)benzyl)(prop-2-yn-1-yl)amino)-3-fluoro-2-aminophenyl)-3,3-dimethylbutanamide |
| 32 | N-(4-(6-fluoro-3,4-dihydroisoquinolin-2(1H)-yl)-3-fluoro-2-aminophenyl)-3,3-dimethylbutanamide |

TABLE 1b-continued

| Cpmd No. | Structure |
|---|---|
| 33 | ![Structure 33] |
| 34 | ![Structure 34] |
| 35 | ![Structure 35] |
| 36 | ![Structure 36] |

In one embodiment, a compound of the application is a pharmaceutically acceptable salt. In one embodiment, a compound of the application is a solvate. In one embodiment, a compound of the application is a hydrate.

The present application relates to pharmaceutical compositions comprising one of the compounds of the application as an active ingredient. In one embodiment, the application provides a pharmaceutical composition comprising at least one compound of formula A, I, Ia, II, IIIa, IIIb, IIIc, IVa, IVb, IVc, V, VI, or VII, or a pharmaceutically acceptable salt or solvate thereof, and one or more pharmaceutically acceptable carrier or excipient. In one embodiment, the application provides a pharmaceutical composition comprising at least one compound of Table 1, or a pharmaceutically acceptable salt or solvate thereof, and one or more pharmaceutically acceptable carrier or excipient.

The present application relates to a method of synthesizing a compound of the application or a pharmaceutically acceptable salt or solvate thereof. A compound of the application can be synthesized using a variety of methods known in the art, such as those described in U.S. Pat. No. 8,916,133, the contents of which are incorporated by reference in their entirety. The schemes and description below depict general routes for the preparation of a compound of the application. For example, compounds of the present application can be synthesized by following the steps outlined in Schemes 1-6 which comprise different sequences of assembling intermediates 3a, 3b, 3c, 3d, 3e, 4a, 4b, 4c, 5a, 5b, 5c, 5d, 5e, 7a, 7b, 7c, 7d, 7e, 7f, 8a, 8b, 8c, 8d, 8e, 8f, 9a, 9b, 9c, 9d, 9e, and 9f. Starting materials are either commercially available or made by known procedures in the reported literature or as illustrated.

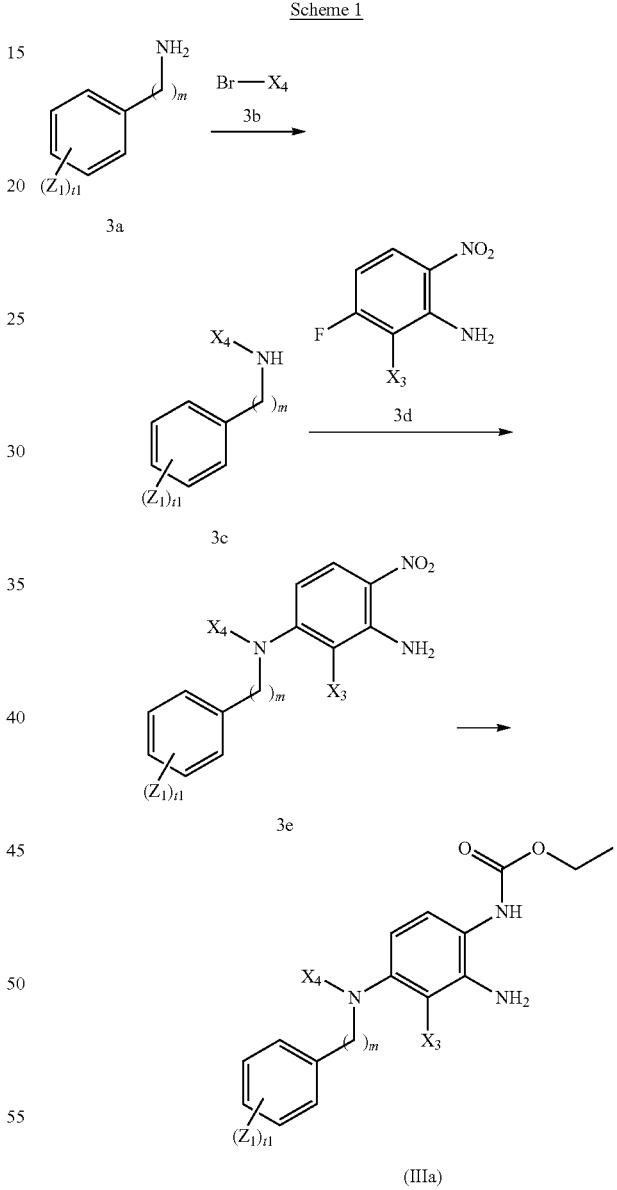

Scheme 1 wherein $X_3$, $X_4$, $Z_1$, t1, and m are as defined herein above.

The general way of preparing representative compounds of the present application using intermediates 3a, 3b, 3c, 3d, and 3e is outlined in Scheme 1. Alkylation of amine 3a with bromide 3b (i.e., an alkyl bromide, allyl bromide, etc.) in the presence of a base, e.g., diisopropylethylamine (DIPEA), in a solvent, e.g., dimethylformamide (DMF), and optionally at an elevated temperature provides intermediate 3c. Nucleophilic addition of 3c to fluoride 3d in the presence of a base, e.g., triethylamine (Et₃N), in a solvent, e.g., dimethylsulfoxide (DMSO), and optionally at an elevated temperature provides intermediate 3e. Reduction of 3e using a metal catalyst, e.g., Zinc (Zn), and ammonium chloride (NH₄Cl) in the presence of a base, e.g., DIPEA and in a solvent, e.g., methanol (MeOH), and consequent esterification with an agent, e.g., ethyl chloroformate, in the presence of a base, e.g., diisopropylethylamine (DIPEA), and optionally at an elevated temperature provides compounds of formula IIIa.

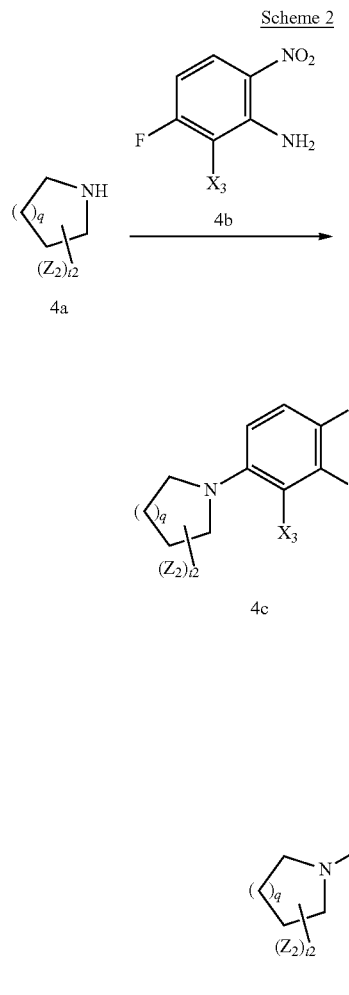

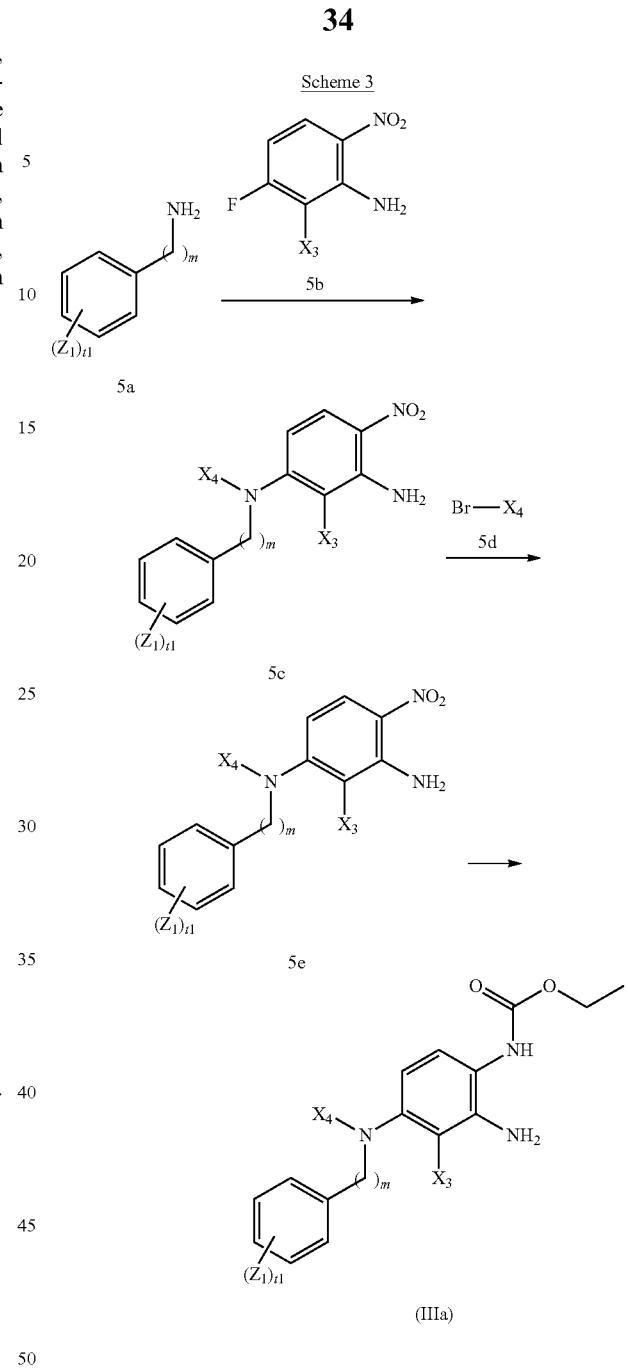

wherein $X_3$, $Z_2$, and t2 are as defined herein above.

The general way of preparing representative compounds of the present application using intermediates 4a, 4b, and 4c is outlined in Scheme 2. Nucleophilic addition of 4a to fluoride 4b in the presence of a base, e.g., triethylamine (Et₃N), in a solvent, e.g., dimethylsulfoxide (DMSO), and optionally at an elevated temperature provides intermediate 4c. Reduction of 4c using a metal catalyst, e.g., Zinc (Zn), and ammonium chloride (NH₄Cl) in the presence of a base, i.e., DIPEA and in a solvent, i.e., methanol (MeOH), and consequent esterification with an agent, e.g., ethyl chloroformate, in the presence of a base, e.g., diisopropylethylamine (DIPEA), and optionally at an elevated temperature provides compounds of formula IVa.

wherein $X_3$, $X_4$, $Z_1$, t1, and m are as defined herein above.

The general way of preparing representative compounds of the present application using intermediates 5a, 5b, 5c, 5d, and 5e is outlined in Scheme 3. Nucleophilic addition of 5a to fluoride 5b in the presence of a base, e.g., triethylamine (Et₃N), in a solvent, e.g., dimethylsulfoxide (DMSO), and optionally at an elevated temperature provides intermediate 5c. Alkylation of amine 5c with bromide 5d (i.e., an alkyl bromide, allyl bromide, etc.) in the presence of a base, e.g., diisopropylethylamine (DIPEA), in a solvent, e.g., dimethylformamide (DMF), and optionally at an elevated temperature provides intermediate 5e. Reduction of 5e using a metal catalyst, e.g., Zinc (Zn), and ammonium chloride (NH₄Cl) in the presence of a base, e.g., DIPEA and in a solvent, e.g., water, and consequent esterification with an agent, e.g., ethyl chloroformate, in the presence of a base, e.g., diisopropylethylamine (DIPEA), and optionally at an elevated temperature provides compounds of formula IIIa.

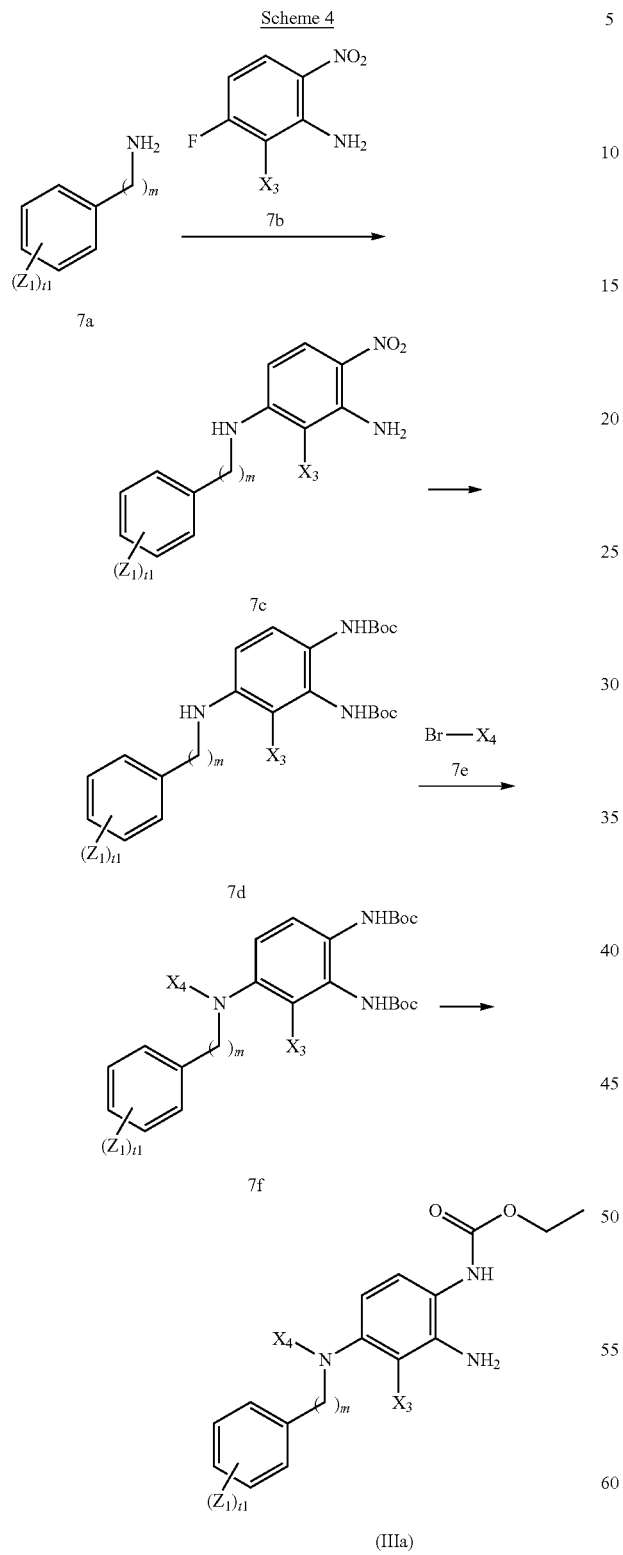

7e, and 7f is outlined in Scheme 5. Nucleophilic addition of 7a to fluoride 7b in the presence of a base, e.g., triethylamine (Et$_3$N), in a solvent, e.g., dimethylsulfoxide (DMSO), and optionally at an elevated temperature provides intermediate 7c. Reduction of 7c using a metal catalyst, e.g., Zinc (Zn), and ammonium chloride (NH$_4$Cl) in the presence of a base, e.g., DIPEA and in a solvent, e.g., methanol (MeOH), and consequent protection using BOC$_2$O in the presence of a base, e.g., NaHCO$_3$, provides intermediate 7d. Alkylation of amine 7d with bromide 7e (i.e., an alkyl bromide, allyl bromide, etc.) in the presence of a base, e.g., diisopropylethylamine (DIPEA), in a solvent, e.g., dimethylformamide (DMF), and optionally at an elevated temperature provides intermediate 7f. Deprotection of 7f in the presence of an acid, e.g., trifluoroacetic acid (TFA), and optionally at an elevated temperature, and consequent esterification with an agent, e.g., ethyl chloroformate, in the presence of a base, e.g., diisopropylethylamine (DIPEA), and optionally at an elevated temperature provides compounds of formula IIIa.

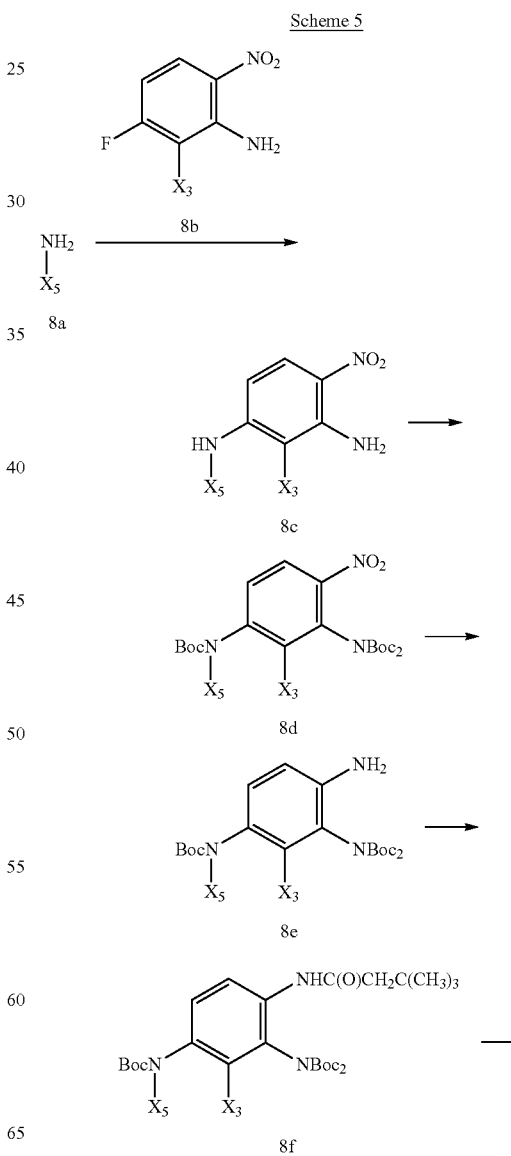

wherein $X_3$, $X_4$, $Z_1$, t1, and m are as defined herein above.

The general way of preparing representative compounds of the present application using intermediates 7a, 7b, 7c, 7d,

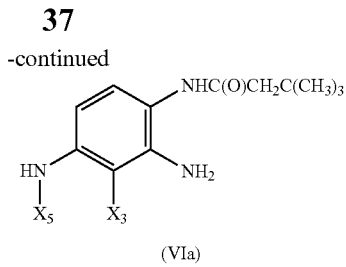

(VIa)

wherein $X_3$ and $X_5$ are as defined herein above.

The general way of preparing representative compounds of the present using intermediates 8a, 8b, 8c, 8d, 8e, 8f, and 8g is outlined in Scheme 6. Nucleophilic addition of 8a to fluoride 8b in the presence of a base, e.g., triethylamine ($Et_3N$), in a solvent, e.g., dimethylsulfoxide (DMSO), and optionally at an elevated temperature provides intermediate 8c. Protection of 8c with $Boc_2O$ in the presence of a base, e.g., sodium hydride (NaH) and/or 4-dimethylaminopyridine (DMAP), in a solvent, e.g., tetrahydrofuran (THF), and optionally at an elevated temperature provides intermediate 8d. Reduction of 8d using a metal catalyst, e.g., Zinc (Zn), and ammonium chloride ($NH_4Cl$), in a solvent, e.g., methanol (MeOH), and optionally at an elevated temperature provides intermediate 8e. Acetylation of 8e with tert-butylacetyl chloride in the presence of a base, e.g., diisopropylethylamine (DIPEA), in a solvent, e.g., dichlorimethane (DCM), and optionally at an elevated temperature provides intermediate 8f. Deprotection of 7f in the presence of an acid, e.g., hydrochloric acid (HCL), in a solvent, e.g., DCM and/or diethyl ether ($Et_2O$), and optionally at an elevated temperature provides compounds of formula VIa.

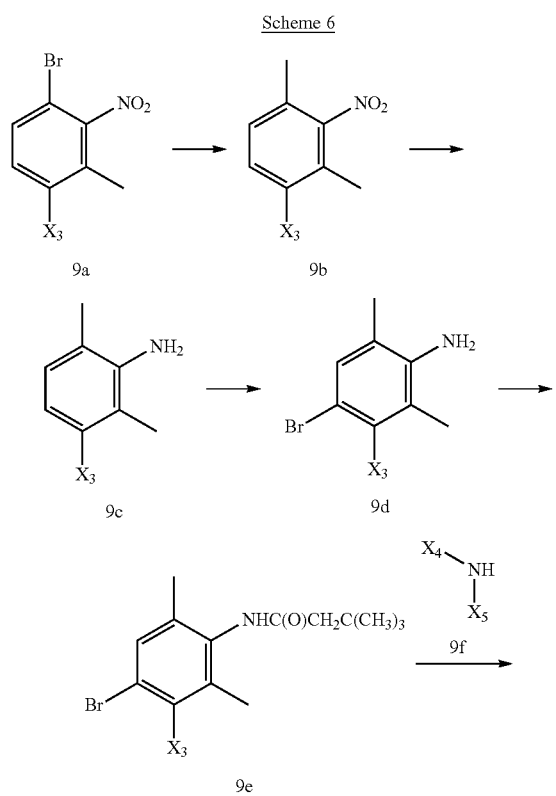

Scheme 6

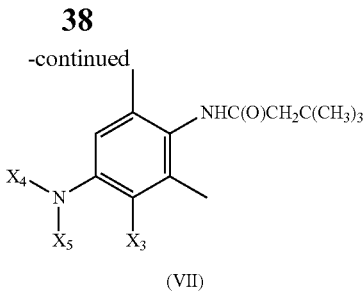

(VII)

wherein $X_3$, $X_4$, and $X_5$ are as defined herein above.

The general way of preparing representative compounds of the present application using intermediates 9a, 9b, 9c, 9d, 9e, 9f is outlined in Scheme 7. Methylation of 9a with trimethylboroxine in the presence of a metal catalyst, e.g., tetrakis(triphenylphosphine)palladium ($Pd(PPh_3)_4$)), and a base, e.g., potassium carbonate ($K_2CO_3$), in a solvent, e.g., dimethylsulfoxide (DMSO), and optionally at an elevated temperature provides intermediate 9b. Reduction of 9b using a metal catalyst, e.g., Zinc (Zn), and ammonium chloride ($NH_4Cl$), in a solvent, e.g., water and ethyl acetate (EtOAc), and optionally at an elevated temperature provides intermediate 9c. Bromination of 9c with N-bromosuccinimide (NBS), in the presence of an acid, e.g., acetic acid, and optionally at an elevated temperature provides intermediate 9d. Acetylation of 9d with tert-butylacetyl chloride in the presence of a base, e.g., diisopropylethylamine (DIPEA), in a solvent, e.g., acetonitrile (MeCN), and optionally at an elevated temperature provides intermediate 9e. Coupling 9e with 9f in the presence of a metal catalyst, e.g., tris(dibenzylideneacetone)dipalladium ($Pd_2(dba)_3$), and in the presence of a base, e.g., potassium tert-butoxide (t-BuOK), in a solvent, e.g., toluene, and optionally at an elevated temperature provides compounds of formula VII.

The present application also comprehends deuterium labeled compounds, wherein one or more hydrogen atoms is replaced by a deuterium atom having an abundance of deuterium at that position that is substantially greater than the natural abundance of deuterium, which is 0.015%.

Deuterium labeled compounds can be prepared by using any of a variety of art-recognized techniques. For example, deuterium labeled compounds of any of the formulae described herein and compounds listed in Table 1 of this application can be prepared.

In one aspect, a deuterium labeled compound of the application is a pharmaceutically acceptable salt. In one aspect, a deuterium labeled compound of the application is a solvate. In one aspect, a deuterium labeled compound of the application is a hydrate.

The present application relates to pharmaceutical compositions comprising one of the deuterium labeled compounds of the application as an active ingredient. In one aspect, the application provides a pharmaceutical composition comprising at least one deuterium labeled compound of any of the formulae described herein or a pharmaceutically acceptable salt or solvate thereof and one or more pharmaceutically acceptable carrier or excipient.

The present application relates to a method of synthesizing a deuterium labeled compound of the application or a pharmaceutically acceptable salt or solvate thereof. The deuterium labeled compounds of the application can be prepared using any of a variety of art-recognized techniques, such as those described in U.S. Pat. No. 8,916,133, the contents of which are incorporated by reference in their entirety. For example, a deuterium labeled compound can be prepared by starting with deuterium labeled Compound 1 and/or substituting a readily available deuterium labeled reagent for a non-deuterium labeled reagent.

The scheme and description below depicts a general route for the incorporation of deuterium label to produce a deuterium labeled compound of the application.

Scheme 1A

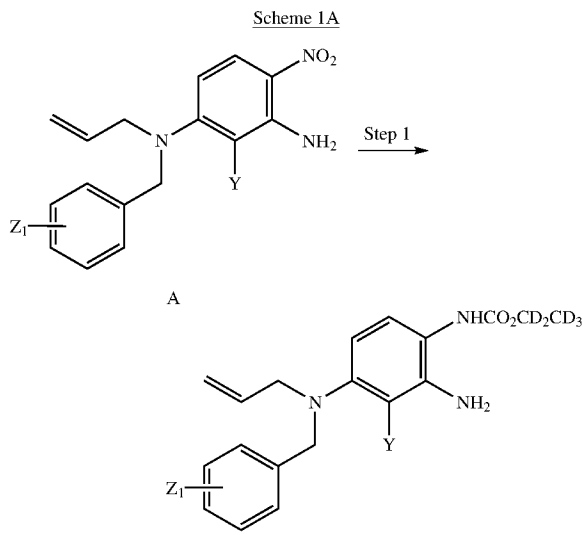

Scheme 1A outlines a preparation for a deuterium labeled compound of the application. The preparation begins with Compound A (from Scheme 1A described herein). In Step 1, the nitro group of Compound A is reduced and then the deuterium label is introduced via formation of a carbamate containing one or more deuterium. For example, the nitro group of Compound A can be reduced using zinc powder and ammonium chloride in methanol and the carbamate can be formed using ethyl-$d_5$ chloroformate to provide a deuterium labeled compound.

In some embodiments, temporary protecting groups may be used to prevent other reactive functionality, such as amines, thiols, alcohols, phenols, and carboxylic acids, from participating or interfering in the fluorination reaction. Representative amine protecting groups include, for example, tert-butoxycarbonyl and trityl (removed under acid conditions), Fmoc (removed by the use of secondary amines such as piperidine), and benzyloxycarbonyl (removed by strong acid or by catalytic hydrogenolysis). The trityl group may also be used for the protection of thiols, phenols, and alcohols. In certain embodiments the carboxylic acid protecting groups include, for example, tert-butyl ester (removed by mild acid), benzyl ester (usually removed by catalytic hydrogenolysis), and alkyl esters such as methyl or ethyl (usually removed by mild base). All protecting groups may be removed at the conclusion of the synthesis using the conditions described above for the individual protecting groups, and the final product may be purified by techniques which would be readily apparent to one of ordinary skill in the art, in combination with the teachings described herein.

Biological Assays

Assessment of KCNQ2/3 Channel Activation Activity

Biological activities of the compounds of the application can be assessed by using various methods known in the art. For example, the KCNQ2/3 channel activation activity of the compounds of the application can be evaluated through an in vitro assay described below.

The in vitro effects of a compound of the application on cloned KCNQ2/3 potassium channels (e.g., encoded by the human KCNQ2/3 gene) are evaluated using a patch clamp system. Compounds of the application are tested at various concentrations (e.g., 0.01, 0.1, 1, 10 and 100 µM) for a certain duration of exposure (e.g., 5 min). The baseline for each recording is established. A single test compound concentration is applied for a certain duration of exposure after the vehicle. Each recording ends with treatment with a supramaximal dose of linopirdine. The % activation is calculated using the following equation by using leak subtracted responses:

$$\frac{\text{vehicle\_response} - \text{compound\_response}}{\text{vehicle\_response} - \text{flupirtine\_response}}$$

Maximal Electroshock Seizure Test (MES)

In MES test, the ability of different doses of the test compound in preventing seizure induced by an electrical stimulus, delivered through the corneal electrodes primed with a drop of anesthetic/electrolyte solution is tested. Mice are restrained and released immediately following corneal stimulation that allows for the observation of the entire seizure episode. A maximal seizure in a test animal includes four distinct phases that includes, hind leg flexor component tonic phase (Phase I), hind leg extensor component of the tonic phase (Phase II), intermittent, whole-body clonus (Phase III), and muscular relaxation (Phase IV) followed by seizure termination (Woodbury & Davenport, 1952; Racine et al., 1972). Test compounds are tested for their ability to abolish hind limb tonic extensor component that indicates the compound's ability to inhibit MES-induced seizure spread. Compounds are pre-administered (i.p) and tested at various time points for the abolishment of hind limb tonic extensor component after electrical stimulus.

Corneal-Kindled Mouse Model of Partial Seizures

In corneal kindled seizure model, mice are kindled electrically with stimulation delivered through corneal electrodes primed with tetracaine hydrochloride in saline, twice daily, until 5 consecutive stage V seizures are induced. Mice are considered kindled when they display at least 5 consecutive stage V seizures according to the Racine scale (Racine et al., 1972) including, mouth and facial clonus (stage I), Stage I plus head nodding (Stage II), Stage II plus forelimb clonus (Stage III), Stage III plus rearing (Stage IV), and stage IV plus repeated rearing and falling (Stage V) (Racine et al., 1972). At the completion of the kindling acquisition, mice are permitted a 3-day stimulation-free period prior to any drug testing. On the day of the experiment, fully kindled mice are pre-administered (i.p) with increasing doses of the test compound and challenged with the corneal kindling stimulus. Mice are scored as protected (seizure score of <3) or not protected, (seizure score ≥4) based on the Racine scoring (Racine et al., 1972).

Pharmaceutical Compositions

The present application relates to pharmaceutical compositions comprising a compound of the application as an active ingredient. In one embodiment, the application provides a pharmaceutical composition comprising at least one compound of each of the formulae described herein, or a pharmaceutically acceptable salt or solvate thereof, and one or more pharmaceutically acceptable carriers or excipients. In one embodiment, the application provides a pharmaceutical composition comprising at least one compound selected from Table 1.

As used herein, the term "composition" is intended to encompass a product comprising the specified ingredients in the specified amounts, as well as any product which results, directly or indirectly, from combination of the specified ingredients in the specified amounts.

The compounds of the application can be formulated for oral administration in forms such as tablets, capsules (each of which includes sustained release or timed release formulations), pills, powders, granules, elixirs, tinctures, suspensions, syrups and emulsions. The compounds of the application can also be formulated for intravenous (bolus or in-fusion), intraperitoneal, topical, subcutaneous, intramuscular or transdermal (e.g., patch) administration, all using forms well known to those of ordinary skill in the pharmaceutical arts.

The formulation of the present application may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

Any suitable solubility enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulphated β-cyclodextrin (S13-CD), maltosyl-β-cyclodextrin, β-cyclodextrin sulfobutyl ether, branched-β-cyclodextrin, hydroxypropyl-γ-cyclodextrin, randomly methylated-γ-cyclodextrin, and trimethyl-γ-cyclodextrin, and mixtures thereof.

Any suitable chelating agent can be used. Examples of a suitable chelating agent include those selected from the group consisting of ethylenediaminetetraacetic acid and metal salts thereof, disodium edetate, trisodium edetate, and tetrasodium edetate, and mixtures thereof.

Any suitable preservative can be used. Examples of a preservative include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-p-hydroxybenzoate, and sorbic acid, and mixtures thereof.

The aqueous vehicle may also include a tonicity agent to adjust the tonicity (osmotic pressure). The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof.

The aqueous vehicle may also contain a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974 and Carbopol 974P), and a mixture thereof.

In order to adjust the formulation to an acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilize the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and ε-aminocaproic acid, and mixtures thereof.

The formulation may further comprise a wetting agent. Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Methods of Use

The present application relates to methods for the use of compounds of the application. The compounds of the application have a useful pharmacological activity spectrum and are therefore particularly suitable for the prophylaxis and/or treatment of diseases or disorders.

The present application provides a method of treating or preventing diseases or disorders, comprising administering a therapeutically effective amount of a compound of the application, or a pharmaceutically acceptable salt or solvate thereof, to a subject in need thereof. The present application also provides the use of a compound of the application, or a pharmaceutically acceptable salt or solvate thereof, for the preparation of a medicament for administration to a subject for the treatment or prevention of diseases or disorders. The present application also provides a compound of the application, or a pharmaceutically acceptable salt or solvate thereof, for treating or preventing diseases or disorders.

In one embodiment, the disease or disorder is a condition which can be ameliorated by KCNQ2/3 potassium channel opening. In one embodiment, the disease or disorder is selected from epilepsy, neurotransmission disorder, CNS disorder, neurodegenerative disease (e.g., Alzheimer's disease, ALS, motor neuron disease, Parkinson's disease, macular degeneration, or glaucoma), cognitive disorder (e.g., degenerative dementia (including senile dementia, Alzheimer's disease, Pick's disease, Huntington's chorea, Parkinson's disease, and Creutzfeldt-Jakob disease); vascular dementia (including multi-infarct dementia); dementia associated with intracranial space occupying lesions, trauma, infections or related conditions (including HIV infection), metabolism, toxins, anoxia, or vitamin deficiency; mild cognitive impairment associated with ageing, particularly Age Associated Memory Loss, or learning deficiencies), bipolar disorder (e.g., Type I or II bipolar disorder), unipolar depression, anxiety, migraine, ataxia, myokimia, tinnitus, functional bowel disorders (e.g., non-ulcer dyspepsia, non-cardiac chest pain, or irritable bowel syndrome), cancer, inflammatory disease, ophthalmic disease (e.g., retinitis, retinopathies, uveitis, or acute injury to the eye tissue), asthma, allergic rhinitis, respiratory distress syndrome, gastrointestinal conditions (e.g., inflammatory bowel disease, Chron's disease, gastritis, irritable bowel syndrome, or ulcerative colitis), and inflammation in such diseases as vascular disease, migraine, periarteritis nodosa, thyroiditis, aplastic anemia, Hodgkin's disease, sclerodoma, type I diabetes, myasthenia gravis, multiple sclerosis, sorcoidosis, nephrotic syndrome, Bechet's syndrome, polymyositis, gingivitis, conjunctivitis, and myocardial ischemia.

In one embodiment, the application provides a method of producing an anti-epileptic, muscle relaxing, fever reducing, peripherally analagesic, and/or anti-convulsive effect in a subject in need thereof, comprising administering to the subject an effective amount of a compound of the application, or a pharmaceutically acceptable salt or solvate thereof. The present application also provides the use of a compound of the application, or a pharmaceutically acceptable salt or solvate thereof, for the preparation of a medicament for administration to a subject for producing an anti-epileptic, muscle relaxing, fever reducing, peripherally analagesic, and/or anti-convulsive effect. The present application also provides a compound of the application, or a pharmaceutically acceptable salt or solvate thereof, for producing an anti-epileptic, muscle relaxing, fever reducing, peripherally analagesic, and/or anti-convulsive effect.

In one embodiment, the application provides compounds that are useful as an anticonvulsant. They are therefore useful in treating or preventing epilepsy. Compounds of the application may be used to improve the condition of a host, typically a human being, suffering from epilepsy. They may be employed to alleviate the symptoms of epilepsy in a host. "Epilepsy" is intended to include the following seizures: simple partial seizures, complex partial seizures, secondary generalized seizures, generalized seizures including absence seizures, myoclonic seizures, clonic seizures, tonic seizures, tonic clonic seizures and atonic seizures. Partial-onset seizures are the most common type of seizure in adult patients.

For partial seizures, there is a focal epileptic zone (site of seizure onset), and seizure activity is initially limited to one hemisphere. Partial seizures can be further sub-divided into simple partial (without impairment of consciousness), complex partial (with impairment of consciousness with or following a simple partial onset) and secondarily generalized (i.e., partial seizures, either simple or complex, which evolve to generalized tonic-clonic seizures). Simple partial seizures, depending on the anatomical site of origin of the seizure, may have motor, somatosensory or special sensory, autonomic or psychic signs or symptoms.

In one embodiment, the application provides a method of treating a subject suffering from or susceptible to epilepsy, comprising administering to the subject an effective amount of a compound of the application or a pharmaceutically acceptable salt or solvate thereof. The present application also provides the use of a compound of the application, or a pharmaceutically acceptable salt or solvate thereof, for the preparation of a medicament for administration to a subject suffering from or susceptible to epilepsy for the treatment of epilepsy. The present application also provides a compound of the application, or a pharmaceutically acceptable salt or solvate thereof, for treating a subject suffering from or susceptible to epilepsy.

In one embodiment, the application provides a method for the adjunctive treatment of adults with partial-onset seizures, comprising administering to the subject an effective amount of a compound of the application or a pharmaceutically acceptable salt thereof. The present application also provides the use of a compound of the application, or a pharmaceutically acceptable salt or solvate thereof, for the preparation of a medicament for adjunctive treatment of adults with partial-onset seizures. The present application also provides a compound of the application, or a pharmaceutically acceptable salt or solvate thereof, for adjunctive treatment of adults with partial-onset seizures.

In one embodiment, the present application provides a method of treating or preventing epilepsy, comprising administering a therapeutically effective amount of a compound of the application, or a pharmaceutically acceptable salt or solvate thereof, to a subject in need thereof. The present application also provides the use of a compound of the application, or a pharmaceutically acceptable salt or solvate thereof, for the preparation of a medicament for administration to a subject for the treatment or prevention of epilepsy. The present application also provides a compound of the application, or a pharmaceutically acceptable salt or solvate thereof, for treating or preventing epilepsy.

In one embodiment, a compound of the application is administered in combination with one or more anti-epileptic drugs (AEDs). There are different types of AEDs. For example, narrow-spectrum AEDs include phenytoin (Dilantin), phenobarbital, carbamazepine (Tegretol), oxcarbazepine (Trileptal), gabapentin (Neurontin), pregabalin (Lyrica), lacosamide (Vimpat), and vigabatrin (Sabril). Broad spectrum AEDs include valproic acid (Depakote), lamotrigine (Lamictal), topiramate (Topamax), zonisamide (Zonegran), levetiracetam (Keppra), clonazepam (Klonopin), and rufinamide (Banzel). In one embodiment, the AED is any AED. In one embodiment, the AED is a narrow spectrum AED. In one embodiment, the AED is a broad spectrum AED In one embodiment, the application provides compounds that are useful as analgesics. The compounds are therefore useful in treating or preventing pain. They may be used to improve the condition of a host, typically a human being, suffering from pain. They may be employed to alleviate pain in a host. Thus, the compounds may be used as a preemptive analgesic to treat acute pain such as musculoskeletal pain, post-operative pain and surgical pain, chronic pain such as chronic inflammatory pain (e.g., rheumatoid arthritis and osteoarthritis), neuropathic pain (e.g., post herpetic neuralgia, trigeminal neuralgia and sympathetically maintained pain) and pain associated with cancer and fibromyalgia. The compounds may also be used in the treatment or prevention of pain associated with migraine. The compounds may also be used in the treatment of the pain (both chronic and acute), fever and inflammation of conditions such as rheumatic fever; symptoms associated with influenza or other viral infections, such as the common cold; lower back and neck pain; headache; toothache; sprains and strains; myositis; neuralgia; synovitis; arthritis, including rheumatoid arthritis; degenerative joint diseases, including osteoarthritis; gout and ankylosing spondylitis; tendinitis; bursitis; skin related conditions, such as psoriasis, eczema, burns and dermatitis; injuries, such as sports injuries and those arising from surgical and dental procedures.

In one embodiment, the application provides a method of producing an analgesic effect in a subject in need thereof, comprising administering to the subject an effective amount of a compound of the application or a pharmaceutically acceptable salt or solvate thereof. The present application also provides the use of a compound of the application, or a pharmaceutically acceptable salt or solvate thereof, for the preparation of a medicament for administration to a subject for producing an analgesic effect. The present application also provides a compound of the application, or a pharmaceutically acceptable salt or solvate thereof, for producing an analgesic effect. In one embodiment, the analgesic effect is a neuroprotective effect. In one embodiment, the analgesic effect is a centrally acting analgesic effect.

In one embodiment, the application provides a method of treating or preventing a neurotransmission disorder, CNS disorder, neurodegenerative disease (e.g., Alzheimer's disease, ALS, motor neuron disease, Parkinson's disease, macular degeneration and glaucoma), cognitive disorder, bipolar disorder (e.g., Type I or II bipolar disorder), unipolar depression, or anxiety in a subject in need thereof, comprising administering to the subject an effective amount of a compound of the application or a pharmaceutically acceptable salt or solvate thereof. The present application also provides the use of a compound of the application, or a pharmaceutically acceptable salt or solvate thereof, for the preparation of a medicament for administration to a subject for treating or preventing a neurotransmission disorder, CNS disorder, neurodegenerative disease (e.g., Alzheimer's disease, ALS, motor neuron disease, Parkinson's disease, macular degeneration and glaucoma), cognitive disorder, bipolar disorder (e.g., Type I or II bipolar disorder), unipolar depression, or anxiety. The present application also provides a compound of the application, or a pharmaceutically acceptable salt or solvate thereof, for treating or preventing a neurotransmission disorder, CNS disorder, neurodegenerative disease (e.g., Alzheimer's disease, ALS, motor neuron disease, Parkinson's disease, macular degeneration and glaucoma), cognitive disorder, bipolar disorder (e.g., Type I or II bipolar disorder), unipolar depression, or anxiety.

In one embodiment, the application provides a method of treating or preventing migraine, ataxia, myokimia, tinnitus, and functional bowel disorders (e.g., non-ulcer dyspepsia, non-cardiac chest pain, or irritable bowel syndrome) in a subject in need thereof, comprising administering to the subject an effective amount of a compound of the application or a pharmaceutically acceptable salt or solvate thereof. The present application also provides the use of a compound of the application, or a pharmaceutically acceptable salt or solvate thereof, for the preparation of a medicament for administration to a subject for treating or preventing migraine, ataxia, myokimia, tinnitus, and functional bowel disorders (e.g., non-ulcer dyspepsia, non-cardiac chest pain, or irritable bowel syndrome). The present application also provides a compound of the application, or a pharmaceutically acceptable salt or solvate thereof, for treating or preventing migraine, ataxia, myokimia, tinnitus, and functional bowel disorders (e.g., non-ulcer dyspepsia, non-cardiac chest pain, or irritable bowel syndrome).

In one embodiment, the application provides compounds that are useful in the treatment of CNS disorders such as bipolar disorder, alternatively known as manic depression. The compounds may thus be used to improve the condition of a human patient suffering from bipolar disorder. They may be used to alleviate the symptoms of bipolar disorder in a host. The compounds may also be used in the treatment of unipolar depression, ataxia, myokimia and anxiety.

In one embodiment, the application provides compounds that are useful in the treatment of neurodegenerative diseases, such as Alzheimer's disease, ALS, motor neuron disease, Parkinson's disease, macular degeneration and glaucoma. The compounds of the application may also be useful in neuroprotection and in the treatment of neurodegeneration following stroke, cardiac arrest, pulmonary bypass, traumatic brain injury, spinal cord injury or the like. In one embodiment, compounds of the application are further useful in the treatment of tinnitus.

In one embodiment, the application provides compounds that are useful in the treatment of functional bowel disorders which include non-ulcer dyspepsia, non-cardiac chest pain and in particular irritable bowel syndrome. Irritable bowel syndrome is a gastrointestinal disorder characterized by the presence of abdominal pain and altered bowel habits without any evidence of organic disease. The compounds may thus be used to alleviate pain associated with irritable bowel syndrome. The condition of a human patient suffering from irritable bowel syndrome may thus be improved.

In one embodiment, the application provides a method of preventing or reducing dependence on, or preventing or reducing tolerance, or reverse tolerance, to a dependence-inducing agent in a subject in need thereof, comprising administering to the subject an effective amount of a compound of the application or a pharmaceutically acceptable salt or solvate thereof. The present application also provides the use of a compound of the application, or a pharmaceutically acceptable salt or solvate thereof, for the preparation of a medicament for administration to a subject for preventing or reducing dependence on, or preventing or reducing tolerance, or reverse tolerance, to a dependence-inducing agent. The present application also provides a compound of the application, or a pharmaceutically acceptable salt or solvate thereof, for preventing or reducing dependence on, or preventing or reducing tolerance, or reverse tolerance, to a dependence-inducing agent. Examples of dependence inducing agents include opioids (e.g., morphine), CNS depressants (e.g., ethanol), psychostimulants (e.g., cocaine) and nicotine.

In one embodiment, the application provides a method of treating or preventing cancer, inflammatory disease, or ophthalmic disease in a subject in need thereof comprising administering to the subject an effective amount of a compound of the application or a pharmaceutically acceptable salt or solvate thereof. The present application also provides the use of a compound of the application, or a pharmaceutically acceptable salt or solvate thereof, for the preparation of a medicament for administration to a subject for treating or preventing cancer, inflammatory disease, or ophthalmic disease. The present application also provides a compound of the application, or a pharmaceutically acceptable salt or solvate thereof, for treating or preventing cancer, inflammatory disease, or ophthalmic disease.

In one embodiment, the application provides compounds that inhibit cellular and neoplastic transformation and metastatic tumor growth and hence are useful in the treatment of certain cancerous diseases, such as colonic cancer.

In one embodiment, the application provides compounds that inhibit inflammatory processes and therefore are of use in the treatment of asthma, allergic rhinitis and respiratory distress syndrome; gastrointestinal conditions such as inflammatory bowel disease, Chron's disease, gastritis, irritable bowel syndrome and ulcerative colitis; and the inflammation in such diseases as vascular disease, migraine, periarteritis nodosa, thyroiditis, aplastic anemia, Hodgkin's disease, sclerodoma, type I diabetes, myasthenia gravis, multiple sclerosis, sorcoidosis, nephrotic syndrome, Bechet's syndrome, polymyositis, gingivitis, conjunctivitis and myocardial ischemia.

In one embodiment, the application provides compounds that are useful in the treatment of ophthalmic diseases such as retinitis, retinopathies, uveitis, and acute injury to the eye tissue.

In one embodiment, the application provides compounds that are useful for the treatment of cognitive disorders such as dementia, particularly degenerative dementia (including senile dementia, Alzheimer's disease, Pick's disease, Huntington's chorea, Parkinson's disease and Creutzfeldt-Jakob disease), and vascular dementia (including multi-infarct dementia), as well as dementia associated with intracranial space occupying lesions, trauma, infections and related conditions (including HIV infection), metabolism, toxins, anoxia and vitamin deficiency; and mild cognitive impairment associated with ageing, particularly Age Associated Memory Loss; and learning deficiencies.

In one embodiment, the application provides a method of producing an anxiolytic effect in a subject in need thereof comprising administering to the subject an effective amount of a compound of the application or a pharmaceutically acceptable salt or solvate thereof. In one embodiment, the application provides a method for the treatment of anxiety and its related psychological and physical symptoms. Anxiolytics have been shown to be useful in the treatment of anxiety disorders. The present application also provides the use of a compound of the application, or a pharmaceutically acceptable salt or solvate thereof, for the preparation of a medicament for administration to a subject for producing an anxiolytic effect. The present application also provides a compound of the application, or a pharmaceutically acceptable salt or solvate thereof, for producing an anxiolytic effect.

In one embodiment, the application provides compounds for treatment. In one embodiment, the application provides compounds for prophylaxis. In one embodiment, the application provides compound for alleviation of established symptoms.

Administration may for example be in the form of tablets, capsules, pills, coated tablets, suppositories, ointments, gels, creams, powders, dusting powders, aerosols or in liquid form. Liquid application forms that may for example be considered are: oils or alcoholic or aqueous solutions as well as suspensions and emulsions. In one embodiment, the application provides forms of application that are tablets that contain between 30 and 60 mg or solutions that contain between 0.1 to 5 percent by weight of active substance.

In one embodiment, a compound of the application is used in human medicine. In one embodiment, the compound of the application is used in veterinary medicine. In one embodiment, a compound of the application is used in agriculture. In one embodiment, a compound of the application is used alone or mixed with other pharmacologically active substances.

The following Examples are illustrative and should not be interpreted in any way so as to limit the scope of the application.

EXAMPLES

Example 1a: Compound 1

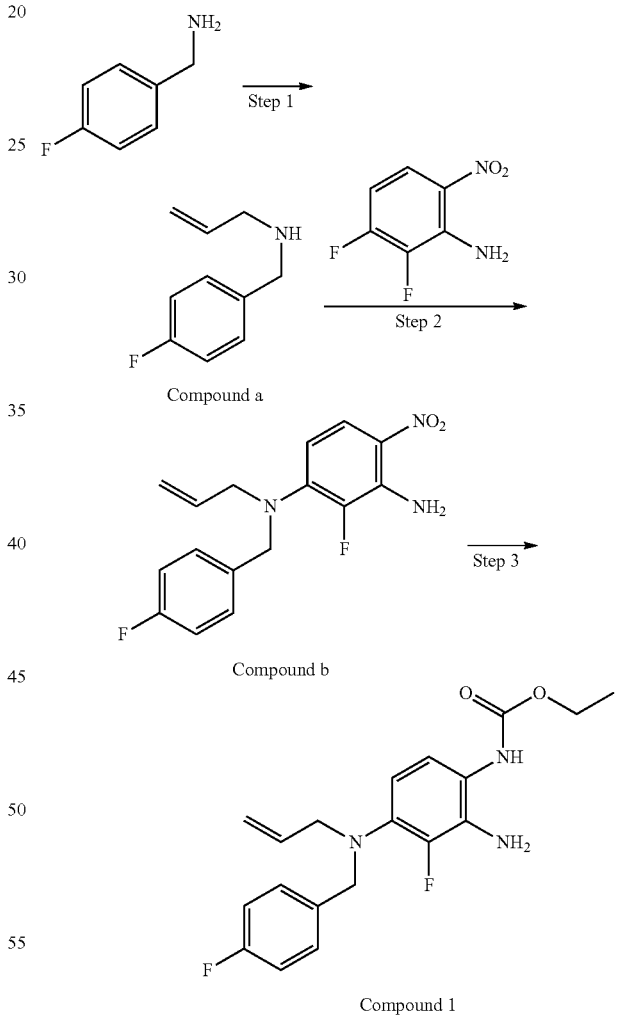

Step 1: Synthesis of Compound a

To a stirred solution of 4-fluorobenzylamine (1 equivalent (equiv)) dissolved in dimethylformamide (DMF) is added allyl bromide (1.5 equiv) and diisopropyl ethylamine (2 equiv) dropwise, and the resulting mixture is heated to 80° C. After 2 hours, the reaction mixture is cooled, diluted with water, and extracted with ethyl acetate (EtOAc). The organic layer is then washed with saturated brine, dried with anhydrous sodium sulfate, filtered, and concentrated under vacuum. The resulting residue is purified by silica gel liquid chromatography to provide Compound a.

Step 2: Synthesis of Compound b

To a stirred suspension of 2,3-difluoro-6-nitroaniline (1 equiv) in dry dimethyl sulfoxide (DMSO) is added Compound a (3 equiv) followed by $Et_3N$ (1.2 equiv) and $I_2$ (catalytic amount). The resulting mixture is heated to 120° C. and stirred at 120° C. for 24 hours. Upon complete consumption of the starting material (as determined by thin layer chromatography (TLC)), the reaction mixture is cooled to RT, diluted with water (25 mL), and extracted with EtOAc (2×25 mL). The combined organic layers are dried over anhydrous $Na_2SO_4$, filtered, and concentrated under reduced pressure to give a crude product, which is purified by silica gel column chromatography to afford Compound b.

Step 3: Synthesis of Compound 1

To a stirred solution of Compound b (1 equiv) in methanol is added zinc powder (5 equiv) followed by the dropwise addition of ammonium chloride solution (5 equiv). After stirring at room temperature (RT) for 5 hours, N,N-diisopropylethylamine (DIPEA) (1.25 equiv) and ethyl chloroformate (1 equiv) are then added at 10° C., and the stirring is continued for another 3 hours at RT. Upon complete consumption of the starting material (as determined by TLC), the reaction mixture is diluted with water and stirred for 1 hour to give a solid product. The obtained solid is filtered, dissolved in EtOAc, and any un-dissolved solid is removed by filtration. The filtrate is concentrated to provide Compound 1 which is crystallized using n-hexane.

Example 1b: Compound 1

Step 1: Synthesis of 2-Fluoro-$N^1$-(4-fluorobenzyl)-4-nitrobenzene-1,3-diamine 2,3-Difluoro-6-nitroaniline (10.0 g, 79.9 mmole) was dissolved in anhydrous dimethylsulfoxide (90 mL). 4-fluorobenzylamine (9.3 g, 53.3 mmole) was added triethylamine (17.7 mL) and solid iodine (80 mg) were added and the mixture was heated at reflux for 4 h. under argon. The reaction was dissolved in ethyl acetate (200 mL) and extracted with water (3×100 mL). A yellow solid precipitated out of the organic layer to give 2-fluoro-M-(4-fluorobenzyl)-4-nitrobenzene-1,3-diamine (13.6 g, 91% yield).

Step 2: Synthesis of di-tert-butyl (3-fluoro-4-((4-fluorobenzyl)amino)-1,2-phenylene)dicarbamate 2-Fluoro-$N^1$-(4-fluorobenzyl)-4-nitrobenzene-1,3-diamine (13.55 g, 48.53 mmole) was dissolved in methanol (60 mL) and tetrahydrofuran (60 mL). The mixture was cooled in an ice bath and zinc powder (31.70 g, 485.3 mmole) was added followed by ammonium chloride (26.0 g, 485.3 mmole) in DI water (64 mL) over 30 min. Ethyl acetate (200 mL) was added and the mixture was extracted with water (200 mL) and the organic layer was evaporated to dryness. The residue was dissolved in tetrahydrofuran (200 mL) and di-tert-butyldicarbonate (15.9 g, 72.8 mmole) was added followed by solid sodium bicarbonate (8.15 g, 97.06 mmole) and then DI water (150 mL). The reaction was stirred for an 18 h. at ambient temperature. The reaction was filtered and evaporated to dryness. Ethyl acetate (200 mL) was added and then 3M $NH_4OH$ (2×200 mL). The organic layer was evaporated to dryness. It was chromatographed on a silica gel column (200 g) packed in hexane. The column polarity was increased to 16% ethyl acetate over 5 CV, held at 16% ethyl acetate for 2 CV, increased to 32% ethyl acetate over 4 CV, and then to 53% ethyl acetate over 2 CV. Flow rate at 100 mL/min. t 100 mL/min. Fractions (22 mL each) containing the product were pooled and stripped to give di-tert-butyl (3-fluoro-4-(4-fluorobenzyl)amino)-1,2-phenylene)dicarbamate (9.84 g, 45% yield).

Step 3: Synthesis of di-tert-butyl (4-(allyl(4-fluorobenzyl)amino)-3-fluoro-1,2-phenylene)dicarbamate Di-tert-butyl (3-fluoro-4-((4-fluorobenzyl)amino)-1,2-phenylene)dicarbamate (2.03 g, 4.52 mmole) was dissolved in anhydrous dimethylformamide (10 mL). Diisopropylethylamine (1.6 mL, 9.0 mmole) was added followed by allyl bromide (0.710 mg, 5.87 mmole). The mixture was heated in an 110° C. oil bath under argon for 6h. The reaction was diluted in ethyl acetate (100 mL) and extracted with water (100 mL). The aqueous layer was washed with ethyl acetate (100 mL). The organic layers were washed with water, 2×50 mL and then brine (50 mL) and filtered through a 1 PS filter to dry and evaporated to dryness. The crude material was chromatographed on a silica gel column (25 g) packed in hexanes. The column polarity was increased to 9% ethyl acetate over 4 CV, held at 9% ethyl acetate over 7 CV and then increased to 33% ethyl acetate over 12 CV. The flow rate was 25 mL/min. Fractions (22 mL each) containing the first product were pooled and stripped to give of di-tert-butyl (4-(allyl(4-fluorobenzyl)amino)-3-fluoro-1,2-phenylene)dicarbamate (1.35 g, 61% yield).

Step 4: Synthesis of ethyl (4-(allyl(4-fluorobenzyl) amino)-2-amino-3-fluorophenyl)carbamate (Compound 1)

The organic layer was evaporated to dryness, dissolved in methanol (5 mL) and tetrahydrofuran (5 mL) and cooled in an ice bath when N, N-diisopropylethylamine (1.2 mL, 6.72 mmole) was added followed by ethyl chloroformate (0.128 mL, 1.19 mmole) dropwise. The reaction was stirred at ambient temperature for 0.5 h and was evaporated to dryness. The crude oil was dissolved in ethyl acetate (10 mL) and extracted with water (10 mL). The organic layer was then dried through a 1 PS filter and evaporated to dryness. It was chromatographed on a silica gel column (10 g) packed in chloroform. The column polarity was increased to 30% ethyl acetate in chloroform over 7 CV, at 12 mL/min. Fractions (22 mL each) containing the product were pooled and stripped to give ethyl (4-(allyl(4-fluorobenzyl)amino)-2-amino-3-fluorophenyl)carbamate (0.115 g, 29% yield).

NMR Spectroscopy: $^1H$ NMR ($CDCl_3$, 500 MHz): δ 7.28 (m, 2H), 6.99 (t, 2H), 6.83 (d, 1H), 6.38 (t, 1H), 6.25 (br s, 1H), 5.80-5.89 (m, 1H), 5.18 (t, 2H), 4.30 (s, 2H), 4.25 (q, 2H), 3.84 (br s, 1H), 3.70 (d, 2H), 1.60 (br s, 1H), 1.32 (t, 3H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 µL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd1}$=8.2 min.

Example 2a: Compound 2

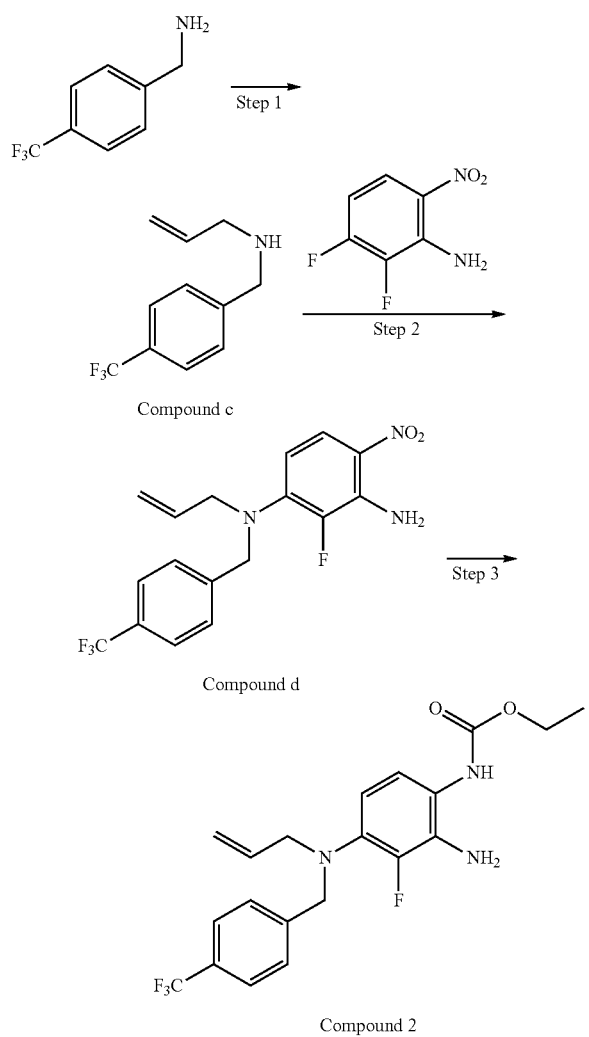

Compound c

Compound d

Compound 2

Step 1: Synthesis of Compound c

To a stirred solution of 4-trifluoromethylbenzylamine (1 equiv) dissolved in DMF is added allyl bromide (1.5 equiv) and diisopropyl ethylamine (2 equiv) dropwise, and the resulting mixture is heated to 80° C. After 2 hours, the reaction mixture is cooled, diluted with water, and extracted with ethyl acetate. The organic layer is then washed with saturated brine, dried with anhydrous sodium sulfate, filtered, and concentrated under vacuum. The resulting residue is purified by silica gel liquid chromatography to give Compound c.

Step 2: Synthesis of Compound d

To a stirred suspension of 2, 3-difluoro-6-nitroaniline (1 equiv) in dry DMSO is added Compound c (3 equiv) followed by Et$_3$N (1.2 equiv) and I$_2$ (catalytic amount). The reaction mixture is heated to 120° C. and stirred at 120° C. for 24 h. Upon complete consumption of the starting material (as determined by TLC), the reaction mixture is cooled to RT, diluted with water (25 mL), and extracted with EtOAc (2×25 mL). The combined organic layers are dried over anhydrous Na$_2$SO$_4$, filtered, and concentrated under reduced pressure to give a crude product, which is purified by silica gel column chromatography to afford Compound d.

Step 3: Synthesis of Compound 2

To a stirred solution of Compound d (1 equiv) in methanol is added zinc powder (5 equiv) followed by the dropwise addition of ammonium chloride solution (5 equiv). After stirring at RT for 5 hours, DIPEA (1.25 equiv) and ethyl chloroformate (1 equiv) are then added to reaction mixture at 10° C., and the stirring is continued for another 3 hours at RT. Upon complete consumption of the starting material (as determined by TLC), the reaction mixture is diluted with water and stirred for 1h to give a solid product. The obtained solid is filtered, dissolved in EtOAc, and any un-dissolved solid is removed by filtration. The filtrate is concentrated to provide Compound 2 which is crystallized using n-hexane.

Example 2b: Compound 2

Step 1: Synthesis of N-(4-(trifluoromethyl)benzyl)prop-2-en-1-amine 4-(Trifluoromethyl)benzylamine (8.76 g, 50 mmole) was cooled in an ice bath when allyl bromide (2.60 g, 20.0 mmole) in DCM (30 mL) was added dropwise over 1 h. The reaction was filtered and evaporated to dryness. It was chromatographed on a silica gel column (100 g) packed in hexanes. The column polarity was increased to 100% ethyl acetate over 10 CV, at 50 mL/min. Fractions (22 mL each) containing the second band were pooled and stripped to give N-(4-(trifluoromethyl)benzyl)prop-2-en-1-amine (1.42 g, 10.5% yield).

Step 2: Synthesis of N'-allyl-2-fluoro-4-nitro-N$^1$-(4-(trifluoromethyl)benzyl)benzene-1,3-diamine 2,3-Difluoro-6-nitroaniline (0.377 g, 2.17 mmole) was dissolved in anhydrous dimethylsulfoxide (4 mL). N-(4-(trifluoromethyl)benzyl)prop-2-en-1-amine (0.700 g, 3.25 mmole) was added followed by triethylamine (0.722 mL) and solid iodine (1 mg). The mixture was heated at reflux for 18 h. under argon. The reaction was dissolved in ethyl acetate (10 mL) and extracted with water (10 mL). The organic layer was washed with 3×30 mL water and then dried through a 1 PS filter and evaporated to dryness. The crude material was chromatographed on a silica gel column (25 g) packed in hexanes. The column polarity was increased to 100% ethyl acetate over 16 CV, at 25 mL/min. Fractions (22 mL each) containing the product were pooled and stripped to give N$^1$-allyl-2-fluoro-4-nitro-N$^1$-(4-(trifluoromethyl)benzyl)benzene-1,3-diamine (0.58 g, 71% yield).

Step 3: Synthesis of ethyl (4-(allyl(4-(trifluoromethyl)benzyl)amino)-2-amino-3-fluorophenyl)carbamate (Compound 2)

N$^1$-allyl-2-fluoro-4-nitro-N$^1$-(4-(trifluoromethyl)benzyl)benzene-1,3-diamine (0.392 g, 1.06 mmole) was dissolved in methanol (10 mL). Zinc powder (347 mg, 5.30 mmole) was added followed by ammonium chloride (284 mg, 5.30 mmole) in DI water (1.0 mL). The mixture was stirred under argon at ambient temperature for 2 h. and then cooled to 10° C. in an ice bath. N, N-diisopropylethylamine (0.221 mL, 1.27 mmole) was added, followed by ethyl chloroformate, dropwise (285 mg, 2.66 mmole) and the reaction was stirred at ambient temperature for 18 h. The reaction was dissolved in ethyl acetate (10 mL) and extracted with water (10 mL). The organic layer was washed with 2×10 mL water and then dried through a 1 PS filter and evaporated to dryness. The crude material was chromatographed on a silica gel column (25 g) packed in chloroform. The column polarity was increased to 20% ethyl acetate/chloroform over 10 CV, at 25 mL/min. Fractions (22 mL each) containing the product were pooled and stripped to give ethyl (4-(allyl(4-(trifluoromethyl)benzyl)amino)-2-amino-3-fluorophenyl)carbamate (0.331 g, 51% yield).

NMR Spectroscopy: $^1$H NMR (CDCl$_3$, 300 MHz): δ 7.56 (d, 2H), 7.43 (d, 2H), 7.24 (s, 1H), 6.85 (d, 1H), 6.34 (t, 1H), 6.20 (br s, 1H), 5.80-5.94 (m, 1H), 5.16-5.22 (m, 2H), 4.39 (s, 2H), 4.22 (q, 2H), 3.80-4.17 (br s, 1H), 3.75 (d, 2H), 1.33 (t, 3H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 µL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd2}$=12.2 min.

Example 3: Compound 3

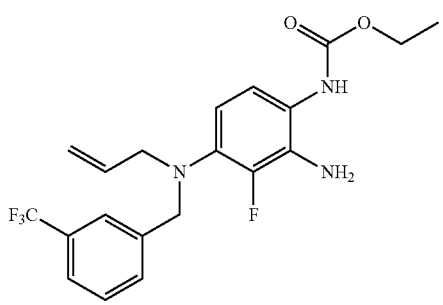

Step 1: Synthesis of N-(3-(trifluoromethyl)benzyl)prop-2-en-1-amine 3-(Trifluoromethyl)benzylamine (10.0 g, 57.1 mmole) was dissolved in anhydrous acetonitrile (36 mL). Potassium carbonate (7.90 g, 57.1 mmole) was added and the mixture was cooled in an ice bath when allyl bromide (4.91 g, 40.6 mmole) in anhydrous acetonitrile (3.5 mL) was added over 30 min. The reaction was stirred for 2 h at 0° C. and then warmed to ambient temperature. After 1 h, the mixture was cooled in an ice bath and allyl bromide (0.987 mL, 11.4 mmole) was added dropwise and then warmed to ambient temperature. It was filtered on a glass fiber filter and then evaporated. It was chromatographed on a silica gel column (100 g) packed in hexanes. The column polarity was increased to 100% ethyl acetate over 6 CV, at 50 mL/min. Fractions (22 mL each) containing the second band were pooled and stripped to give N-(3-(trifluoromethyl)benzyl) prop-2-en-1-amine (3.0 g, 24% yield).

Step 2: Synthesis of N$^1$-allyl-2-fluoro-4-nitro-N$^1$-(3-(trifluoromethyl)benzyl)benzene-1,3-diamine 2,3-Difluoro-6-nitroaniline (270 mg, 2.32 mmole) was dissolved in anhydrous dimethylsulfoxide (5 mL). N-(3-(trifluoromethyl)benzyl)prop-2-en-1-amine (0.500 g, 2.32 mmole) was added and solid triethylamine (0.708 mL) and solid iodine (1 mg). The mixture was heated at reflux for 18 h. under argon. The reaction was dissolved in dichloromethane (20 mL) and extracted with water (20 mL). The aqueous layer was washed with dichloromethane (20 mL). The organic layers were washed with water, 2×20 mL brine and evaporated to dryness. The crude material was chromatographed on a silica gel column (10 g) packed in hexanes. The column polarity was increased to 40% ethyl acetate over 10 CV, at 12 mL/min. Fractions (22 mL each) containing the product were pooled and stripped to give N$^1$-allyl-2-fluoro-4-nitro-N$^1$-(3-(trifluoromethyl)benzyl)benzene-1,3-diamine (0.320 g, 56% yield).

Step 3: Synthesis of ethyl (4-(allyl(3-(trifluoromethyl)benzyl)amino)-2-amino-3-fluorophenyl)carbamate (Compound 3)

N$^1$-allyl-2-fluoro-4-nitro-N$^1$-(3-(trifluoromethyl)benzyl) benzene-1,3-diamine (0.305 g, 0.826 mmole) was dissolved in methanol (4 mL) and tetrahydrofuran (4 mL). Zinc powder (0.540 g, 8.26 mmole) was added followed by ammonium chloride (442 mg, 8.26 mmole) in DI water (2 mL). The mixture was stirred under argon at ambient temperature for 15 min. The reaction was cooled in an ice bath and N, N-diisopropylethylamine (0.330 mL, 1.89 mmole) was added followed by ethyl chloroformate (159 mg, 1.49 mmole) dropwise. The reaction was stirred at ambient temperature for 12 h. The reaction was cooled in an ice bath and N, N-diisopropylethylamine (0.460 mL, 2.63 mmole) was added followed by ethyl chloroformate (244 mg, 2.30 mmole) dropwise. The reaction was stirred at ambient temperature for 18 h and was filtered and evaporated. The crude oil was dissolved in ethyl acetate (20 mL) and extracted with water (20 mL). the organic layer was then dried through a 1 PS filter and evaporated to dryness. It was chromatographed on a silica gel column (10 g) packed in chloroform. The column polarity was increased to 45% ethyl acetate in chloroform over 15 CV, at 12 mL/min. Fractions (22 mL each) containing the product were pooled and stripped to give ethyl (4-(allyl(3-(trifluoromethyl)benzyl) amino)-2-amino-3-fluorophenyl)carbamate (0.119 g, 30% yield).

NMR Spectroscopy: $^1$H NMR (CDCl$_3$, 500 MHz): δ 7.57 (s, 1H), 7.48 (m, 2H), 7.41 (t, 1H), 6.84 (d, 1H), 6.33 (t, 1H), 6.19 (br s, 1H), 5.80-5.89 (m, 1H), 5.16 (s, 1H), 5.13 (d, 1H), 4.35 (s, 2H), 4.21 (q, 2H), 3.85 (br s, 2H), 3.70 (d, 2H), 1.30 (t, 3H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 µL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd3}$=11.8 min.

Example 4: Compound 4

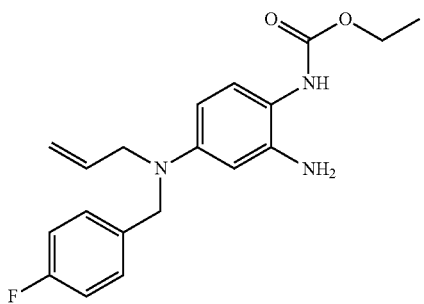 [SMILES: C=CCN(Cc1ccc(F)cc1)c1ccc(NC(=O)OCC)c(N)c1]

Step 1: Synthesis of di-tert-butyl (4-(allyl(4-fluorobenzyl)amino)-1,2-phenylene)dicarbamate Di-tert-butyl (4-((4-fluorobenzyl)amino)-1,2-phenylene) dicarbamate (0.937 g, 2.17 mmole) was dissolved in anhydrous dimethylformamide (10 mL). Diisopropylethylamine (0.755 mL, 4.34 mmole) was added followed by allyl bromide (0.237 mL, 2.82 mmole). The mixture was heated in an 110° C. oil bath under argon for 2h. The reaction was diluted in ethyl acetate (100 mL) and extracted with water (100 mL). The aqueous layer was washed with ethyl acetate (100 mL). The organic layers were washed with water, 2×50 mL and then brine (50 mL) and filtered through a 1 PS filter to dry and evaporated to dryness. The crude material was chromatographed on a silica gel column (25 g) packed in hexanes. The column polarity was increased to 12% ethyl acetate over 6 CV, held at 12% ethyl acetate over 2 CV and then increased to 40% ethyl acetate over 14 CV. The flow rate was 25 mL/min. Fractions (22 mL each) containing the first product were pooled and stripped to give di-tert-butyl (4-(allyl(4-fluorobenzyl)amino)-1,2-phenylene)dicarbamate (0.780 g, 76% yield).

Step 2: Synthesis of ethyl (4-(allyl(4-fluorobenzyl) amino)-2-aminophenyl)carbamate (Compound 4)

Di-tert-butyl (4-(allyl(4-fluorobenzyl)amino)-1,2-phenylene)dicarbamate (0.700 g, 1.48 mmole) was dissolved in dichloromethane (7 mL) and trifluoroacetic acid (7 mL) was added and the reaction was stirred at ambient temperature under argon for 65 min. The organic layer was evaporated to dryness, dissolved in methanol (7 mL) and tetrahydrofuran (7 mL) and cooled in an ice bath when N, N-diisopropylethylamine (1.6 mL, 9.20 mmole) was added followed by ethyl chloroformate (0.175 g, 1.63 mmole) dropwise. The reaction was stirred at ambient temperature for 1 h and was evaporated. The crude oil was dissolved in ethyl acetate (10 mL) and extracted with water (10 mL). The organic layer was then dried through a 1 PS filter and evaporated to dryness. It was chromatographed on a silica gel column (10 g) packed in hexanes. The column polarity was increased to 39% ethyl acetate over 6CV, held at 39% ethyl acetate over 2 CV and then increased to 100% ethyl acetate over 9 CV. Flow rate at 12 mL/min. Fractions (22 mL each) containing the product were pooled and stripped to give ethyl (4-(allyl (4-fluorobenzyl)amino)-2-aminophenyl)carbamate (0.209 g, 41% yield).

NMR Spectroscopy: $^1$H NMR (CDCl$_3$, 500 MHz): δ 7.21 (t, 2H), 7.00 (m, 3H), 6.18 (m, 3H), 5.90 (m, 1H), 5.21 (m, 2H), 4.47 (s, 2H), 4.20 (q, 2H), 3.95 (s, 3H), 1.30 (t, 3H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 μL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd4}$=6.4 min.

Example 5—Compound 5

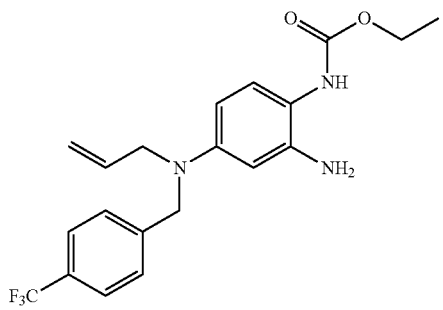

Step 1: Synthesis of N$^1$-allyl-4-nitro-N$^1$-(4-(trifluoromethyl)benzyl)benzene-1,3-diamine 5-Fluoro-2-nitroaniline (0.566 g, 3.62 mmole) was dissolved in anhydrous dimethylsulfoxide (5 mL). N-(4-(trifluoromethyl)benzyl)prop-2-en-1-amine (1.17 g, 5.44 mmole) was added triethylamine (1.80 mL) and solid iodine (1 mg) were added and the mixture was heated at reflux for an additional 18 h. under argon. The reaction was dissolved in ethyl acetate (10 mL) and extracted with water (10 mL). The organic layer was washed with 3×30 mL water and then dried through a 1 PS filter and evaporated to dryness. The crude material was chromatographed on a silica gel column (50 g) packed in hexanes. The column polarity was increased to 40% ethyl acetate/chloroform over 8 CV, at 50 mL/min. Fractions (22 mL each) containing the product were pooled and stripped to give N$^1$-allyl-4-nitro-N$^1$-(4-(trifluoromethyl)benzyl)benzene-1,3-diamine (0.182 g, 14% yield).

Step 2: Synthesis of ethyl (4-(allyl(4-(trifluoromethyl)benzyl)amino)-2-aminophenyl)carbamate (Compound 5)

N$^1$-allyl-4-nitro-N$^1$-(4-(trifluoromethyl)benzyl)benzene-1,3-diamine (0.182 g, 0.518 mmole) was dissolved in methanol (3 mL). Zinc powder (169 mg, 2.59 mmole) was added followed by ammonium chloride (139 mg, 2.59 mmole) in DI water (1.0 mL). The mixture was stirred under argon at ambient temperature for 30 min., and then zinc powder (169 mg, 2.59 mmole) was added followed by ammonium chloride (139 mg, 2.59 mmole) in DI water (1.0 mL) and tetrahydrofuran (3 mL). After 30 min., the mixture was cooled in an ice bath. N, N-diisopropylethylamine (0.378 mL, 2.18 mmole) was added, followed by ethyl chloroformate, dropwise (166 mg, 1.55 mmole) and the reaction was stirred at ambient temperature for 18 h. The reaction was filtered on a Buchner funnel with #4 Whatman filter paper. The filtrate was diluted with ethyl acetate (15 mL) and extracted with water (15 mL). The organic layer was washed with brine (15 mL), dried through a 1 PS filter and evaporated to dryness. It was chromatographed on a silica gel column (10g) packed in chloroform. The column polarity was increased to 3% ethyl acetate/chloroform over 2 CV, at 12 mL/min. Fractions (22 mL each) containing the product were pooled and stripped to give ethyl (4-(allyl(4-(trifluoromethyl)benzyl)amino)-2-aminophenyl)carbamate (0.017 g, 8.3% yield).

NMR Spectroscopy: $^1$H NMR (CDCl$_3$, 500 MHz): δ 7.59 (d, 2H), 7.38 (d, 2H), 6.96 (m, 1H), 6.18 (m, 2H), 6.08 (br s, 1H), 5.87 (m, 1H), 5.21 (m, 2H), 4.55 (s, 2H), 4.22 (q, 2H), 3.99 (s, 2H), 1.32 (t, 3H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 µL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd5}$=9.3 min.

Example 6: Compound 6

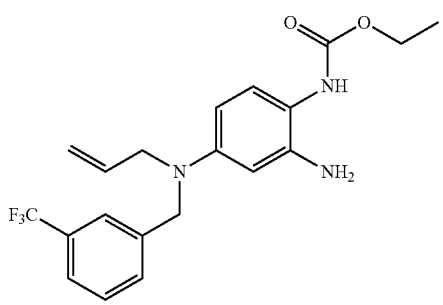 [SMILES: C=CCN(Cc1cccc(C(F)(F)F)c1)c1ccc(NC(=O)OCC)c(N)c1]

Step 1: Synthesis of 4-Nitro-N$^1$-(3-(trifluoromethyl)benzyl)benzene-1,3-diamine 5-Fluoro-2-nitroaniline (10.24 g, 58.46 mmole) was dissolved in anhydrous dimethylsulfoxide (90 mL). 3-fluorobenzylamine (6.1 g, 39.0 mmole) was added triethylamine (13.0 mL) and solid iodine (90 mg) were added and the mixture was heated at reflux for 4 h. under argon. The reaction was dissolved in ethyl acetate (200 mL) and extracted with water (3×200 mL). The combined aqueous layers were washed with (300 mL) ethyl acetate, combined and then evaporated to dryness. The crude material was triturated with hexane/ethyl acetate (7:3, 100 mL) and dried under high vacuum to give 4-nitro-N$^1$-(3-(trifluoromethyl)benzyl)benzene-1,3-diamine (8.29 g, 77% yield).

Step 2: Synthesis of di-tert-butyl (4-((tert-butoxycarbonyl)(3-(trifluoromethyl)benzyl)amino)-1,2-phenylene)dicarbamate 4-Nitro-N$^1$-(3-(trifluoromethyl)benzyl)benzene-1,3-diamine (10.8 g, 34.7 mmole) was dissolved in methanol (50 mL) and tetrahydrofuran (50 mL). Zinc powder (22.7 g, 347 mmole) was added followed by ammonium chloride (18.6 g, 347 mmole) in DI water (46 mL) over 30 min. The mixture was stirred under argon at ambient temperature for 30 min. The reaction was filtered on a celite pad which was washed with methanol (200 mL) and the mixture was evaporated to dryness. Ethyl acetate (200 mL) was added and the mixture was extracted with water (200 mL) and brine (50 mL) and evaporated to dryness. The residue was dissolved in tetrahydrofuran (150 mL) and di-tert-butyldicarbonate (22.1 g, 101.3 mmole) was added followed by solid sodium bicarbonate (11.63 g, 138.4 mmole) and then DI water (100 mL). The reaction was stirred for an 18 h. at ambient temperature. The reaction was evaporated to dryness. and ethyl acetate (200 mL) was added. The organic layer was extracted with water (3×200 mL) and brine (50 mL) and evaporated to dryness. It was chromatographed on a silica gel column (200 g) packed in hexane. The column polarity was increased to 35% ethyl acetate in hexanes over 9 CV, at 100 mL/min. Fractions (22 mL each) containing the product were pooled and stripped to give di-tert-butyl (4-((tert-butoxycarbonyl)(3-(trifluoromethyl)benzyl)amino)-1,2-phenylene)dicarbamate (13.1 g, 65% yield).

Step 3: Synthesis of di-tert-butyl (4-((3-(trifluoromethyl)benzyl)amino)-1,2-phenylene)dicarbamate Di-tert-butyl (4-((tert-butoxycarbonyl)(3-(trifluoromethyl)benzyl)amino)-1,2-phenylene)dicarbamate (13.0 g, 22.4 mmole) was dissolved in dichloromethane (75 mL) and trifluoroacetic acid (50 mL) was added and the reaction was stirred at ambient temperature under argon for 60 min. The reaction was evaporated to give an off-white solid. The solid was dissolved in dioxane (125 mL) and di-tert-butyldicarbonate (10.24 g, 46.94 mmole) was added followed by solid sodium bicarbonate (7.51 g, 89.4 mmole) and then DI water (50 mL). The reaction was heated to 40° C. with stirring for 18 h., under argon. The reaction was evaporated and ethyl acetate (200 mL) was added. The organic layer was extracted with 3M NH$_4$OH (2×100 mL) and brine (50 mL), dried through a 1 PS filter and evaporated to dryness. It was chromatographed on a silica gel column (200 g) packed in hexane. The column polarity was increased to 45% ethyl acetate in hexanes over 12 CV, at 100 mL/min. Fractions (22 mL each) containing the product were pooled and stripped to give di-tert-butyl (4-((3-(trifluoromethyl)benzyl)amino)-1,2-phenylene)dicarbamate (1.3 g, 65% yield).

Step 4: Synthesis of di-tert-butyl (4-(allyl(3-(trifluoromethyl)benzyl)amino)-1,2-phenylene)dicarbamate Di-tert-butyl (4-((3-(trifluoromethyl)benzyl)amino)-1,2-phenylene)dicarbamate (2.0 g, 4.2 mmole) was dissolved in anhydrous dimethylformamide (20 mL). Diisopropylethylamine (2.2 mL, 12.5 mmole) was added followed by allyl bromide (0.803 mL, 9.55 mmole). The mixture was heated in an 110° C. oil bath under argon for 2h. The reaction was diluted in ethyl acetate (200 mL) and extracted with water (200 mL), and then brine (50 mL) and filtered through a 1 PS filter to dry and evaporated to dryness. The crude material was chromatographed on a silica gel column (25 g) packed in hexanes. The column polarity was increased to 37% ethyl acetate in hexanes over 14 CV. The flow rate was 25 mL/min. Fractions (22 mL each) containing the first product were pooled and stripped to give of di-tert-butyl (4-(allyl(3-(trifluoromethyl)benzyl)amino)-1,2-phenylene) dicarbamate (1.63 g, 75% yield).

Step 5: Synthesis of ethyl (4-(allyl(3-(trifluoromethyl)benzyl)amino)-2-aminophenyl)carbamate (Compound 6)

Di-tert-butyl (4-(allyl(3-(trifluoromethyl)benzyl)amino)-1,2-phenylene)dicarbamate (1.0 g, 1.92 mmole) was dissolved in dichloromethane (7 mL) and trifluoroacetic acid (7 mL) was added and the reaction was stirred at ambient temperature under argon for 90 min. The organic layer was evaporated to dryness, dissolved in methanol (5 mL) and tetrahydrofuran (5 mL) and cooled in an ice bath when N,N-diisopropylethylamine (2.1 mL, 11.9 mmole) was added followed by ethyl chloroformate (0.225 mL, 2.11 mmole) dropwise. The reaction was stirred at ambient temperature for 18 h and was filtered and evaporated. The crude oil was dissolved in ethyl acetate (20 mL) and extracted with water (20 mL). The organic layer was then dried through a 1 PS filter and evaporated to dryness. It was chromatographed on a silica gel column (25 g) packed in chloroform. The column polarity was increased to 100% ethyl acetate in hexanes over 26 CV, at 25 mL/min. Fractions (22 mL each) containing the product were pooled and stripped to give ethyl (4-(allyl(3-(trifluoromethyl)benzyl)amino)-2-aminophenyl)carbamate (0.150 g, 20% yield).

NMR Spectroscopy: $^1$H NMR (CDCl$_3$, 500 MHz): δ 7.48 (s, 2H), 7.41 (s, 2H), 6.92 (d, 1H), 6.15 (d, 1H), 6.07 (s, 1H), 6.00 (br s, 1H), 5.85 (m, 1H), 5.15-5.20 (m, 2H), 4.50 (s, 2H), 4.18 (q, 2H), 3.95 (s, 2H), 3.75 (br s, 2H), 1.26 (t, 3H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 μL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd6}$=8.8 min.

Example 7: Compound 7

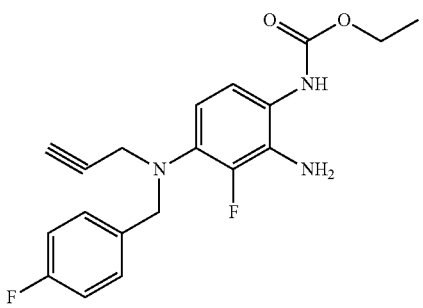 [SMILES: C#CCN(Cc1ccc(F)cc1)c1ccc(NC(=O)OCC)c(N)c1F]

Step 1: Synthesis of 2-Fluoro-N$^1$-(4-fluorobenzyl)-4-nitrobenzene-1,3-diamine 2,3-Difluoro-6-nitroaniline (10.0 g, 79.9 mmole) was dissolved in anhydrous dimethylsulfoxide (90 mL). 4-fluorobenzylamine (9.3 g, 53.3 mmole) was added triethylamine (17.7 mL) and solid iodine (80 mg) were added and the mixture was heated at reflux for 4 h. under argon. The reaction was dissolved in ethyl acetate (200 mL) and extracted with water (3×100 mL). A yellow solid precipitated out of the organic layer to give 2-fluoro-N$^1$-(4-fluorobenzyl)-4-nitrobenzene-1,3-diamine (13.6 g, 91% yield).

Step 2: Synthesis of di-tert-butyl (3-fluoro-4-((4-fluorobenzyl)amino)-1,2-phenylene)dicarbamate 2-Fluoro-N$^1$-(4-fluorobenzyl)-4-nitrobenzene-1,3-diamine (13.55 g, 48.53 mmole) was dissolved in methanol (60 mL) and tetrahydrofuran (60 mL). The mixture was cooled in an ice bath and zinc powder (31.70 g, 485.3 mmole) was added followed by ammonium chloride (26.0 g, 485.3 mmole) in DI water (64 mL) over 30 min. Ethyl acetate (200 mL) was added and the mixture was extracted with water (200 mL) and the organic layer was evaporated to dryness. The residue was dissolved in tetrahydrofuran (200 mL) and di-tert-butyldicarbonate (15.9 g, 72.8 mmole) was added followed by solid sodium bicarbonate (8.15 g, 97.06 mmole) and then DI water (150 mL). The reaction was stirred for an 18 h. at ambient temperature. The reaction was filtered and evaporated to dryness. Ethyl acetate (200 mL) was added and then 3M NH$_4$OH (2×200 mL). The organic layer was evaporated to dryness. It was chromatographed on a silica gel column (200 g) packed in hexane. The column polarity was increased to 16% ethyl acetate over 5 CV, held at 16% ethyl acetate for 2 CV, increased to 32% ethyl acetate over 4 CV, and then to 53% ethyl acetate over 2 CV. Flow rate at 100 mL/min. t 100 mL/min. Fractions (22 mL each) containing the product were pooled and stripped to give di-tert-butyl (3-fluoro-4-((4-fluorobenzyl)amino)-1,2-phenylene)dicarbamate (9.84 g, 45% yield).

Step 3: Synthesis of di-tert-butyl (3-fluoro-4-((4-fluorobenzyl)(prop-2-yn-1-yl)amino)-1,2-phenylene) dicarbamate Di-tert-butyl (3-fluoro-4-((4-fluorobenzyl)amino)-1,2-phenylene)dicarbamate (2.00 g, 4.45 mmole) was dissolved in anhydrous dimethylformamide (20 mL), 80% propargyl bromide in toluene (0.618 mL, 5.78 mmole) and diisopropylethylamine (1.50 mL, 8.90 mmole). The mixture was heated in a 90° C. oil bath, under argon, for 0.5 h. 80% propargyl bromide in toluene (0.65 mL, 5.78 mmole) and diisopropylethylamine (1.50 mL, 8.90 mmole) were added and heated at 100° C. for 4.5h. 80% propargyl bromide in toluene (0.618 mL, 5.78 mmole) and diisopropylethylamine (1.50 mL, 8.90 mmole) were added and the reaction was heated at 100° for 18 h. 80% propargyl bromide in toluene (0.618 mL, 5.78 mmole) was added and the mixture was heated for 2 h. at 100° C. The reaction was diluted in ethyl acetate (100 mL) and extracted with water (100 mL) and brine (50 mL), filtered through a 1 PS filter and evaporated to dryness. The crude material was chromatographed on a silica gel column (25 g) packed in hexanes. The column polarity was increased to 40% ethyl acetate over 15 CV, at 25 mL/min. Fractions (22 mL each) containing the product were pooled and stripped to give (1.01 g, 47% yield) di-tert-butyl (3-fluoro-4-(4-fluorobenzyl)(prop-2-yn-1-yl) amino)-1,2-phenylene)dicarbamate (1.35 g, 61% yield).

Step 4: Synthesis of ethyl (2-amino-3-fluoro-4-((4-fluorobenzyl)(prop-2-yn-1-yl)amino)phenyl)carbamate (Compound 7)

Di-tert-butyl (3-fluoro-4-((4-fluorobenzyl)(prop-2-yn-1-yl)amino)-1,2-phenylene)dicarbamate (0.480 g, 0.985 mmole) was dissolved in dichloromethane (5 mL) and trifluoroacetic acid (5 mL) was added and the reaction was stirred at ambient temperature under argon for 90 min. The reaction was evaporated to give red oil which was dissolved in methanol (5 mL) and tetrahydrofuran (5 mL) and cooled in an ice bath when N, N-diisopropylethylamine (1.2 mL, 6.1 mmole) was added followed by ethyl chloroformate (129 mg, 1.2 mmole) dropwise. The reaction was stirred at ambient temperature for 18 h and was filtered and evaporated. The crude oil was dissolved in ethyl acetate (20 mL) and extracted with water (20 mL). The organic layer was then dried through a 1 PS filter and evaporated to dryness. It was chromatographed on a silica gel column (10 g) packed in chloroform. The column polarity was increased to 30% ethyl acetate in chloroform over 7 CV, at 12 mL/min. Fractions (22 mL each) containing the product were pooled and stripped to give ethyl (2-amino-3-fluoro-4-((4-fluorobenzyl)(prop-2-yn-1-yl)amino)phenyl)carbamate (0.073 g, 20% yield).

NMR Spectroscopy: $^1$H NMR (CDCl$_3$, 500 MHz): δ 7.41 (m, 2H), 7.12 (t, 2H), 6.88 (m, 1H), 6.61 (m, 1H), 6.22 (br s, 1H), 4.30 (s, 2H), 4.25 (m, 2H), 3.88 (s, 2H), 3.78 (s, 2H), 2.28 (s, 1H), 1.35 (t, 3H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 μL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd7}$=10.6 min.

Example 8—Compound 8

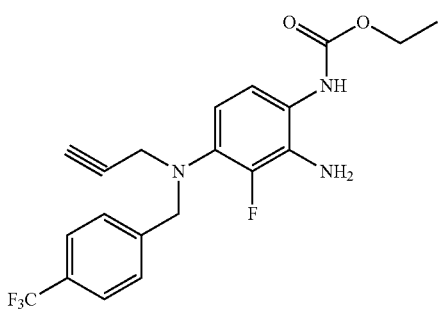

Step 1: Synthesis of N-(4-(trifluoromethyl)benzyl)prop-2-yn-1-amine 4-(Trifluoromethyl)benzylamine (6.93 g, 40 mmole) was dissolved in anhydrous acetonitrile (18 mL). Potassium carbonate (5.5 g, 40 mmole) was added and the mixture was cooled in an ice bath when 80% propargyl bromide in toluene (2.6 g, 20 mmole) was added over 10 min. The reaction was warmed to ambient temperature and stirred for 18 h. It was filtered and evaporated. The crude oil was dissolved in ethyl acetate (50 mL) and extracted with water (50 mL) and then brine (50 mL) and dried over sodium sulfate. It was chromatographed on a silica gel column (100g) packed in hexanes. The column polarity was increased to 100% ethyl acetate over 10 CV, at 50 mL/min. Fractions (22 mL each) containing the second band were pooled and stripped to give N-(4-(trifluoromethyl)benzyl)prop-2-yn-1-amine (3.0 g, 43% yield).

Step 2: Synthesis of 2-Fluoro-4-nitro-N$^1$-(prop-2-yn-1-yl)-N$^1$-(4-(trifluoromethyl)benzyl)benzene-1,3-diamine 2,3-Difluoro-6-nitroaniline (0.681 g, 3.91 mmole) was dissolved in anhydrous dimethylsulfoxide (5 mL). N-(4-(trifluoromethyl)benzyl)prop-2-yn-1-amine (1.75 g, 8.21 mmole)) was added followed by triethylamine (2.3 mL) and solid iodine (2 mg). The mixture was heated at reflux for 18 h. under argon. The reaction was dissolved in dichloromethane (10 mL) and extracted with water (10 mL). The aqueous layer was washed with 2×10 mL dichloromethane. The organic layers were combined and washed with brine (30 mL) and evaporated to dryness. The crude material was chromatographed on a silica gel column (25 g) packed in hexanes. The column polarity was increased to 100% chloroform over 20 CV, at 25 mL/min. Fractions (22 mL each) containing the product were pooled and stripped to give of 2-fluoro-4-nitro-N$^1$-(prop-2-yn-1-yl)-N$^1$-(4-(trifluoromethyl)benzyl)benzene-1,3-diamine (0.36 g, 25% yield).

Step 3: Synthesis of ethyl (2-amino-3-fluoro-4-(prop-2-yn-1-yl(4-(trifluoromethyl)benzyl)amino)phenyl)carbamate (Compound 8)

2-Fluoro-4-nitro-N$^1$-(prop-2-yn-1-yl)-N$^1$-(4-(trifluoromethyl)benzyl)benzene-1,3-diamine (0.350 g, 0.953 mmole) was dissolved in methanol (3 mL). Zinc powder (312 mg, 4.76 mmole) was added followed by ammonium chloride (255 mg, 4.76 mmole) in DI water (1.0 mL). The mixture was stirred under argon at ambient temperature for 18 h., and then zinc powder (312 mg, 4.76 mmole) were added followed by ammonium chloride (255 mg, 4.76 mmole) in DI water (1.0 mL). After 25 min., the mixture was cooled in an ice bath. N, N-diisopropylethylamine (0.364 mL, 2.01 mmole) was added, followed by ethyl chloroformate, dropwise (204 mg, 1.90 mmole) and the reaction was stirred at ambient temperature for 0.5 h. The reaction was dissolved in ethyl acetate (10 mL) and extracted with water (10 mL). The organic layer was dried through a 1 PS filter and evaporated to dryness. It was chromatographed on a silica gel column (50g) packed in chloroform. The column polarity was increased to 65% ethyl acetate/chloroform over 11 CV, at 50 mL/min. Fractions (22 mL each) containing the product were pooled and stripped to give ethyl (2-amino-3-fluoro-4-(prop-2-yn-1-yl(4-(trifluoromethyl)benzyl)amino)phenyl)-carbamate (0.087 g, 19% yield).

NMR Spectroscopy: $^1$H NMR (CDCl$_3$, 300 MHz): 7.59 (q, 4H), 6.95 (d, 1H), 6.62 (t, 1H), 6.24 (br s, 1H), 4.40 (s, 2H), 4.24 (q, 2H), 3.80 (d, 2H), 2.05-2.50 (m, 2H), 1.38 (t, 3H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 μL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd8}$=12.3 min.

Example 9: Compound 9

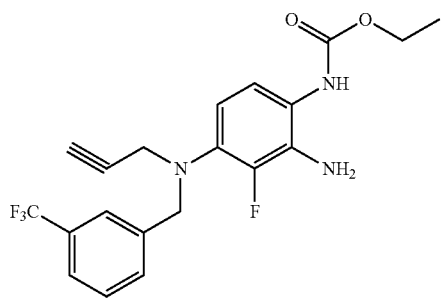 [SMILES: C#CCN(Cc1cccc(C(F)(F)F)c1)c1ccc(NC(=O)OCC)c(N)c1F]

Step 1: Synthesis of N-(3-(trifluoromethyl)benzyl)prop-2-yn-1-amine 3-(Trifluoromethyl)benzylamine (5.0 g, 28.6 mmole) was dissolved in anhydrous acetonitrile (18 mL). Potassium carbonate (4.00 g, 28.6 mmole) was added and the mixture was cooled in an ice bath when 80% propargyl bromide in toluene (3.0 mL, 19 mmole) was added over 30 min. The reaction was warmed to ambient temperature and stirred for 2 h. It was filtered and evaporated. It was chromatographed on a silica gel column (50 g) packed in hexanes. The column polarity was increased to 100% ethyl acetate over 9 CV, at 50 mL/min. Fractions (22 mL each) containing the second band were pooled and stripped to give N-(3-(trifluoromethyl)benzyl)prop-2-yn-1-amine (2.72 g, 45% yield).

Step 2: Synthesis of 2-Fluoro-4-nitro-N$^1$-(prop-2-yn-1-yl)-N$^1$-(3-(trifluoromethyl)benzyl)benzene-1,3-diamine 2,3-Difluoro-6-nitroaniline (1.09 g, 6.26 mmole) was dissolved in anhydrous dimethylsulfoxide (8 mL). N-(3-(trifluoromethyl)benzyl)prop-2-yn-1-amine (2.00 g, 9.39 mmole) was added triethylamine (2.86 mL) and solid iodine (1 mg). The mixture was heated at reflux for 23 h. under argon. The reaction was dissolved in ethyl acetate (40 mL) and extracted with water (40 mL). The aqueous layer was washed with ethyl acetate (20 mL). The organic layers were washed with water, 2×20 mL brine and filtered through a 1 PS filter to dry. The crude material was chromatographed on a silica gel column (50 g) packed in hexanes. The column polarity was increased to 40% ethyl acetate over 15 CV, at 50 mL/min. Fractions (22 mL each) containing the product were pooled and stripped to give 2-fluoro-4-nitro-N$^1$-(prop-2-yn-1-yl)-N$^1$-(3-(trifluoromethyl)benzyl)benzene-1,3-diamine (0.393 g, 17% yield).

Step 3: Synthesis of ethyl (2-amino-3-fluoro-4-(prop-2-yn-1-yl(3-(trifluoromethyl)benzyl)amino)phenyl)carbamate (Compound 9)

2-Fluoro-4-nitro-N$^1$-(prop-2-yn-1-yl)-N$^1$-(3-(trifluoromethyl)benzyl)benzene-1,3-diamine (0.380 g, 1.04 mmole) was dissolved in methanol (6 mL) and tetrahydrofuran (6 mL). Zinc powder (0.677 g, 10.4 mmole) was added followed by ammonium chloride (553 mg, 10.35 mmole) in DI water (2 mL). The mixture was stirred under argon at ambient temperature for 30 min. The reaction was cooled in an ice bath and N, N-diisopropylethylamine (0.515 mL, 2.96 mmole) was added followed by ethyl chloroformate (249 mg, 2.33 mmole) dropwise. The reaction was stirred at ambient temperature for 18 h and was filtered and evaporated. The crude oil was dissolved in ethyl acetate (20 mL) and extracted with water (20 mL). the organic layer was then dried through a 1 PS filter and evaporated to dryness. It was chromatographed on a silica gel column (10 g) packed in chloroform. The column polarity was increased to 20% ethyl acetate in chloroform over 7 CV, at 12 mL/min. Fractions (22 mL each) containing the product were pooled and stripped to give of ethyl (2-amino-3-fluoro-4-(prop-2-yn-1-yl(3-(trifluoromethyl)benzyl)amino)phenyl)carbamate (0.249 g, 58% yield).

NMR Spectroscopy: $^1$H NMR (CDCl$_3$, 500 MHz): δ 7.39-7.70 (m, 5H), 6.90 (d, 1H), 6.59 (t, 1H), 6.23 (br s, 1H), 4.35 (s, 2H), 4.19 (m, 2H), 3.56-3.92 (m, 3H), 2.25 (s, 1H), 1.25 (t, 3H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 µL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd9}$=12.0 min.

Example 10: Compound 11

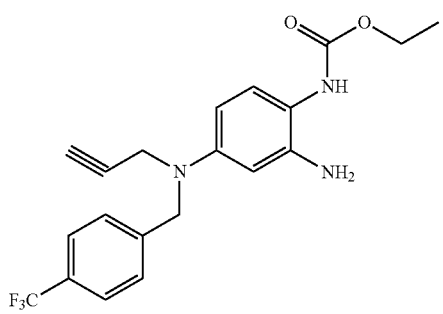 [SMILES: C#CCN(Cc1ccc(C(F)(F)F)cc1)c1ccc(NC(=O)OCC)c(N)c1]

Step 1: Synthesis of 4-Nitro-N$^1$-(4-(trifluoromethyl)benzyl)benzene-1,3-diamine 5-Fluoro-2-nitroaniline (10.24 g, 58.46 mmole) was dissolved in anhydrous dimethylsulfoxide (90 mL). (4-(trifluoromethyl)phenyl)methanamine (6.1 g, 39.0 mmole) was added followed by triethylamine (13.0 mL) and solid iodine (70 mg). The mixture was heated at reflux for 1 h. under argon. Ethyl acetate (150 mL) was added and the organics were extracted with water (3×150 mL). The combined aqueous layers were washed with dichloromethane (300 mL), all organics were combined, filtered through a 1 PS filter and then evaporated to dryness. The crude material was dissolved in boiling ethyl acetate (20 mL) and hexanes were added to cloud point. Upon cooling, crystals formed. The solid was filtered off on a #54 Whatman filter paper on a Buchner filter and dried under high vacuum to give 4-nitro-M-(4-(trifluoromethyl)benzyl)benzene-1,3-diamine (8.61 g, 71% yield).

Step 2: Synthesis of di-tert-butyl (4-((4-(trifluoromethyl)benzyl)amino)-1,2-phenylene)dicarbamate 4-Nitro-M-(4-(trifluoromethyl)benzyl)benzene-1,3-diamine (8.17 g, 26.2 mmole) was dissolved in methanol (30 mL) and tetrahydrofuran (30 mL). The mixture was cooled in an ice bath and zinc powder (17.16 g, 262.5 mmole) was added followed by ammonium chloride (14.0 g, 262.5 mmole) in DI water (40 mL) over 60 min. The reaction was filtered on a celite pad and solids were washed with methanol (200 mL) and the filtrate was evaporated to dryness. Ethyl acetate (100 mL) was added and the mixture was extracted with water (100 mL) and then brine (50 mL) The organic layer was evaporated to dryness. The residue was dissolved in tetrahydrofuran (171 mL) and di-tert-butyldicarbonate (8.60 g, 39.36 mmole) was added followed by solid sodium bicarbonate (6.60 g, 78.75 mmole) and then DI water (86 mL). The reaction was stirred for an 18 h. at ambient temperature. The reaction was filtered and evaporated to dryness. Ethyl acetate (200 mL) was added and then washed with 3M NH$_4$OH (2×200 mL). The organic layer was evaporated to dryness. It was chromatographed on a silica gel column (100 g) packed in hexane. The column polarity was increased to 60% ethyl acetate in hexanes over 14 CV. Flow rate at 50 mL/min. Fractions (22 mL each)

containing the product were pooled and stripped to give di-tert-butyl (4-((4-(trifluoromethyl)benzyl)amino)-1,2-phenylene)dicarbamate (5.9 g, 47% yield).

Step 3: Synthesis of di-tert-butyl (4-(prop-2-yn-1-yl (4-(trifluoromethyl)benzyl)amino)-1,2-phenylene) dicarbamate Di-tert-butyl (4-((4-(trifluoromethyl)benzyl)amino)-1,2-phenylene)dicarbamate (4.88 g, 10.13 mmole) was dissolved in anhydrous dimethylformamide (50 mL). 80% propargyl bromide in toluene (2.50 mL, 23.3 mmole) was added followed by diisopropylethylamine (5.30 mL, 30.4 mmole). The mixture was heated at reflux, under argon, for 2h. The reaction was evaporated to dryness and the crude material was chromatographed on a suction silica gel column (50 g) packed in hexanes. The column was washed with hexanes (250 mL), 10% ethyl acetate in hexanes (250 mL), 10% ethyl acetate in hexanes (250 mL), 20% ethyl acetate in hexanes (250 mL), 30% ethyl acetate in hexanes (500 mL), Fractions (125 mL each) containing the product were pooled and stripped to give di-tert-butyl (4-(prop-2-yn-1-yl (4-(trifluoromethyl)benzyl)-amino)-1,2-phenylene)dicarbamate (1.42 g, 27% yield).

Step 4: Synthesis of ethyl (2-amino-4-(prop-2-yn-1-yl(4-(trifluoromethyl)benzyl)amino)phenyl)carbamate (Compound 11)

Di-tert-butyl (4-(prop-2-yn-1-yl(4-(trifluoromethyl)benzyl)amino)-1,2-phenylene)dicarbamate (1.40 g, 2.69 mmole) was dissolved in dichloromethane (15 mL) and trifluoroacetic acid (15 mL) was added and the reaction was stirred at ambient temperature under argon for 45 min. The organic layer was evaporated to dryness, dissolved in methanol (10 mL) and tetrahydrofuran (10 mL) and cooled in an ice bath when N, N-diisopropylethylamine (3.00 mL, 16.7 mmole) was added followed by ethyl chloroformate (0.317 g, 2.63 mmole) dropwise. The reaction was stirred at ambient temperature for 1 h and was evaporated. The crude oil was dissolved in ethyl acetate (40 mL) and extracted with water (40 mL). The organic layer was then dried through a 1 PS filter and evaporated to dryness. It was chromatographed on a silica gel column (25 g) packed in hexanes. The column polarity was increased to 33% ethyl acetate over 7CV, held at 33% ethyl acetate over 4 CV and then increased to 84% ethyl acetate over 10 CV. Flow rate at 25 mL/min. Fractions (22 mL each) containing the product were pooled and stripped to give ethyl (2-amino-4-(prop-2-yn-1-yl(4-(trifluoromethyl)benzyl)amino)phenyl)carbamate (0.462 g, 44% yield).

NMR Spectroscopy: $^1$H NMR (CDCl$_3$, 500 MHz): δ 7.55 (d, 2H), 7.40 (d, 2H), 6.98 (d, 1H), 6.20-6.25 (m, 2H), 6.07 (br s, 1H), 4.53 (s, 2H), 4.18 (q, 2H), 3.95 (s, 2H), 3.78 (br s, 2H), 2.21 (s, 1H), 1.25 (t, 3H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 μL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd11}$=8.8 min.

Example 11: Compound 12

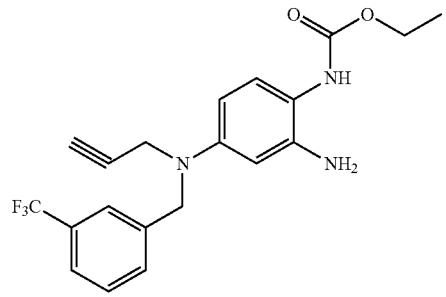 [SMILES: C#CCN(Cc1cccc(C(F)(F)F)c1)c1ccc(NC(=O)OCC)c(N)c1]

Step 1: Synthesis of 4-Nitro-N$^1$-(3-(trifluoromethyl) benzyl)benzene-1,3-diamine 5-Fluoro-2-nitroaniline (10.24 g, 58.46 mmole) was dissolved in anhydrous dimethylsulfoxide (90 mL). 3-fluorobenzylamine (6.1 g, 39.0 mmole) was added triethylamine (13.0 mL) and solid iodine (90 mg) were added and the mixture was heated at reflux for 4 h. under argon. The reaction was dissolved in ethyl acetate (200 mL) and extracted with water (3×200 mL). The combined aqueous layers were washed with (300 mL) ethyl acetate, combined and then evaporated to dryness. The crude material was triturated with hexane/ethyl acetate (7:3, 100 mL) and dried under high vacuum to give 4-nitro-N$^1$-(3-(trifluoromethyl) benzyl)benzene-1,3-diamine (8.29 g, 77% yield).

Step 2: Synthesis of di-tert-butyl (4-((tert-butoxycarbonyl)(3-(trifluoromethyl)benzyl)amino)-1,2-phenylene)dicarbamate 4-Nitro-N$^1$-(3-(trifluoromethyl)benzyl)benzene-1,3-diamine (10.8 g, 34.7 mmole) was dissolved in methanol (50 mL) and tetrahydrofuran (50 mL). Zinc powder (22.7 g, 347 mmole) was added followed by ammonium chloride (18.6 g, 347 mmole) in DI water (46 mL) over 30 min. The mixture was stirred under argon at ambient temperature for 30 min. The reaction was filtered on a celite pad which was washed with methanol (200 mL) and the mixture was evaporated to dryness. Ethyl acetate (200 mL) was added and the mixture was extracted with water (200 mL) and brine (50 mL) and evaporated to dryness. The residue was dissolved in tetrahydrofuran (150 mL) and di-tert-butyldicarbonate (22.1 g, 101.3 mmole) was added followed by solid sodium bicarbonate (11.63 g, 138.4 mmole) and then DI water (100 mL). The reaction was stirred for an 18 h. at ambient temperature. The reaction was evaporated to dryness. and ethyl acetate (200 mL) was added. The organic layer was extracted with water (3×200 mL) and brine (50 mL) and evaporated to dryness. It was chromatographed on a silica gel column (200 g) packed in hexane. The column polarity was increased to 35% ethyl acetate in hexanes over 9 CV, at 100 mL/min. Fractions (22 mL each) containing the product were pooled and stripped to give di-tert-butyl (4-((tert-butoxycarbonyl) (3-(trifluoromethyl)benzyl)amino)-1,2-phenylene)dicarbamate (13.1 g, 65% yield).

Step 3: Synthesis of di-tert-butyl (4-((3-(trifluoromethyl)benzyl)amino)-1,2-phenylene)dicarbamate Di-tert-butyl (4-((tert-butoxycarbonyl)(3-(trifluoromethyl)benzyl)amino)-1,2-phenylene)dicarbamate (13.0 g, 22.4 mmole) was dissolved in dichloromethane (75 mL) and trifluoroacetic acid (50 mL) was added and the reaction was stirred at ambient temperature under argon for 60 min. The reaction was evaporated to give an off-white solid. The solid was dissolved in dioxane (125 mL) and di-tert-butyldicarbonate (10.24 g, 46.94 mmole) was added followed by solid sodium bicarbonate (7.51 g, 89.4 mmole) and then DI water (50 mL). The reaction was heated to 40° C. with stirring for 18 h., under argon. The reaction was evaporated and ethyl acetate (200 mL) was added. The organic layer was extracted with 3M NH$_4$OH (2×100 mL) and brine (50 mL), dried through a 1 PS filter and evaporated to dryness. It was chromatographed on a silica gel column (200 g) packed in hexane. The column polarity was increased to 45% ethyl acetate in hexanes over 12 CV, at 100 mL/min. Fractions (22 mL each) containing the product were pooled and stripped to give di-tert-butyl (4-((3-(trifluoromethyl)benzyl)amino)-1,2-phenylene)dicarbamate (1.3 g, 65% yield).

Step 4: Synthesis of Di-tert-butyl (4-(prop-2-yn-1-yl(3-(trifluoromethyl)benzyl)amino)-1,2-phenylene) dicarbamate Di-tert-butyl (4-((3-(trifluoromethyl)benzyl)amino)-1,2-phenylene)dicarbamate (2.00 g, 4.15 mmole) was dissolved in anhydrous dimethylformamide (20 mL). Diisopropylethylamine (2.20 mL, 12.5 mmole) was added followed by 80% propargyl bromide in toluene (1.50 mL, 14.3 mmole). The mixture was heated in a 110° C. oil bath under argon for 2h. The reaction was diluted in ethyl acetate (200 mL) and extracted with water (200 mL). The organic layer was evaporated to dryness. The crude material was chromatographed on a silica gel column (25 g) packed in hexanes. The column polarity was increased to 40% ethyl acetate over 15 CV, at 25 mL/min. Fractions (22 mL each) containing the product were pooled and stripped to give di-tert-butyl (4-(prop-2-yn-1-yl(3-(trifluoromethyl)benzyl)amino)-1,2-phenylene)dicarbamate (1.76 g, 82% yield).

Step 5: Synthesis of ethyl (2-amino-4-(prop-2-yn-1-yl(3-(trifluoromethyl)benzyl)amino) phenyl)carbamate (Compound 12)

Di-tert-butyl (4-(prop-2-yn-1-yl (3-(trifluoromethyl)benzyl)amino)-1,2-phenylene)dicarbamate (1.0 g, 1.9 mmole) was dissolved in dichloromethane (7 mL) and trifluoroacetic acid (7 mL) was added and the reaction was stirred at ambient temperature under argon for 90 min. The organic layer was evaporated to dryness, dissolved in methanol (5 mL) and tetrahydrofuran (5 mL) and cooled in an ice bath when N, N-diisopropylethylamine (2.1 mL, 11.9 mmole) was added followed by ethyl chloroformate (0.225 mL, 2.11 mmole) dropwise. The reaction was stirred at ambient temperature for 18 h and was filtered and evaporated. The crude oil was dissolved in ethyl acetate (20 mL) and extracted with water (20 mL). The organic layer was then dried through a 1 PS filter and evaporated to dryness. It was chromatographed on a silica gel column (25 g) packed in hexane. The column polarity was increased to 33% ethyl acetate over 4 CV, held at 33% ethyl acetate over 4 CV and then increased to 100% ethyl acetate over 13 CV. Flow rate at 25 mL/min. Fractions (22 mL each) containing the product were pooled and stripped to give ethyl (2-amino-4-(prop-2-yn-1-yl(3-(trifluoromethyl)benzyl)amino)phenyl)-carbamate (0.360 g, 48% yield).

NMR Spectroscopy: $^1$H NMR (CDCl$_3$, 500 MHz): δ 7.60 (s, 1H), 7.50 (m, 2H), 7.40-7.45 (m, 1H), 7.24 (s, 1H), 7.00 (t, 1H), 6.30 (d, 1H), 6.23 (s, 1H), 6.02 (br s, 1H), 4.60 (s, 2H), 4.2 (q, 2H), 3.87 (s, 2H), 2.30 (br s, H), 2.21 (s, 1H), 1.24 (t, 3H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 µL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd12}$=8.3 min.

Example 12: Compound 13

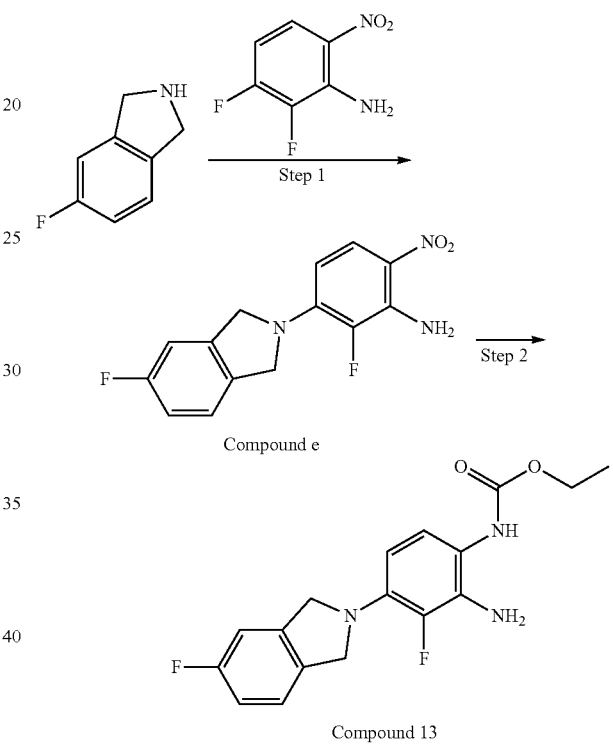

Compound 13

Step 1: Synthesis of Compound e

To a stirred suspension of 2, 3-difluoro-6-nitroaniline (1 equiv) in dry DMSO is added 5-fluoroisoindoline (3 equiv) followed by Et$_3$N (1.2 equiv) and 12 (catalytic amount). The reaction mixture is heated to 120° C. and stirred at 120° C. for 24 h. Upon complete consumption of the starting material (as determined by TLC), the reaction mixture is cooled to RT, diluted with water (25 mL), and extracted with EtOAc (2×25 mL). The combined organic layers are dried over anhydrous Na$_2$SO$_4$, filtered, and concentrated under reduced pressure to give a crude product, which is purified by silica gel column chromatography to afford Compound e.

Step 2: Synthesis of Compound 13

To a stirred solution of Compound e (1 equiv) in methanol is added zinc powder (5 equiv) followed by the dropwise addition of ammonium chloride solution (5 equiv). After stirring at RT for 5 hours, DIPEA (1.25 equiv) and ethyl chloroformate (1 equiv) are then added to reaction mixture at 10° C., and the stirring is continued for another 3 hours at RT. Upon complete consumption of the starting material (as determined by TLC), the reaction mixture is diluted with water and stirred for 1 hour to give a solid product. The obtained solid is filtered, dissolved in EtOAc, and any un-dissolved solid is removed by filtration. The filtrate concentrated to provide Compound 13 which is crystallized using n-hexane.

Example 13: Compound 13

Step 1: Synthesis of 2-Fluoro-3-(5-fluoroisoindolin-2-yl)-6-nitroaniline 2,3-Difluoro-6-nitroaniline (0.311 g, 1.78 mmole) was dissolved in anhydrous dimethylsulfoxide (6 mL). 5-fluoroisoindoline hydrochloride (0.465 g, 2.68 mmole) was added triethylamine (0.814 mL) and solid iodine (1 mg). The mixture was heated at reflux for 4 h. under argon. The reaction was slurried in 7:3 chloroform/isopropanol (5 mL) and filtered on a #54 Whatman filter on a buchner funnel. The solid was washed with 7:3 chloroform/isopropanol (2×5 mL) and dried at ambient temp. under high vacuum to give a white solid 2-fluoro-3-(5-fluoroisoindolin-2-yl)-6-nitroaniline (0.455 g, 88% yield).

Step 2: Synthesis of Ethyl (2-amino-3-fluoro-4-(5-fluoroisoindolin-2-yl)phenyl)carbamate (Compound 13)

2-Fluoro-3-(5-fluoroisoindolin-2-yl)-6-nitroaniline (0.440 g, 1.51 mmole) was dissolved in methanol (5 mL) and tetrahydrofuran (5 mL). Zinc powder (0.988 g, 15.1 mmole) was added followed by ammonium chloride (808 mg, 15.1 mmole) in DI water (2 mL). The mixture was stirred under argon at ambient temperature for 45 min. The reaction was cooled in an ice bath and N, N-diisopropylethylamine (0.604 mL, 3.45 mmole) was added followed by ethyl chloroformate (291 mg, 2.72 mmole) dropwise. The reaction was stirred at ambient temperature for 12 h. The reaction was cooled in an ice bath and N, N-diisopropylethylamine (0.300 mL, 1.74 mmole) was added followed by ethyl chloroformate (150 mg, 1.30 mmole) dropwise. The reaction was stirred at ambient temperature for 2 h and was filtered and evaporated. The crude oil was dissolved in ethyl acetate (10 mL) and extracted with water (10 mL). the organic layer was then dried through a 1 PS filter and evaporated to dryness. It was chromatographed on a silica gel column (10 g) packed in chloroform. The column polarity was increased to 45% ethyl acetate in chloroform over 14 CV, at 12 mL/min. Fractions (22 mL each) containing the product were pooled and stripped to give ethyl (2-amino-3-fluoro-4-(5-fluoroisoindolin-2-yl)phenyl)carbamate (0.033 g, 6.3% yield).

NMR Spectroscopy: $^1$H NMR (CD$_3$OD, 500 MHz): δ 7.30 (m, 1H), 7.05 (d, 1H), 6.98 (m, 1H), 6.80 (s, 1H), 6.20 (m, 1H), 4.68 (m, 4H), 4.18 (m, 2H), 1.25 (s, 4H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 µL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd13}$=10.1 min.

Example 14a: Compound 14

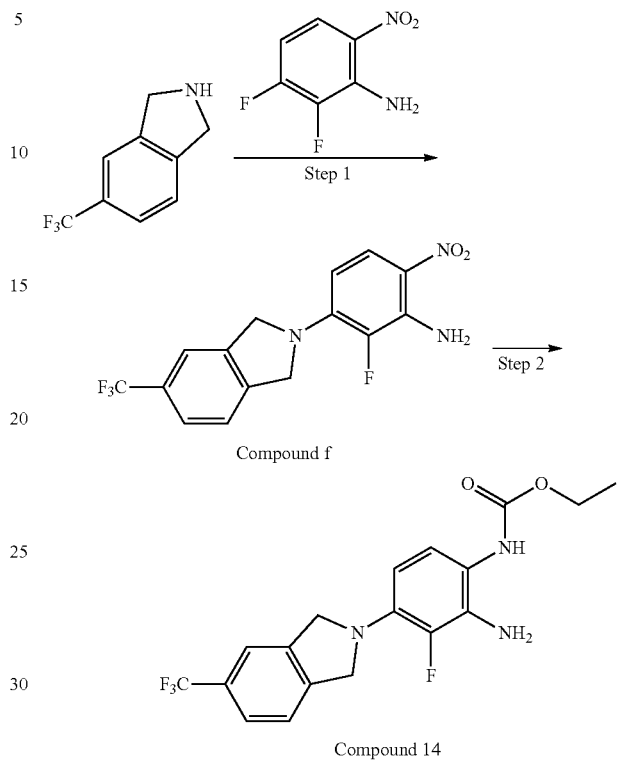

Compound f

Compound 14

Step 1: Synthesis of Compound f

To a stirred suspension of 2, 3-difluoro-6-nitroaniline (1 equiv) in dry DMSO is added 5-trifluoromethylisoindoline (3 equiv) followed by Et$_3$N (1.2 equiv) and I$_2$ (catalytic amount). The reaction mixture is heated to 120° C. and stirred at 120° C. for 24 hours. Upon complete consumption of the starting material (as determined by TLC), the reaction mixture is diluted with water (25 mL), and extracted with EtOAc (2×25 mL). The combined organic layers are dried over anhydrous Na$_2$SO$_4$, filtered, and concentrated under reduced pressure to give a crude product, which is purified by silica gel column chromatography to afford Compound f.

Step 2: Synthesis of Compound 14

To a stirred solution of Compound f (1 equiv) in methanol is added zinc powder (5 equiv) followed by the dropwise addition of ammonium chloride solution (5 equiv). After stirring at RT for 5 hours, DIPEA (1.25 equiv) and ethyl chloroformate (1 equiv) are added to reaction mixture at 10° C., and the stirring is continued for another 3 hours at RT. Upon complete consumption of the starting material (as determined by TLC), the reaction mixture is diluted with water and stirred for 1 hour to give a solid product. The obtained solid is filtered, dissolved in EtOAc, and any un-dissolved solid is removed by filtration. The filtrate is concentrated to provide Compound 14 which is crystallized using n-hexane.

Example 14b: Compound 14

Step 1: Synthesis of 2-Fluoro-6-nitro-3-(5-(trifluoromethyl)isoindolin-2-yl)aniline 2,3-Difluoro-6-nitroaniline (0.233 g, 1.34 mmole) was dissolved in anhydrous dimethylsulfoxide (6 mL). 5-(trifluoromethyl)isoindoline hydrochloride (0.448 g, 2.00 mmole) was added triethylamine (0.61 mL) and solid iodine (1 mg). The mixture was heated at reflux for 2 h. under argon. The reaction was dissolved in dichloromethane (10 mL) and extracted with water (10 mL). The aqueous layer was washed with dichloromethane (10 mL), organics pooled and washed with brine (5 mL) and then dried through a 1 PS filter and evaporated to dryness. The crude material was chromatographed on a silica gel column (10 g) packed in hexane. The column polarity was increased to 100% ethyl acetate over 12 CV, at 12 mL/min. Fractions (22 mL each) containing the product were pooled and stripped to give 2-fluoro-6-nitro-3-(5-(trifluoromethyl)-isoindolin-2-yl)aniline (0.480 g, 100% yield).

Step 2: Synthesis of ethyl (2-amino-3-fluoro-4-(5-(trifluoromethyl)isoindolin-2-yl)phenyl)carbamate (Compound 14)

2-Fluoro-6-nitro-3-(5-(trifluoromethyl)isoindolin-2-yl) aniline (0.470 g, 1.378 mmole) was dissolved in methanol (5 mL) and tetrahydrofuran (5 mL). Zinc powder (0.900 g, 13.78 mmole) was added followed by ammonium chloride (737 mg, 13.78 mmole) in DI water (2 mL). The mixture was stirred under argon at ambient temperature for 45 min. and then cooled in an ice bath. Triethylamine (0.55 mL, 3.96 mmole) was added, followed by ethyl chloroformate dropwise (265 mg, 2.48 mmole) and the reaction was stirred at ambient temperature for 105 min. The reaction was filtered and evaporated. The crude oil was dissolved in ethyl acetate (10 mL) and extracted with water (10 mL). the organic layer was then dried through a 1 PS filter and evaporated to dryness. It was chromatographed on a silica gel column (10 g) packed in chloroform. The column was washed with 13 CV of chloroform and then polarity was increased to 45% ethyl acetate/chloroform over 14 CV, at 12 mL/min. Fractions (22 mL each) containing the product were pooled and stripped to give ethyl (2-amino-3-fluoro-4-(5-(trifluoromethyl)isoindolin-2-yl)phenyl)carbamate (0.146 g, 28% yield).

NMR Spectroscopy: $^1$H NMR (DMSO, 300 MHz): δ 8.50 (br s, 1H), 7.78 (s, 1H), 7.63 (q, 3H), 6.82 (d, 1H), 6.10 (t, 1H), 4.75 (s, 5H), 4.08 (q, 2H), 1.20 (t, 3H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 μL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd14}$=11.8 min.

Example 15: Compound 15

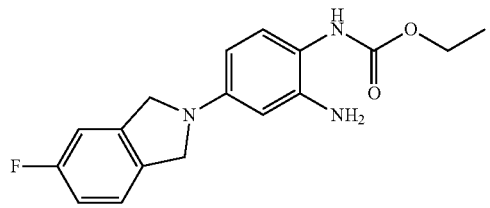 [SMILES: CCOC(=O)Nc1ccc(N2Cc3ccc(F)cc3C2)cc1N]

5-(5-Fluoroisoindolin-2-yl)-2-nitroaniline (0.334 g, 1.22 mmole) was dissolved in methanol (5 mL) and tetrahydrofuran (5 mL). Zinc powder (0.800 g, 12.23 mmole) was added followed by ammonium chloride (654 mg, 12.23 mmole) in DI water (2 mL). The mixture was stirred under argon at ambient temperature for 2 h. The reaction was cooled in an ice bath and N, N-diisopropylethylamine (0.489 mL, 2.81 mmole) was added followed by ethyl chloroformate (235 mg, 2.20 mmole) dropwise. The reaction was stirred at ambient temperature for 60 min. and was filtered and evaporated. The crude oil was dissolved in ethyl acetate (10 mL) and extracted with water (10 mL). the organic layer was then dried through a 1 PS filter and evaporated to dryness. It was chromatographed on a silica gel column (10 g) packed in hexanes. The column polarity was increased to 100% ethyl acetate over 20 CV, at 12 mL/min. Fractions (22 mL each) containing the product were pooled and stripped to give ethyl (2-amino-4-(5-fluoroisoindolin-2-yl)phenyl) carbamate (0.130 g, 34% yield).

NMR Spectroscopy: $^1$H NMR (CDCl$_3$, 500 MHz): δ 7.28 (m, 1H), 7.03 (m, 3H), 6.10 (d, 3H), 4.60 (m, 4H), 4.21 (m, 2H), 3.98 (br s, 2H), 1.32 (s, 3H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 μL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd15}$=6.5 min.

Example 16: Compound 16

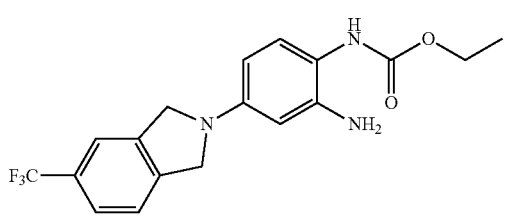 [SMILES: CCOC(=O)Nc1ccc(N2Cc3ccc(C(F)(F)F)cc3C2)cc1N]

Step 1: Synthesis of 2-Nitro-5-(5-(trifluoromethyl) isoindolin-2-yl)aniline 5-Fluoro-2-nitroaniline (0.237 g, 1.52 mmole) was dissolved in anhydrous dimethylsulfoxide (6 mL). 5-(trifluoromethyl)isoindoline hydrochloride (0.510 g, 2.28 mmole) was added triethylamine (0.72 mL) and solid iodine (1 mg). The mixture was heated at reflux for 12 h. under argon. The reaction was dissolved in dichloromethane (10 mL) and extracted with water (10 mL). The reaction was dissolved in dichloromethane (10 mL) and extracted with water (10 mL). The organic layer was washed with 3×30 mL water and then dried through a 1 PS filter and evaporated to dryness. The crude material was chromatographed on a silica gel column (10 g) packed in hexanes. The column polarity was increased to 100% ethyl acetate over 10 CV, at 12 mL/min. Fractions (22 mL each) containing the product were pooled and stripped to give of 2-nitro-5-(5-(trifluoromethyl)isoindolin-2-yl)aniline (0.225 g, 46% yield).

Step 2: Synthesis of ethyl (2-amino-4-(5-(trifluoromethyl)isoindolin-2-yl)phenyl)carbamate (Compound 16)

2-Nitro-5-(5-(trifluoromethyl)isoindolin-2-yl)aniline (0.252 g, 0.779 mmole) was dissolved in methanol (5 mL) and tetrahydrofuran (5 mL). Zinc powder (0.509 g, 7.79 mmole) was added followed by ammonium chloride (417 mg, 7.79 mmole) in DI water (2 mL). The mixture was stirred under argon at ambient temperature for 45 min triethylamine (0.55 mL, 3.96 mmole) was added, and the reaction was cooled in an ice bath. Ethyl chloroformate was added dropwise (150 mg, 1.40 mmole) and the reaction was stirred at ambient temperature for 2 h. The reaction was filtered and evaporated. The crude oil was dissolved in ethyl acetate (10 mL) and extracted with water (10 mL). the organic layer was then dried through a 1 PS filter and evaporated to dryness. It was chromatographed on a silica gel column (10 g) packed in chloroform. The column was washed with 12 CV of chloroform and then polarity was increased to 50% ethyl acetate/chloroform over 20 CV, at 12 mL/min. Fractions (22 mL each) containing the product were pooled and stripped to give ethyl (2-amino-4-(5-(trifluoromethyl)isoindolin-2-yl)phenyl)carbamate (0.113 g, 40% yield).

NMR Spectroscopy: $^1$H NMR (DMSO, 500 MHz): δ 8.28 (br s, 1H), 7.80 (m, 1H), 7.60-7.75 (m, 3H), 6.97 (s, 1H), 6.03 (s, 1H), 5.95 (m, 1H), 4.98 (d, 1H), 4.75 (s, 2H), 4.70 (s, 1H), 4.60 (s, 1H), 4.08 (q, 2H), 1.22 (s, 3H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 μL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd16}$=8.3 min.

Example 17: Compound 17

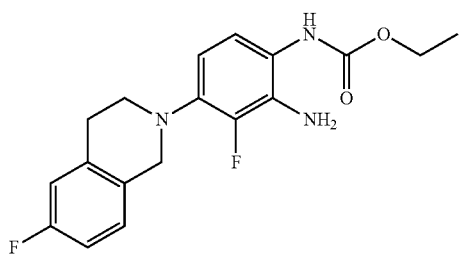 [SMILES: CCOC(=O)Nc1ccc(N2CCc3cc(F)ccc3C2)c(F)c1N]

Step 1: Synthesis of 2-Fluoro-3-(6-fluoro-3,4-dihydroisoquinolin-2(1H)-yl)-6-nitroaniline 2,3-Difluoro-6-nitroaniline (0.31 g, 1.8 mmole) was dissolved in anhydrous dimethylsulfoxide (3 mL). 6-fluoro-1, 2,3,4-tetrahydroisoquinoline hydrochloride (0.50 g, 2.7 mmole) was added followed by triethylamine (0.84 mL) and solid iodine (1 mg). The mixture was heated at reflux for 3 h. under argon. The reaction was dissolved in ethyl acetate (50 mL) and extracted with water (50 mL). The aqueous layer was extracted with 2×25 mL chloroform/isopropanol (7:3). The organic layers were washed with 3×25 mL water and then brine (50 mL) and dried over sodium sulfate. The oily solid was chromatographed on a silica gel column (25 g) packed in hexanes. The column polarity was increased to 50% ethyl acetate/hexanes over 8 CV, at 25 mL/min. Fractions (22 mL each) containing the product were pooled and stripped to give 2-fluoro-3-(6-fluoro-3,4-dihydroisoquinolin-2(1H)-yl)-6-nitroaniline (0.4 g, 74% yield).

Step 2: Synthesis of ethyl (2-amino-3-fluoro-4-(6-fluoro-3,4-dihydroisoquinolin-2(1H)-yl)phenyl)carbamate (Compound 17)

2-Fluoro-3-(6-fluoro-3,4-dihydroisoquinolin-2(1H)-yl)-6-nitroaniline (0.388 g, 1.27 mmole) was dissolved in methanol (10 mL) and tetrahydrofuran (10 mL). Zinc powder (415 mg, 6.35 mmole) was added followed by ammonium chloride (340 mg, 6.35 mmole) in DI water (1 mL). The mixture was stirred under argon at ambient temperature for 2 h. and then cooled to 10° C. in an ice bath. N, N-diisopropylethylamine (0.565 mL, 3.24 mmole) was added, followed by ethyl chloroformate dropwise (406 mg, 3.80 mmole) and the reaction was stirred at ambient temperature for 18 h. It was filtered and evaporated. The crude oil was dissolved in dichloromethane (10 mL) and extracted with water (10 mL). The aqueous layer was extracted with additional dichloromethane (3×10 mL), the organic layers were pooled and evaporated to dryness. It was chromatographed on a silica gel column (25g) packed in chloroform. The column polarity was increased to 20% ethyl acetate/chloroform over 11 CV, at 25 mL/min. Fractions (22 mL each) containing the product were pooled and stripped to give ethyl (2-amino-3-fluoro-4-(6-fluoro-3,4-dihydroisoquinolin-2(1H)-yl)phenyl)carbamate (0.225 g, 51% yield).

NMR Spectroscopy: $^1$H NMR (CDCl$_3$, 300 MHz): δ 7.05 (m, 1H), 6.80-7.00 (m, 3H), 6.47 (t, 1H), 6.25 (br s, 1H), 4.25 (m, 4H), 3.52-4.15 (br s, 2H), 3.40 (m, 2H), 2.98 (m, 2H), 1.30 (t, 3H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 μL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd17}$=8.4 min.

Example 18: Compound 18

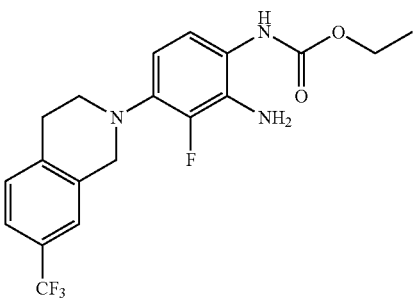 [SMILES: CCOC(=O)Nc1ccc(N2CCc3ccc(C(F)(F)F)cc3C2)c(F)c1N]

Step 1: Synthesis of 2-Fluoro-6-nitro-3-(7-(trifluoromethyl)-3,4-dihydroisoquinolin-2(1H)-yl)aniline 2,3-Difluoro-6-nitroaniline (0.238 g, 1.37 mmole) was dissolved in anhydrous dimethylsulfoxide (6 mL). 7-(trifluoromethyl)-1,2,3,4-tetrahydroisoquinoline hydrochloride (0.487 g, 2.05 mmole) was added triethylamine (0.643 mL) and solid iodine (1 mg). The mixture was heated at reflux for 12 h. under argon. The reaction was dissolved in dichloromethane (10 mL) and extracted with water (10 mL). The aqueous layer was washed with dichloromethane (10 mL), organics pooled and washed with brine (5 mL) and then dried through a 1 PS filter and evaporated to dryness. The crude material was chromatographed on a silica gel column (10 g) packed in hexanes. The column polarity was increased to 100% ethyl acetate over 12 CV, at 12 mL/min. Fractions (22 mL each) containing the product were pooled and stripped to give 2-fluoro-6-nitro-3-(7-(trifluoromethyl)-3,4-dihydroisoquinolin-2(1H)-yl)aniline (0.388 g, 80% yield).

Step 2: Synthesis of Ethyl (2-amino-3-fluoro-4-(7-(trifluoromethyl)-3,4-dihydroisoquinolin-2(1H)-yl)phenyl)carbamate (Compound 18)

2-Fluoro-6-nitro-3-(7-(trifluoromethyl)-3,4-dihydroisoquinolin-2(1H)-yl)aniline (0.430 g, 1.21 mmole) was dissolved in methanol (4 mL) and tetrahydrofuran (6 mL). Zinc powder (791 mg, 12.1 mmole) was added followed by ammonium chloride (647 mg, 12.1 mmole) in DI water (2 mL). The mixture was stirred under argon at ambient temperature for 45 min. and then cooled in an ice bath. N,N-diisopropylethylamine (0.421 mL, 2.42 mmole) was added, followed by ethyl chloroformate dropwise (194 mg, 1.82 mmole) and the reaction was stirred at ambient temperature for 45 min. It was filtered and evaporated. The crude oil was dissolved in dichloromethane (10 mL) and extracted with water (10 mL). The aqueous layer was extracted with additional dichloromethane (3×10 mL), the organic layers were pooled and evaporated to dryness. It was chromatographed on a silica gel column (10g) packed in chloroform. The column polarity was increased to 50% ethyl acetate/chloroform over 9 CV, at 12 mL/min. Fractions (22 mL each) containing the product were pooled and stripped to give of ethyl (2-amino-3-fluoro-4-(7-(trifluoromethyl)-3,4-dihydroisoquinolin-2(1H)-yl)phenyl)carbamate (0.150 g, 31% yield).

NMR Spectroscopy: $^1$H NMR (CDCl$_3$, 500 MHz): δ 7.42 (d, 1H), 7.39 (s, 1H), 7.28 (d, 1H), 6.98 (d, 1H), 6.45 (t, 1H), 6.25 (br s, 1H), 4.32 (s, 2H), 4.25 (q, 2H), 3.92 (br s, 2H), 3.45 (t, 2H), 3.06 (t, 2H), 1.38 (t, 3H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 μL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd18}$=7.5 min.

Example 19: Compound 19

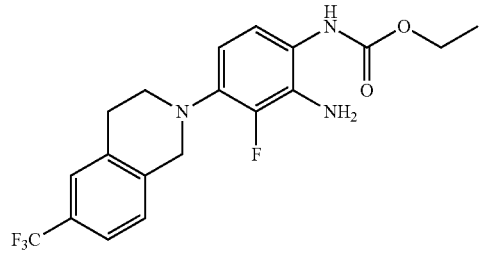

Step 1: Synthesis of 2-Fluoro-6-nitro-3-(6-(trifluoromethyl)-3,4-dihydroisoquinolin-2(1H)-yl)aniline 2,3-Difluoro-6-nitroaniline (0.238 g, 1.37 mmole) was dissolved in anhydrous dimethylsulfoxide (6 mL). 6-(trifluoromethyl)-1,2,3,4-tetrahydroisoquinoline hydrochloride (0.49 g, 2.05 mmole) was added triethylamine (0.64 mL) and solid iodine (1 mg). The mixture was heated at reflux for 2 h. under argon. The reaction was dissolved in dichloromethane (10 mL) and extracted with water (10 mL). The aqueous layer was washed with dichloromethane (10 mL), organics pooled and washed with brine (5 mL) and then dried through a 1 PS filter and evaporated to dryness. The crude material was chromatographed on a silica gel column (10 g) packed in hexanes. The column polarity was increased to 100% ethyl acetate over 12 CV, at 12 mL/min. Fractions (22 mL each) containing the product were pooled and stripped to give 2-fluoro-6-nitro-3-(6-(trifluoromethyl)-3,4-dihydroisoquinolin-2(1H)-yl)aniline (0.420 g, 87% yield)

Step 2: Synthesis of ethyl (2-amino-3-fluoro-4-(6-(trifluoromethyl)-3,4-dihydroisoquinolin-2(1H)-yl)phenyl)carbamate (Compound 19)

2-Fluoro-6-nitro-3-(6-(trifluoromethyl)-3,4-dihydroisoquinolin-2(1H)-yl)aniline (0.420 g, 1.18 mmole) was dissolved in methanol (5 mL) and tetrahydrofuran (5 mL). Zinc powder (0.693 g, 10.6 mmole) was added followed by ammonium chloride (567 mg, 10.6 mmole) in DI water (2 mL). The mixture was stirred under argon at ambient temperature for 0.5 h. and then cooled in an ice bath. N,N-diisopropylethylamine (0.423 mL, 2.43 mmole) was added, followed by ethyl chloroformate dropwise (227 mg, 2.12 mmole) and the reaction was stirred at ambient temperature for 1 h. The reaction was filtered and evaporated. The crude oil was dissolved in ethyl acetate (10 mL) and extracted with water (10 mL). the organic layer was then dried through a 1 PS filter and evaporated to dryness. It was chromatographed on a silica gel column (10 g) packed in chloroform. The column polarity was increased to 37% ethyl acetate/chloroform over 15 CV, at 12 mL/min. Fractions (22 mL each) containing the product were pooled and stripped to give ethyl (2-amino-3-fluoro-4-(6-(trifluoromethyl)-3,4-dihydroisoquinolin-2(1H)-yl)phenyl)carbamate (0.153 g, 33% yield).

NMR Spectroscopy: $^1$H NMR (DMSO, 300 MHz): δ 8.60 (br s, 1H), 7.55 (d, 2H), 7.40 (d, 1H), 6.85 (d, 1H), 6.30 (t, 1H), 4.80 (s, 2H), 4.21 (s, 2H), 4.10 (q, 2H), 3.30 (m, 2H), 2.99 (m, 2H), 1.32 (t, 3H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 μL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd19}$=11.4 min.

Example 20: Compound 20

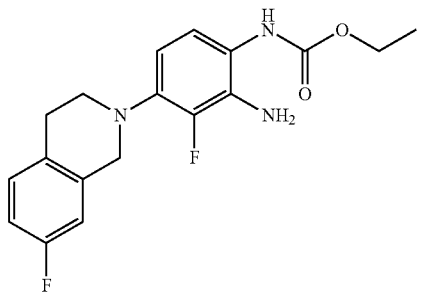 [SMILES: CCOC(=O)Nc1ccc(N2CCc3ccc(F)cc3C2)c(F)c1N]

Step 1: Synthesis of 2-Fluoro-3-(7-fluoro-3,4-dihydroisoquinolin-2(1H)-yl)-6-nitroaniline 2,3-Difluoro-6-nitroaniline (0.310 g, 1.78 mmole) was dissolved in anhydrous dimethylsulfoxide (6 mL). 7-fluoro-1,2,3,4-tetrahydroisoquinoline hydrochloride (0.50 g, 2.66 mmole) was added triethylamine (0.840 mL) and solid iodine (1 mg). The mixture was heated at reflux for 12 h. under argon. The reaction was dissolved in dichloromethane (10 mL) and extracted with water (10 mL). The aqueous layer was washed with dichloromethane (10 mL), organics pooled and washed with brine (5 mL) and then dried through a 1 PS filter and evaporated to dryness. The crude material was chromatographed on a silica gel column (10 g) packed in hexanes. The column polarity was increased to 100% ethyl acetate over 12 CV, at 12 mL/min. Fractions (22 mL each) containing the product were pooled and stripped to give 2-fluoro-3-(7-fluoro-3,4-dihydroisoquinolin-2(1H)-yl)-6-nitroaniline (0.500 g, 92% yield).

Step 2: Synthesis of ethyl (2-amino-3-fluoro-4-(7-fluoro-3,4-dihydroisoquinolin-2(1H)-yl)phenyl)carbamate (Compound 20)

2-Fluoro-3-(7-fluoro-3,4-dihydroisoquinolin-2(1H)-yl)-6-nitroaniline (0.500 g, 1.64 mmole) was dissolved in methanol (5 mL) and tetrahydrofuran (5 mL). Zinc powder (1.07 g, 16.4 mmole) was added followed by ammonium chloride (877 mg, 16.4 mmole) in DI water (2 mL). The mixture was stirred under argon at ambient temperature for 3.5 h. and then cooled in an ice bath. N, N-diisopropylethylamine (0.666 mL, 3.77 mmole) was added, followed by ethyl chloroformate dropwise (298 mg, 2.80 mmole) and the reaction was stirred at ambient temperature for 12 h. The reaction was cooled in an ice bath. N, N-diisopropylethylamine (0.350 mL) was added, followed by ethyl chloroformate dropwise (162 mg,). The reaction was stirred at ambient temperature for 1 h. It was filtered and evaporated. The crude oil was dissolved in ethyl acetate (10 mL) and extracted with water (10 mL). the organic layer was then dried through a 1 PS filter and evaporated to dryness. It was chromatographed on a silica gel column (10g) packed in chloroform. The column polarity was increased to 50% ethyl acetate/chloroform over 9 CV, at 12 mL/min. Fractions (22 mL each) containing the product were pooled and stripped to give of ethyl (2-amino-3-fluoro-4-(7-fluoro-3,4-dihydroisoquinolin-2(1H)-yl)phenyl)carbamate (0.150 g, 26% yield).

NMR Spectroscopy: $^1$H NMR (CDCl$_3$, 300 MHz): δ 7.10 (m, 1H), 6.80-7.00 (m, 3H), 6.48 (t, 1H), 6.25 (br s, 1H), 4.25 (m, 4H), 3.43 (m, 2H), 2.92 (t, 3H), 1.32 (t, 3H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 μL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd20}$=8.9 min.

Example 21: Compound 21

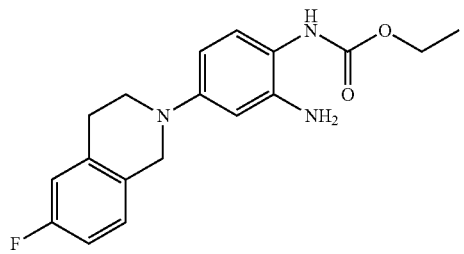 [SMILES: CCOC(=O)Nc1ccc(N2CCc3cc(F)ccc3C2)cc1N]

Step 1: Synthesis of 5-(6-Fluoro-3,4-dihydroisoquinolin-2(1H)-yl)-2-nitroaniline 5-Fluoro-2-nitroaniline (0.278 g, 1.78 mmole) was dissolved in anhydrous dimethylsulfoxide (6 mL). 6-fluoro-1,2,3,4-tetrahydroisoquinoline hydrochloride (0.50 g, 2.7 mmole) was added triethylamine (0.837 mL) and solid iodine (1 mg). The mixture was heated at reflux for 1.5 h. under argon. The reaction was dissolved in ethyl acetate (10 mL) and extracted with water (10 mL). The organic layer was washed with 3×30 mL water and then dried through a 1 PS filter and evaporated to dryness. The crude material was chromatographed on a silica gel column (10 g) packed in chloroform. The column polarity was increased to 15% ethyl acetate/chloroform over 10 CV, at 12 mL/min. Fractions (22 mL each) containing the product were pooled and stripped to give 5-(6-fluoro-3,4-dihydroisoquinolin-2(1H)-yl)-2-nitroaniline (0.43 g, 72% yield).

Step 2: Synthesis of ethyl (2-amino-4-(6-fluoro-3,4-dihydroisoquinolin-2(1H)-yl)phenyl)carbamate (Compound 21)

5-(6-Fluoro-3,4-dihydroisoquinolin-2(1H)-yl)-2-nitroaniline (0.432 g, 1.28 mmole) was dissolved in methanol (4 mL) and dioxane (4 mL). Zinc powder (837 mg, 12.8 mmole) was added followed by ammonium chloride (685 mg, 12.8 mmole) in DI water (2.0 mL). The mixture was stirred under argon at ambient temperature for 30 min. The mixture was cooled in an ice bath. N, N-diisopropylethylamine (0.556 mL, 3.20 mmole) was added, followed by ethyl chloroformate, dropwise (274 mg, 2.56 mmole) and the reaction was stirred at ambient temperature for 18 h. To the reaction was added ethyl acetate (10 mL) and extracted with water (10 mL). The organic layer was dried through a 1 PS filter and evaporated to dryness. It was chromatographed on a silica gel column (10 g) packed in chloroform. The column polarity was increased to 100% ethyl acetate/chloroform over 12 CV, at 12 mL/min. Fractions (22 mL each) containing the product were pooled and stripped to give ethyl (2-amino-4-(6-fluoro-3,4-dihydroisoquinolin-2 (1H)-yl)phenyl)carbamate (0.065 g, 15.4% yield).

NMR Spectroscopy: $^1$H NMR (CDCl$_3$, 500 MHz): δ 7.08 (m, 2H), 6.90 (m, 2H), 6.42 (m, 2H), 6.15 (br s, 1H), 4.36 (s, 2H), 4.22 (q, 2H), 2.50 (m, 2H), 2.98 (m, 2H), 1.32 (t, 3H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 µL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd21}$=5.4 min.

Example 22: Compound 22

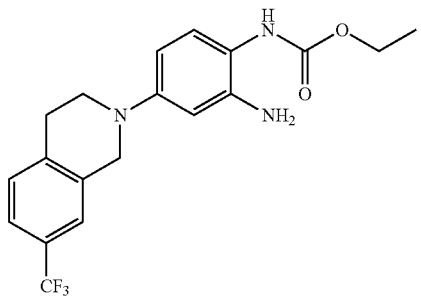 [SMILES: CCOC(=O)Nc1ccc(N2CCc3ccc(C(F)(F)F)cc3C2)cc1N]

Step 1: Synthesis of 2-Nitro-5-(7-(trifluoromethyl)-3,4-dihydroisoquinolin-2(1H)-yl)aniline 5-Fluoro-2-nitroaniline (0.219 g, 1.40 mmole) was dissolved in anhydrous dimethylsulfoxide (5 mL). 7-(trifluoromethyl)-1,2,3,4-tetrahydroisoquinoline hydrochloride (0.500 g, 2.10 mmole) was added triethylamine (0.660 mL) and solid iodine (1 mg) were added and the mixture was heated at reflux for an additional 3 h. under argon. The reaction was diluted with dichloromethane (10 mL) and extracted with water (10 mL). The organic layer was washed with 3×30 mL water and then dried through a 1 PS filter and evaporated to dryness. The crude material was chromatographed on a silica gel column (10 g) packed in hexanes. The column polarity was increased to 100% ethyl acetate/chloroform over 12 CV, at 12 mL/min. Fractions (22 mL each) containing the product were pooled and stripped to give 2-nitro-5-(7-(trifluoromethyl)-3,4-dihydroisoquinolin-2 (1H)-yl)aniline (0.410 g, 76% yield). Step 2: Synthesis of ethyl (2-amino-4-(7-(trifluoromethyl)-3,4-dihydroisoquinolin-2(1H)-yl)phenyl)carbamate (Compound 22) 2-Nitro-5-(7-(trifluoromethyl)-3,4-dihydroisoquinolin-2(1H)-yl)aniline (0.380 g, 1.13 mmole) was dissolved in methanol (4 mL) and tetrahydrofuran (6 mL). Zinc powder (737 mg, 11.3 mmole) was added followed by ammonium chloride (604 mg, 11.3 mmole) in DI water (2 mL). The mixture was stirred under argon at ambient temperature for 20 min. and then cooled to 10° C. in an ice bath. N, N-diisopropylethylamine (0.393 mL, 2.26 mmole) was added, followed by ethyl chloroformate dropwise (181 mg, 1.70 mmole) and the reaction was stirred at ambient temperature for 45 min. It was filtered and evaporated. The crude oil was dissolved in dichloromethane (10 mL) and extracted with water (10 mL). The aqueous layer was extracted with additional dichloromethane (3×10 mL), the organic layers were pooled and evaporated to dryness. It was chromatographed on a silica gel column (10g) packed in chloroform. The column polarity was increased to 50% ethyl acetate/chloroform over 9 CV, at 12 mL/min. Fractions (22 mL each) containing the product were pooled and stripped to give ethyl (2-amino-4-(7-(trifluoromethyl)-3,4-dihydroisoquinolin-2(1H)-yl)phenyl) carbamate (0.112 g, 26% yield).

NMR Spectroscopy: $^1$H NMR (CDCl$_3$, 500 MHz): δ 7.43 (m, 2H), 7.28 (d, 1H), 7.08 (d, 1H), 6.39-6.44 (m, 2H), 6.17 (br s, 1H), 4.42 (s, 2H), 4.22 (q, 2H), 3.90 (br s, 2H), 3.55 (t, 2H), 3.02 (t, 2H), 1.32 (t, 3H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 µL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd22}$=11.3 min.

Example 23: Compound 23

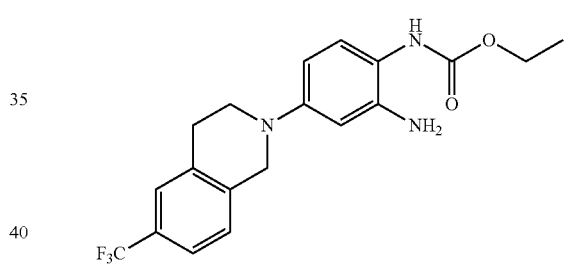

Step 1: Synthesis of 2-Nitro-5-(6-(trifluoromethyl)-3,4-dihydroisoquinolin-2(1H)-yl)aniline 5-Fluoro-2-nitroaniline (0.219 g, 1.40 mmole) was dissolved in anhydrous dimethylsulfoxide (6 mL). 6-(trifluoromethyl)-1,2,3,4-tetrahydroisoquinoline hydrochloride (0.50 g, 2.1 mmole) was added triethylamine (0.66 mL) and solid iodine (1 mg). The mixture was heated at reflux for 5 h. under argon. The reaction was dissolved in dichloromethane (10 mL) and extracted with water (10 mL). The organic layer was washed with 3×30 mL water and then dried through a 1 PS filter and evaporated to dryness. The crude material was chromatographed on a silica gel column (10 g) packed in hexanes. The column polarity was increased to 100% ethyl acetate over 10 CV, at 12 mL/min. Fractions (22 mL each) containing the product were pooled and stripped to give 2-nitro-5-(6-(trifluoromethyl)-3,4-dihydroisoquinolin-2(1H)-yl)aniline (0.23 g, 42% yield).

Step 2: Synthesis of ethyl (2-amino-4-(6-(trifluoromethyl)-3,4-dihydroisoquinolin-2(1H)-yl)phenyl) carbamate (Compound 23)

2-Nitro-5-(6-(trifluoromethyl)-3,4-dihydroisoquinolin-2 (1H)-yl)aniline (0.230 g, 0.682 mmole) was dissolved in methanol (5 mL) and tetrahydrofuran (5 mL). Zinc powder (0.396 g, 6.06 mmole) was added followed by ammonium chloride (324 mg, 6.06 mmole) in DI water (2 mL). The mixture was stirred under argon at ambient temperature for 0.5 h. and then cooled in an ice bath. N, N-diisopropylethylamine (0.242 mL, 1.39 mmole) was added, followed by ethyl chloroformate dropwise (313 mg, 1.23 mmole) and the reaction was stirred at ambient temperature for 1 h. The reaction was filtered and evaporated. The crude oil was dissolved in ethyl acetate (10 mL) and extracted with water (10 mL). the organic layer was then dried through a 1 PS filter and evaporated to dryness. It was chromatographed on a silica gel column (10 g) packed in chloroform. The column polarity was increased to 50% ethyl acetate/chloroform over 20 CV, at 12 mL/min. Fractions (22 mL each) containing the product were pooled and stripped to give ethyl (2-amino-4-(6-(trifluoromethyl)-3,4-dihydroisoquinolin-2(1H)-yl)phenyl)carbamate (0.10 g, 39% yield).

NMR Spectroscopy: $^1$H NMR (CDCl$_3$, 300 MHz): δ 7.45 (m, 2H), 7.25 (d, 1H), 7.10 (d, 1H), 6.43 (m, 2H), 6.18 (br s, 1H), 4.42 (s, 2H), 4.22 (q, 2H), 3.58 (m, 2H), 3.05 (m, 2H), 1.30 (t, 3H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 µL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd23}$=7.6 min.

Example 24: Compound 24

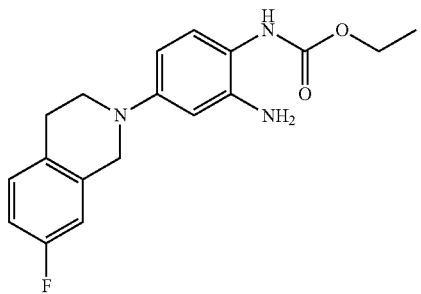 [SMILES: CCOC(=O)Nc1ccc(N2CCc3ccc(F)cc3C2)cc1N]

Step 1: Synthesis of 5-(7-Fluoro-3,4-dihydroisoquinolin-2(1H)-yl)-2-nitroaniline 5-Fluoro-2-nitroaniline (0.278 g, 1.78 mmole) was dissolved in anhydrous dimethylsulfoxide (6 mL). 6-fluoro-1,2,3,4-tetrahydroisoquinoline hydrochloride (0.50 g, 2.7 mmole) was added triethylamine (0.837 mL) and solid iodine (1 mg). The mixture was heated at reflux for 1.5 h. under argon. The reaction was dissolved in ethyl acetate (10 mL) and extracted with water (10 mL). The organic layer was washed with 3×30 mL water and then dried through a 1 PS filter and evaporated to dryness. The crude material was chromatographed on a silica gel column (10 g) packed in chloroform. The column polarity was increased to 15% ethyl acetate/chloroform over 10 CV, at 12 mL/min. Fractions (22 mL each) containing the product were pooled and stripped to give 5-(7-fluoro-3,4-dihydroisoquinolin-2(1H)-yl)-2-nitroaniline (0.43 g, 84% yield).

Step 2: Synthesis of ethyl (2-amino-4-(7-fluoro-3,4-dihydroisoquinolin-2(1H)-yl)phenyl)carbamate (Compound 24)

5-(7-Fluoro-3,4-dihydroisoquinolin-2(1H)-yl)-2-nitroaniline (0.430 g, 1.49 mmole) was dissolved in methanol (15 mL) and tetrahydrofuran (15 mL). Zinc powder (0.979 g, 15.0 mmole) was added followed by ammonium chloride (800 mg, 15.0 mmole) in DI water (2 mL). The mixture was stirred under argon at ambient temperature for 4 h. and then cooled in an ice bath. N, N-diisopropylethylamine (0.593 mL, 3.43 mmole) was added, followed by ethyl chloroformate dropwise (271 mg, 2.53 mmole) and the reaction was stirred at ambient temperature for 12 h. The reaction was filtered and evaporated. The crude oil was dissolved in ethyl acetate (10 mL) and extracted with water (10 mL). the organic layer was then dried through a 1 PS filter and evaporated to dryness. It was chromatographed on a silica gel column (10g) packed in chloroform. The column polarity was increased to 20% ethyl acetate/chloroform over 8 CV, at 12 mL/min. Fractions (22 mL each) containing the product were pooled and stripped to give ethyl (2-amino-4-(7-fluoro-3,4-dihydroisoquinolin-2(1H)-yl)phenyl)carbamate (0.028 g, 6% yield).

NMR Spectroscopy: $^1$H NMR (CDCl$_3$, 300 MHz): δ 7.10 (m, 2H), 6.80-6.98 (m, 2H), 6.48 (m, 2H), 6.15 (br s, 1H), 4.38 (s, 2H), 4.22 (q, 2H), 2.55 (m, 2H), 2.98 (t, 2H), 1.30 (m, 4H).

HPLC: Grace Alltima C18 reverse phase HPLC column (250×4.6 mm); Mobile Phase A: 0.1% TFA in water; Mobile Phase B: 0.1% TFA in 100% acetonitrile; Flow rate: 1 mL/min; Temperature: 30° C.; Injection Volume: 0.1-5 µL; Detection Wavelengths: 215-260 nm; Gradient: 0 min (60% A, 40% B), 15 min (10% A, 90% B), 18 min (10% A, 90% B), 18.1 min (60% A, 40% B), 20 min (60% A, 40% B). $t_{Cmpd24}$=5.7 min.

Example 25: Compound 27

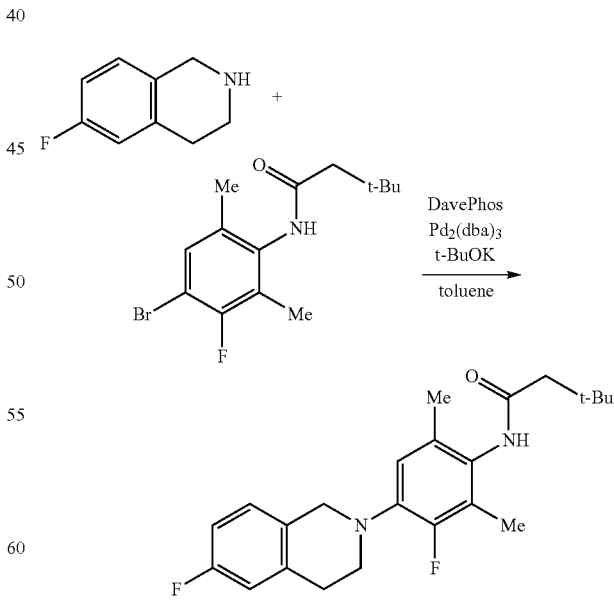

Under nitrogen, to N-(4-bromo-3-fluoro-2,6-dimethylphenyl)-3,3-dimethyl-butanamide (316 mg, 1.00 mmol, 1.00 equiv) in toluene (5 mL) at 23° C. were added 6-fluoro-1,2,3,4-tetrahydroisoquinoline (166 mg, 1.10 mmol, 1.10 equiv), DavePhos (47 mg, 0.12 mmol, 12 mol %), Pd$_2$(dba)$_3$ (37 mg, 0.040 mmol, 4.0 mol %), and t-BuOK (168 mg, 1.50 mmol, 1.50 equiv). After stirring for 24 hr at 90° C., the reaction mixture was concentrated in vacuo and the residue was purified by column chromatography on silica gel eluting with hexanes/EtOAc to afford 70 mg the title compound (18% yield).

NMR Spectroscopy: $^1$H NMR (300 MHz, CDCl$_3$, 23° C., δ): 7.02 (dd, J=9.0, 8.7 Hz, 1H), 6.89-6.77 (m, 3H), 6.61 (br s, 1H), 4.27 (br s, 2H), 3.43 (br s, 2H), 3.03 (br s, 2H), 2.24 (s, 2H), 2.17-2.10 (m, 6H), 1.08 (s, 9H).

Example 26: Compound 28

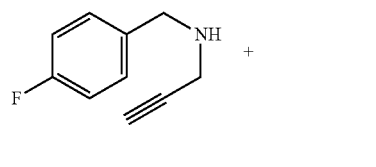

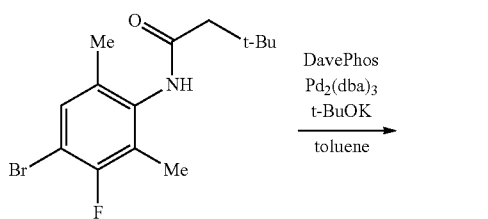

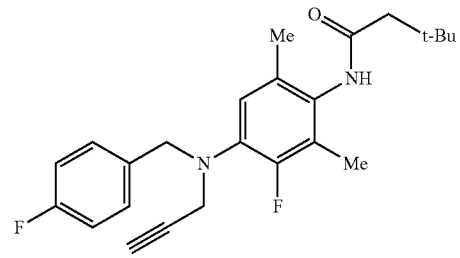

Under nitrogen, to N-(4-bromo-3-fluoro-2,6-dimethylphenyl)-3,3-dimethyl-butanamide (316 mg, 1.00 mmol, 1.00 equiv) in toluene (5 mL) at 23° C. were added N-(4-fluorobenzyl)prop-2-yn-1-amine (180 mg, 1.10 mmol, 1.10 equiv), DavePhos (47 mg, 0.12 mmol, 12 mol %), Pd$_2$(dba)$_3$ (37 mg, 0.040 mmol, 4.0 mol %), and t-BuOK (168 mg, 1.50 mmol, 1.50 equiv). After stirring for 2 d at 110° C., the reaction mixture was concentrated in vacuo and the residue was purified by column chromatography on silica gel eluting with hexanes/EtOAc to afford 25 mg the title compound (6% yield).

NMR Spectroscopy: $^1$H NMR (300 MHz, CDCl$_3$, 23° C., δ): 7.35 (dd, J=8.7, 5.7 Hz, 2H), 6.96 (dd, J=9.0, 8.7 Hz, 2H), 7.08 (d, J=7.5 Hz, 1H), 6.96 (br s, 1H), 3.88 (s, 2H), 3.58 (s, 2H), 2.23 (s, 1H), 2.12-2.08 (m, 8H), 1.10 (s, 9H).

Example 27: Compound 29

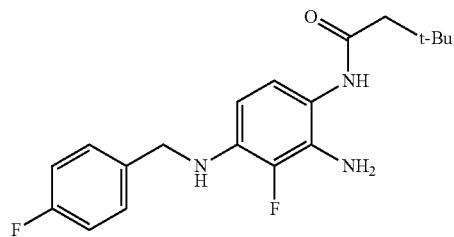 [SMILES: CC(C)(C)CC(=O)Nc1ccc(NCc2ccc(F)cc2)c(F)c1N]

Step 1: Synthesis of 2-Fluoro-N1-[(4-fluorophenyl)methyl]-4-nitro-benzene-1,3-diamine

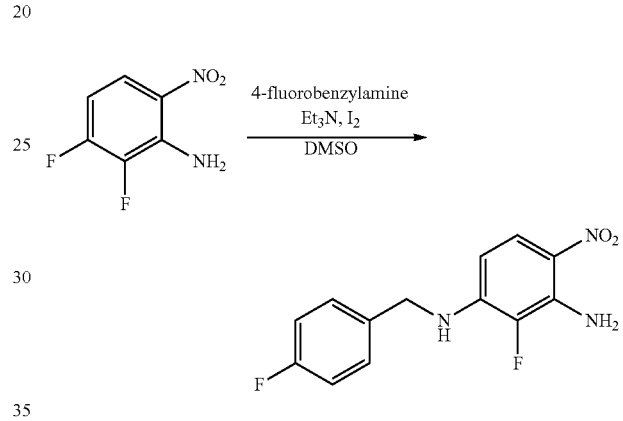

Under air, to 2,3-difluoro-6-nitroaniline (335 g, 1.92 mol, 1.00 equiv) in DMSO (400 mL) at 23° C. was added 4-fluorobenzylamine (395 mL, 3.46 mol, 1.80 equiv), Et$_3$N (642 mL, 4.61 mol, 2.40 equiv), and I$_2$ (243 mg, 0.960 mmol, 0.0500 mol %). After stirring at 100° C. with a reflux condenser for 3 hr, the reaction mixture was cooled to 23° C. and was poured into water (2 L). The resulting suspension was filtered and the solids were washed with water (3×800 mL). The solids were collected and dried inside an oven set to 110° C. for 8 hr to afford 530 g of the title compound as yellow solids (99% yield).

NMR Spectroscopy: $^1$H NMR (400 MHz, CDCl$_3$, 23° C., δ): 7.87 (dd, J=9.6, 1.6 Hz, 1H), 7.31-7.28 (m, 2H), 7.08-7.03 (m, 2H), 6.11-6.03 (m, 3H), 4.82 (br s, 1H), 4.44 (d, J=5.2 Hz, 2H).

Step 2: Synthesis of tert-Butyl N-[3-[bis(tert-butoxycarbonyl)amino]-2-fluoro-4-nitro-phenyl]-N-[(4-fluorophenyl)-methyl]carbamate

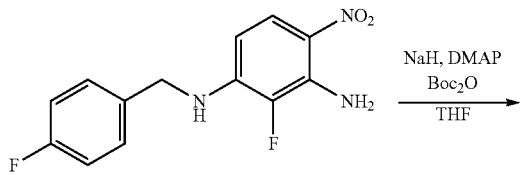

85

-continued

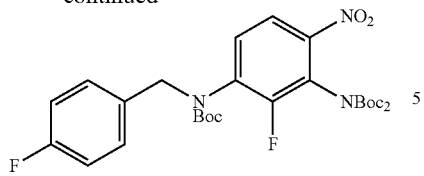

Under nitrogen, to 2-fluoro-N1-[(4-fluorophenyl) methyl]-4-nitro-benzene-1,3-diamine (5.58 g, 20.0 mmol, 1.00 equiv) in THF (200 mL) at 23° C. were added DMAP (244 mg, 2.00 mmol, 10.0 mol %), NaH (1.44 g, 60.0 mmol, 3.00 equiv), and Boc$_2$O (13.8 mL, 60.0 mmol, 3.00 equiv). After stirring for 1.5 hr at 60° C., the reaction mixture was cooled to 23° C. and water (200 mL) was added dropwise. The phases were separated and the aqueous phase was extracted with EtOAc (2×200 mL). The combined organic phases were washed with brine (200 mL) and dried (MgSO$_4$). The filtrate was concentrated in vacuo and the residue was purified by column chromatography on silica gel eluting with hexanes/EtOAc to afford 8.35 g of the title compound (72% yield).

NMR Spectroscopy: $^1$H NMR (300 MHz, CDCl$_3$, 23° C., δ): 7.81 (dd, J=9.0, 1.8 Hz, 1H), 7.24-7.15 (m, 3H), 6.95 (dd, J=8.4, 8.4 Hz, 2H), 4.80 (s, 2H), 1.41 (s, 9H), 1.36 (s, 18H).

Step 3: Synthesis of tert-Butyl N-[4-amino-3-[bis (tert-butoxycarbonyl)amino]-2-fluoro-phenyl]-N-[(4-fluorophenyl)methyl]carbamate

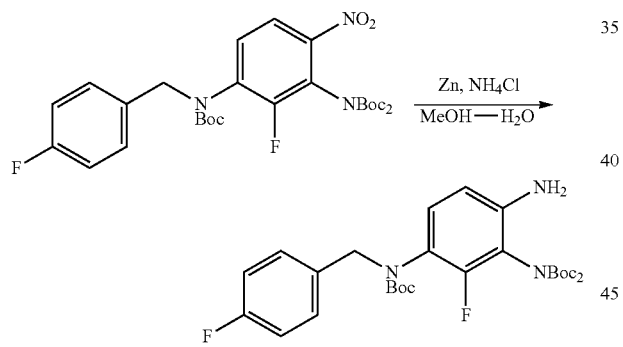

Under air, to tert-butyl N-[3-[bis(tert-butoxycarbonyl) amino]-2-fluoro-4-nitro-phenyl]-N-[(4-fluorophenyl) methyl]carbamate (8.35 g, 14.4 mmol, 1.00 equiv) in MeOH (144 mL) at 23° C. were added Zn powder (4.71 g, 72.1 mmol, 5.00 equiv) and NH$_4$Cl (3.85 g, 72.1 mmol, 5.00 equiv) in H$_2$O (20 mL). After stirring for 3 hr at 23° C., the reaction mixture was filtered through a pad of celite. The filtrate was concentrated in vacuo, and H$_2$O (200 mL) and EtOAc (200 mL) were added to the residue. The phases were separated and the aqueous phase was extracted with EtOAc (2×200 mL). The combined organic phases were washed with brine (200 mL) and dried (MgSO$_4$). The filtrate was concentrated in vacuo and the residue was purified by column chromatography on silica gel eluting with hexanes/ EtOAc to afford 6.00 g of the title compound (76% yield).

NMR Spectroscopy: $^1$H NMR (300 MHz, CDCl$_3$, 23° C., δ): 7.17 (dd, J=8.4, 5.4 Hz, 2H), 6.92 (dd, J=8.4, 8.4 Hz, 2H), 6.69 (dd, J=5.1, 5.1 Hz, 1H), 6.38 (d, J=5.1 Hz, 1H), 4.66 (br s, 2H), 1.38 (s, 27H).

86

Step 4: Synthesis of tert-Butyl N-[3-[bis(tert-butoxycarbonyl)amino]-4-(3,3-dimethylbutanoylamino)-2-fluoro-phenyl]-N-[(4-fluorophenyl) methyl]carbamate

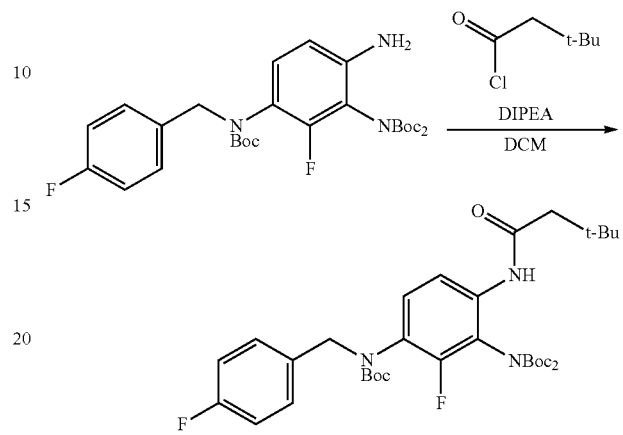

Under nitrogen, to tert-butyl N-[4-amino-3-[bis(tert-butoxycarbonyl)amino]-2-fluoro-phenyl]-N-[(4-fluorophenyl) methyl]carbamate (5.90 g, 10.7 mmol, 1.00 equiv) in DCM (26 mL) at 0° C. were added DIPEA (2.06 mL, 11.8 mmol, 1.10 equiv) and tert-butylacetyl chloride (1.65 mL, 11.8 mmol, 1.10 equiv). After stirring for 3 hr at 23° C., the reaction mixture was concentrated in vacuo, and the residue was purified by column chromatography on silica gel eluting with hexanes/EtOAc to afford 4.30 g of the title compound (62% yield).

NMR Spectroscopy: $^1$H NMR (300 MHz, CDCl$_3$, 23° C., δ): 7.98 (d, J=9.0 Hz, 1H), 7.21-6.90 (m, 6H), 4.71 (s, 2H), 2.18 (s, 2H), 1.39 (s, 9H), 1.34 (s, 18H), 1.06 (s, 9H).

Step 5: Synthesis of N-[2-amino-3-fluoro-4-[(4-fluorophenyl)methylamino]phenyl]-3,3-dimethyl-butanamide (Compound 29)

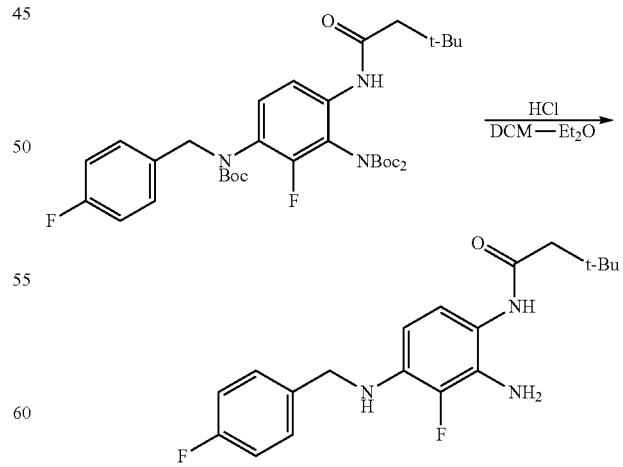

Under nitrogen, to tert-butyl N-[3-[bis(tert-butoxycarbonyl)amino]-4-(3,3-dimethylbutanoylamino)-2-fluoro-phenyl]-N-[(4-fluorophenyl)methyl]carbamate (1.30 g, 2.01 mmol, 1.00 equiv) in DCM (10 mL) at 23° C. was added HCl (2.0 M in Et₂O, 10.1 mL, 20.1 mmol, 10.0 equiv). After stirring for 15 hr at 23° C., NaHCO₃ (aq) (100 mL) was added to the reaction mixture. The phases were separated and the aqueous phase was extracted with EtOAc (2×100 mL). The combined organic phases were washed with brine (100 mL) and dried (MgSO₄). The filtrate was concentrated in vacuo and the residue was purified by column chromatography on silica gel eluting with hexanes/EtOAc to afford 690 mg of the title compound (99% yield).

NMR Spectroscopy: ¹H NMR (300 MHz, DMSO-d6, 23° C., δ): 9.00 (s, 1H), 7.36 (dd, J=8.4, 5.4 Hz, 2H), 7.11 (dd, J=8.4, 8.4 Hz, 2H), 6.56 (d, J=8.7 Hz, 1H), 5.92 (dd, J=6.0, 6.0 Hz, 1H), 5.83 (dd, J=8.7, 8.7 Hz, 1H), 4.54 (s, 2H), 4.27 (d, J=6.0 Hz, 2H), 2.09 (s, 2H), 1.00 (s, 9H).

Example 28: Compound 30

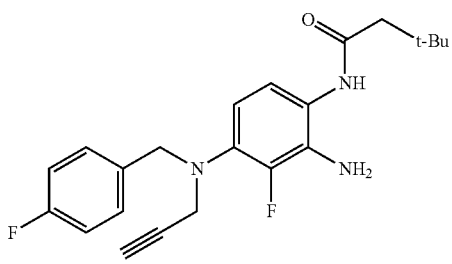 [SMILES: C#CCN(Cc1ccc(F)cc1)c1ccc(NC(=O)CC(C)(C)C)c(N)c1F]

Step 1: Synthesis of 1-Bis(tert-butoxylcarbonyl) amino-2,3-difluoro-6-nitrobenzene

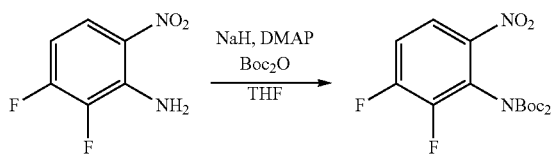

Under nitrogen, to 2,3-difluoro-6-nitroaniline (3.48 g, 20.0 mmol, 1.00 equiv) in THF (100 mL) at 23° C. were added DMAP (122 mg, 1.00 mmol, 5.00 mol %), NaH (1.44 g, 60.0 mmol, 3.00 equiv), and Boc₂O (13.8 mL, 60 mmol, 3.00 equiv). After stirring for 1 h at 60° C., the reaction mixture was cooled to 23° C. and water (100 mL) was added. The solution was then neutralized with 1N HCl (aq) and was extracted with EtOAc (2×100 mL). The combined organic phases were washed with brine (100 mL) and dried (MgSO₄). The filtrate was concentrated in vacuo and the residue was purified by chromatography on silica gel eluting with hexanes/EtOAc to afford 6.20 g of the title compound (83% yield).

NMR Spectroscopy: ¹H NMR (300 MHz, CDCl₃, 23° C., δ): 7.98-7.90 (m, 1H), 7.37-7.27 (m, 1H), 1.40 (s, 18H).

Step 2: Synthesis of tert-Butyl N-tert-butoxycarbonyl-N-[2-fluoro-3-[(4-fluorophenyl)methylamino]-6-nitro-phenyl]carbamate

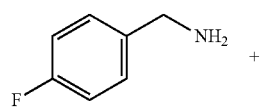

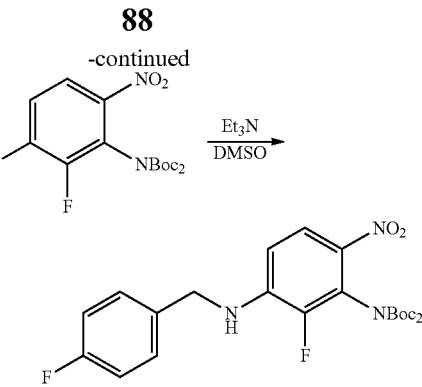

Under nitrogen, to 1-bis(tert-butoxylcarbonyl)amino-2,3-difluoro-6-nitrobenzene (1.87 g, 5.00 mmol, 1.00 equiv) in DMSO (5 mL) at 23° C. were added 4-fluorobenzylamine (1.03 mL, 9.00 mmol, 1.80 equiv) and Et₃N (0.837 mL, 6.00 mmol, 1.20 equiv). After stirring for 1.5 hr at 23° C., the reaction mixture was cooled to 23° C. and water (10 mL) was added. The solution was then neutralized with 1N HCl (aq) and was extracted with EtOAc (2×10 mL). The combined organic phases were washed with brine (10 mL) and dried (MgSO₄). The filtrate was concentrated in vacuo and the residue was purified by chromatography on silica gel eluting with hexanes/EtOAc to afford 2.00 g of the title compound (83% yield).

NMR Spectroscopy: ¹H NMR (300 MHz, CDCl₃, 23° C., δ): 7.97 (d, J=9.0 Hz, 1H), 7.31 (dd, J=8.7, 5.7 Hz, 2H), 7.07 (dd, J=8.7, 8.7 Hz, 2H), 6.59 (dd, J=8.4, 8.4 Hz, 1H), 4.98 (br s, 1H), 4.44 (br s, 2H), 1.42 (s, 18H).

Step 3: Synthesis of tert-Butyl N-tert-butoxycarbonyl-N-[6-(3,3-dimethylbutanoylamino)-2-fluoro-3-[(4-fluorophenyl)methyl-prop-2-ynyl-amino]phenyl] carbamate

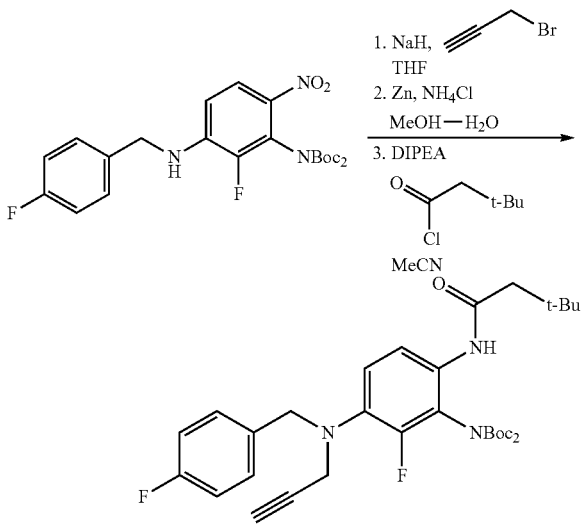

Under nitrogen, to tert-butyl N-tert-butoxycarbonyl-N-[2-fluoro-3-[(4-fluorophenyl)-methylamino]-6-nitro-phenyl] carbamate (2.00 g, 4.17 mmol, 1.00 equiv) in THF (4.2 mL) at 23° C. were added propargyl bromide (0.948 mL, 12.5 mmol, 3.00 equiv) and NaH (300 mg, 12.5 mmol, 3.00 equiv). After stirring for 1 hr at 23° C., the reaction mixture was cooled to 0° C. and water (10 mL) was added. The reaction mixture was extracted with EtOAc (2×10 mL). The combined organic phases were washed with brine (10 mL) and dried (MgSO$_4$). The filtrate was concentrated in vacuo to afford a crude alkylation product, which was used in the next step without further purification.

Under air, to the crude product obtained above in MeOH (42 mL) at 23° C. were added Zn powder (1.36 g, 20.9 mmol, 5.00 equiv) and NH$_4$Cl (1.12 g, 20.9 mmol, 5.00 equiv) in H$_2$O (5 mL). After stirring for 3 hr at 23° C., the reaction mixture was filtered through a pad of celite. The filtrate was concentrated in vacuo, and H$_2$O (50 mL) and EtOAc (50 mL) were added to the residue. The phases were separated and the aqueous phase was extracted with EtOAc (2×50 mL). The combined organic phases were washed with brine (100 mL) and dried (MgSO$_4$). The filtrate was concentrated in vacuo to afford a crude reduction product, which was used in the next step without further purification.

Under nitrogen, to the crude reduction product obtained above in MeCN (4.2 mL) at 23° C. were added DIPEA (1.31 mL, 7.51 mmol, 1.80 equiv) and tert-butylacetyl chloride (1.05 mL, 7.51 mmol, 1.80 equiv). After stirring for 1 hr at 23° C., the reaction mixture was concentrated in vacuo, and the residue was purified by column chromatography on silica gel eluting with hexanes/EtOAc to afford 1.90 g of the title compound (78% yield over 3 steps).

NMR Spectroscopy: $^1$H NMR (300 MHz, CDCl$_3$, 23° C., δ): 7.90 (d, J=8.7 Hz, 1H), 7.37 (dd, J=8.7, 5.7 Hz, 2H), 7.16 (dd, J=9.0, 9.0 Hz, 1H), 7.06 (s, 1H), 6.99 (dd, J=8.7, 8.4 Hz, 2H), 4.27 (s, 2H), 3.76 (d, J=2.4 Hz, 2H), 2.25 (t, J=2.4 Hz, 1H), 2.19 (s, 2H), 1.40 (s, 18H), 1.07 (s, 9H).

Step 4: Synthesis of N-(2-amino-3-fluoro-4-((4-fluorobenzyl)(prop-2-yn-1-yl)amino)phenyl)-3,3-dimethylbutanamide (Compound 30)

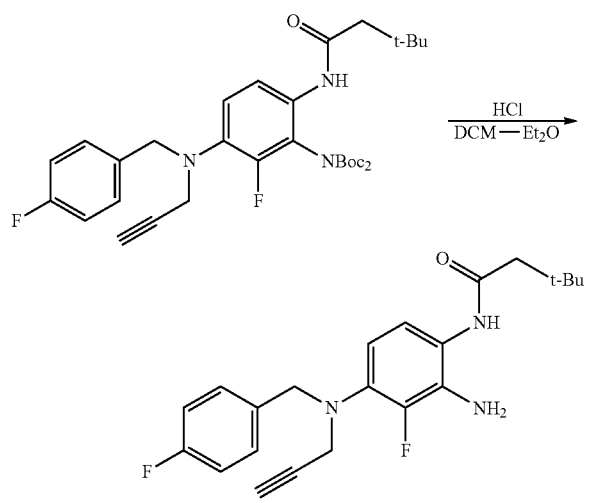

Under nitrogen, to tert-butyl N-tert-butoxycarbonyl-N-[6-(3,3-dimethylbutanoylamino)-2-fluoro-3-[(4-fluorophenyl) methyl-prop-2-ynyl-amino]phenyl]carbamate (1.90 g, 3.24 mmol, 1.00 equiv) in DCM (8 mL) at 23° C. was added HCl (2.0 M in Et$_2$O, 16.2 mL, 20.1 mmol, 10.0 equiv). After stirring for 15 hr at 23° C., NaHCO$_3$ (aq) (10 mL) was added to the reaction mixture. The phases were separated and the aqueous phase was extracted with EtOAc (2×10 mL). The combined organic phases were washed with brine (10 mL) and dried (MgSO$_4$). The filtrate was concentrated in vacuo to afford 1.20 g of the title compound (96% yield).

NMR Spectroscopy: $^1$H NMR (300 MHz, methanol-d4, 23° C., δ): 7.34 (dd, J=8.7, 5.7 Hz, 2H), 6.96 (dd, J=9.0, 9.0 Hz, 2H), 6.71 (d, J=8.7 Hz, 1H), 6.50 (dd, J=9.0, 8.7 Hz, 1H), 4.22 (s, 2H), 3.69 (d, J=2.4 Hz, 2H), 2.56 (t, J=2.4 Hz, 1H), 2.19 (s, 2H), 1.07 (s, 9H).

Example 29: Compound 31

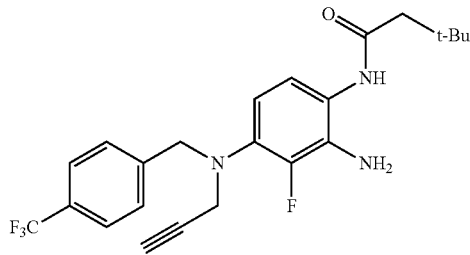 [SMILES: C#CCN(Cc1ccc(C(F)(F)F)cc1)c1ccc(NC(=O)CC(C)(C)C)c(N)c1F]

Step 1: Synthesis of tert-Butyl N-tert-butoxycarbonyl-N-[2-fluoro-6-nitro-3-[[4-(trifluoromethyl)phenyl]-methylamino]phenyl]carbamate

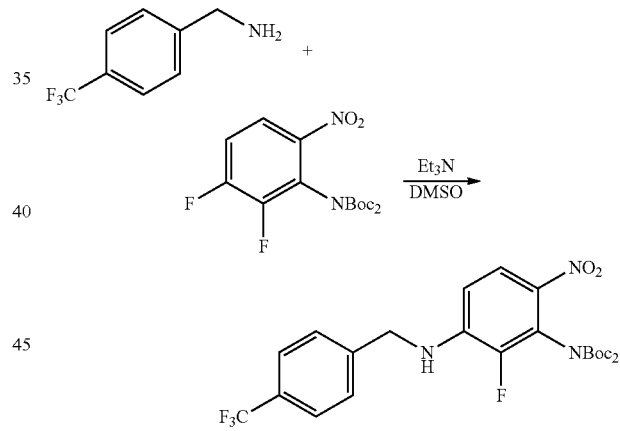

Under nitrogen, to 1-bis(tert-butoxylcarbonyl)amino-2,3-difluoro-6-nitrobenzene (1.87 g, 5.00 mmol, 1.00 equiv) in DMSO (5 mL) at 23° C. were added 4-(trifluoromethyl)benzylamine (1.28 mL, 9.00 mmol, 1.80 equiv) and Et$_3$N (0.837 mL, 6.00 mmol, 1.20 equiv). After stirring for 1.5 hr at 23° C., the reaction mixture was cooled to 23° C. and water (10 mL) was added. The solution was then neutralized with 1N HCl (aq) and was extracted with EtOAc (2×10 mL). The combined organic phases were washed with brine (10 mL) and dried (MgSO$_4$). The filtrate was concentrated in vacuo and the residue was purified by chromatography on silica gel eluting with hexanes/EtOAc to afford 1.90 g of the title compound (72% yield).

NMR Spectroscopy: $^1$H NMR (300 MHz, CDCl$_3$, 23° C., δ): 7.95 (d, J=9.0 Hz, 1H), 7.63 (d, J=7.8 Hz, 2H), 7.48 (d, J=7.8 Hz, 2H), 6.54 (dd, J=8.4, 8.4 Hz, 1H), 5.08 (br s, 1H), 4.56 (br s, 2H), 1.41 (s, 18H).

Step 2: Synthesis of tert-Butyl N-tert-butoxycarbonyl-N-[6-(3,3-dimethylbutanoylamino)-2-fluoro-3-[prop-2-ynyl-[[4-(trifluoromethyl)phenyl]methyl]amino]phenyl]carbamate

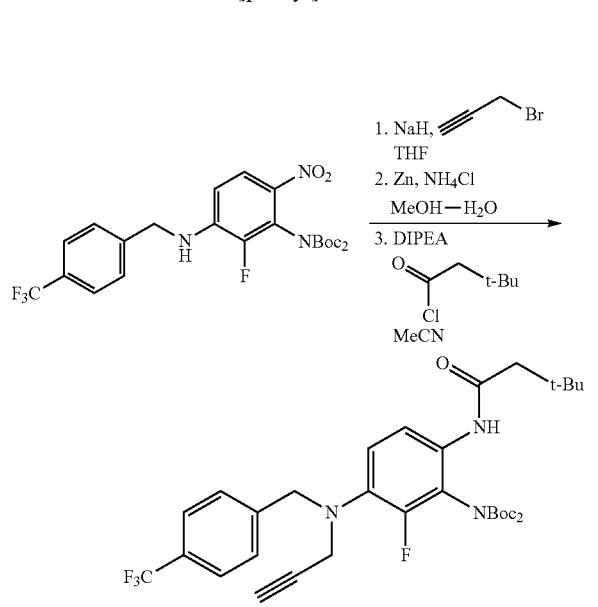

Under nitrogen, to tert-butyl N-tert-butoxycarbonyl-N-[2-fluoro-6-nitro-3-[[4-(trifluoromethyl)phenyl]methylamino]phenyl]carbamate (1.90 g, 3.59 mmol, 1.00 equiv) in THF (3.6 mL) at 23° C. were added propargyl bromide (0.816 mL, 10.8 mmol, 3.00 equiv) and NaH (258 mg, 10.8 mmol, 3.00 equiv). After stirring for 1 hr at 23° C., the reaction mixture was cooled to 0° C. and water (10 mL) was added. The reaction mixture was extracted with EtOAc (2×10 mL). The combined organic phases were washed with brine (10 mL) and dried (MgSO$_4$). The filtrate was concentrated in vacuo to afford a crude alkylation product, which was used in the next step without further purification.

Under air, to the crude product obtained above in MeOH (36 mL) at 23° C. were added Zn powder (1.17 g, 18.0 mmol, 5.00 equiv) and NH$_4$Cl (960 mg, 18.0 mmol, 5.00 equiv) in H$_2$O (5 mL). After stirring for 3 hr at 23° C., the reaction mixture was filtered through a pad of celite. The filtrate was concentrated in vacuo, and H$_2$O (50 mL) and EtOAc (50 mL) were added to the residue. The phases were separated and the aqueous phase was extracted with EtOAc (2×50 mL). The combined organic phases were washed with brine (100 mL) and dried (MgSO$_4$). The filtrate was concentrated in vacuo to afford a crude reduction product, which was used in the next step without further purification.

Under nitrogen, to the crude reduction product obtained above in MeCN (3.6 mL) at 23° C. were added DIPEA (1.13 mL, 6.46 mmol, 1.80 equiv) and tert-butylacetyl chloride (0.902 mL, 6.46 mmol, 1.80 equiv). After stirring for 1 hr at 23° C., the reaction mixture was concentrated in vacuo, and the residue was purified by column chromatography on silica gel eluting with hexanes/EtOAc to afford 1.90 g of the title compound (83% yield over 3 steps). NMR Spectroscopy: $^1$H NMR (300 MHz, CDCl$_3$, 23° C., δ): 7.91 (d, J=8.7 Hz, 1H), 7.62-7.50 (m, 4H), 7.15 (dd, J=9.0, 9.0 Hz, 1H), 7.07 (s, 1H), 4.36 (s, 2H), 3.73 (d, J=2.4 Hz, 2H), 2.25 (t, J=2.4 Hz, 1H), 2.19 (s, 2H), 1.40 (s, 18H), 1.07 (s, 9H).

Step 3: Synthesis of N-[2-amino-3-fluoro-4-[prop-2-ynyl-[[4-(trifluoromethyl)phenyl]methyl]amino]phenyl]-3,3-dimethyl-butanamide (Compound 31)

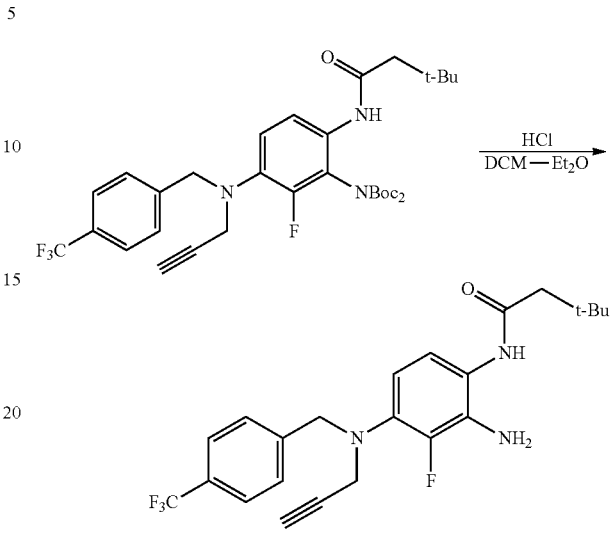

Under nitrogen, to tert-butyl N-tert-butoxycarbonyl-N-[6-(3,3-dimethylbutanoylamino)-2-fluoro-3-[prop-2-ynyl-[[4-(trifluoromethyl)phenyl]methyl]amino]phenyl]carbamate (1.90 g, 2.99 mmol, 1.00 equiv) in DCM (7.5 mL) at 23° C. was added HCl (2.0 M in Et$_2$O, 15.0 mL, 29.9 mmol, 10.0 equiv). After stirring for 15 hr at 23° C., NaHCO$_3$ (aq) (10 mL) was added to the reaction mixture. The phases were separated and the aqueous phase was extracted with EtOAc (2×10 mL). The combined organic phases were washed with brine (10 mL) and dried (MgSO$_4$). The filtrate was concentrated in vacuo and the residue was purified by chromatography on silica gel eluting with hexanes/EtOAc to afford 600 mg of the title compound (46% yield).

NMR Spectroscopy: $^1$H NMR (300 MHz, methanol-d4, 23° C., δ): 7.58-7.50 (m, 4H), 6.70 (d, J=9.0 Hz, 1H), 6.50 (dd, J=9.0, 8.7 Hz, 1H), 4.35 (s, 2H), 3.76 (d, J=2.4 Hz, 2H), 2.59 (t, J=2.4 Hz, 1H), 2.20 (s, 2H), 1.03 (s, 9H).

Example 30: Compound 32

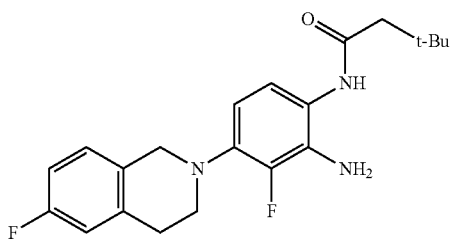 [SMILES: CC(C)(C)CC(=O)Nc1ccc(N2CCc3cc(F)ccc3C2)c(F)c1N]

Step 1: Synthesis of 2-Fluoro-3-(6-fluoro-3,4-dihydroisoquinolin-2(1H)-yl)-6-nitroaniline

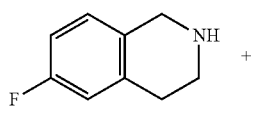 +

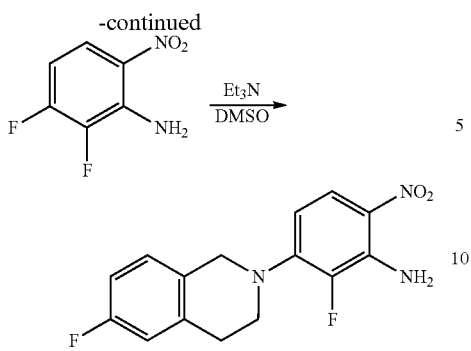

Under nitrogen, to 2,3-difluoro-6-nitro-aniline (1.74 g, 10.0 mmol, 1.00 equiv) in DMSO (10 mL) at 23° C. were added N-[(4-fluoro-2-methyl-phenyl)methyl]ethanamine (1.67 g, 10.0 mmol, 1.00 equiv) and Et$_3$N (1.67 mL, 12.0 mmol, 1.20 equiv). After stirring for 1 hr at 100° C., the reaction mixture was cooled to 23° C. and water (100 mL) was added. The solution was then neutralized with 1N HCl (aq) and was extracted with EtOAc (2×100 mL). The combined organic phases were washed with brine (100 mL) and dried (MgSO$_4$). The filtrate was concentrated in vacuo and the residue was purified by chromatography on silica gel eluting with hexanes/EtOAc to afford 1.38 g of the title compound (45% yield).

NMR Spectroscopy: $^1$H NMR (300 MHz, CDCl$_3$, 23° C., δ): 7.87 (d, J=9.0 Hz, 1H), 7.08 (dd, J=7.8 Hz, 7.8 Hz, 1H), 6.95-6.85 (m, 2H), 6.33 (dd, J=8.4, 8.4 Hz, 1H), 4.49 (s, 2H), 3.66 (t, J=6.0 Hz, 2H), 2.99 (t, J=6.0 Hz, 2H).

Step 2: Synthesis of tert-Butyl N-tert-butoxycarbonyl-N-[3-[ethyl-[(4-fluoro-2-methyl-phenyl)methyl]amino]-2-fluoro-6-nitro-phenyl]carbamate

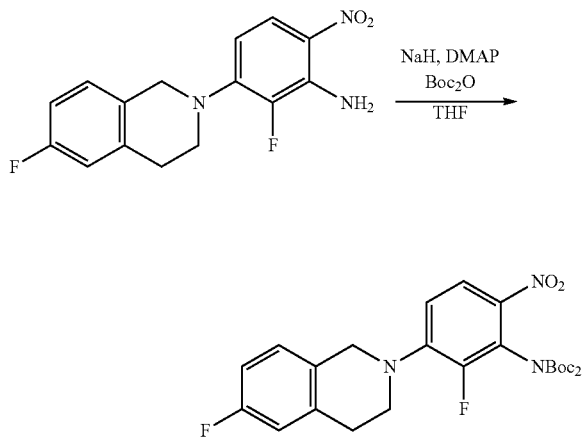

Under nitrogen, to 2-fluoro-3-(6-fluoro-3,4-dihydroisoquinolin-2(1H)-yl)-6-nitroaniline (1.38 g, 4.29 mmol, 1.00 equiv) in THF (21 mL) at 23° C. were added DMAP (26.2 mg, 0.214 mmol, 5.00 mol %), NaH (309 mg, 12.9 mmol, 3.00 equiv), and Boc$_2$O (2.96 mL, 12.9 mmol, 3.00 equiv). After stirring for 1 h at 60° C., the reaction mixture was cooled to 23° C. and water (50 mL) was added. The solution was then neutralized with 1N HCl (aq) and was extracted with EtOAc (2×50 mL). The combined organic phases were washed with brine (100 mL) and dried (MgSO$_4$). The filtrate was concentrated in vacuo and the residue was purified by chromatography on silica gel eluting with hexanes/EtOAc to afford 2.17 g of the title compound (97% yield).

NMR Spectroscopy: $^1$H NMR (300 MHz, CDCl$_3$, 23° C., δ): 7.96 (d, J=9.0 Hz, 1H), 7.10 (dd, J=7.8 Hz, 7.8 Hz, 1H), 6.95-6.83 (m, 3H), 4.46 (s, 2H), 3.64 (t, J=6.0 Hz, 2H), 2.99 (t, J=6.0 Hz, 2H), 1.41 (s, 18H).

Step 3: Synthesis of tert-Butyl N-tert-butoxycarbonyl-N-[6-(3,3-dimethylbutanoylamino)-2-fluoro-3-(6-fluoro-3,4-dihydro-1H-isoquinolin-2-yl)phenyl]carbamate

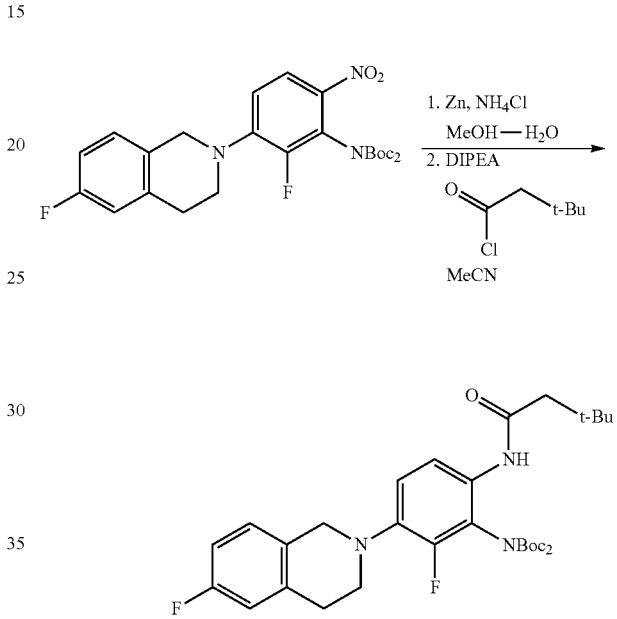

Under air, to tert-butyl N-tert-butoxycarbonyl-N-[3-[ethyl-[(4-fluoro-2-methyl-phenyl)methyl]amino]-2-fluoro-6-nitro-phenyl]carbamate (2.17 g, 4.29 mmol, 1.00 equiv) in MeOH (43 mL) at 23° C. were added Zn powder (1.40 g, 21.5 mmol, 5.00 equiv) and NH$_4$Cl (1.15 g, 21.5 mmol, 5.00 equiv) in H$_2$O (5 mL). After stirring for 3 hr at 23° C., the reaction mixture was filtered through a pad of celite. The filtrate was concentrated in vacuo, and H$_2$O (50 mL) and EtOAc (50 mL) were added to the residue. The phases were separated and the aqueous phase was extracted with EtOAc (2×50 mL). The combined organic phases were washed with brine (100 mL) and dried (MgSO$_4$). The filtrate was concentrated in vacuo to afford a crude reduction product, which was used in the next step without further purification.

Under nitrogen, to the crude reduction product obtained above in MeCN (4.3 mL) at 23° C. were added DIPEA (1.35 mL, 7.72 mmol, 1.80 equiv) and tert-butylacetyl chloride (1.08 mL, 7.72 mmol, 1.80 equiv). After stirring for 1 hr at 23° C., the reaction mixture was concentrated in vacuo, and the residue was purified by column chromatography on silica gel eluting with hexanes/EtOAc to afford 2.20 g of the title compound (89% yield over 2 steps).

NMR Spectroscopy: $^1$H NMR (300 MHz, CDCl$_3$, 23° C., δ): 7.87 (d, J=8.7 Hz, 1H), 7.10-6.80 (m, 4H), 4.23 (s, 2H), 3.38 (t, J=6.0 Hz, 2H), 2.96 (t, J=6.0 Hz, 2H), 2.16 (s, 2H), 1.41 (s, 18H), 1.07 (s, 9H).

Step 4: Synthesis of ethyl (3-fluoro-4-(6-fluoro-3,4-dihydroisoquinolin-2(1H)-yl)-2,6-dimethylphenyl)-carbamate (Compound 32)

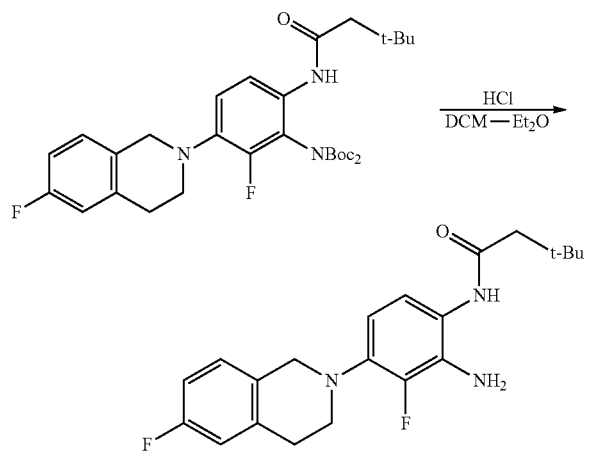

Under nitrogen, to tert-butyl N-tert-butoxycarbonyl-N-[6-(3,3-dimethylbutanoylamino)-2-fluoro-3-(6-fluoro-3,4-dihydro-1H-isoquinolin-2-yl)phenyl]carbamate (2.20 g, 3.83 mmol, 1.00 equiv) in DCM (10 mL) at 23° C. was added HCl (2.0 M in Et₂O, 19.2 mL, 38.3 mmol, 10.0 equiv). After stirring for 15 hr at 23° C., NaHCO₃ (aq) (100 mL) was added to the reaction mixture. The phases were separated and the aqueous phase was extracted with EtOAc (2×100 mL). The combined organic phases were washed with brine (100 mL) and dried (MgSO₄). The filtrate was concentrated in vacuo to afford 1.20 g of the title compound (84% yield).

NMR Spectroscopy: ¹H NMR (300 MHz, methanol-d4, 23° C., δ): 7.16-7.10 (m, 1H), 6.94-6.79 (m, 3H), 6.46 (dd, J=8.7, 8.7 Hz, 1H), 4.19 (s, 2H), 3.36 (t, J=6.0 Hz, 2H), 2.96 (t, J=6.0 Hz, 2H), 2.27 (s, 2H), 1.11 (s, 9H).

Example 31: Compound 33

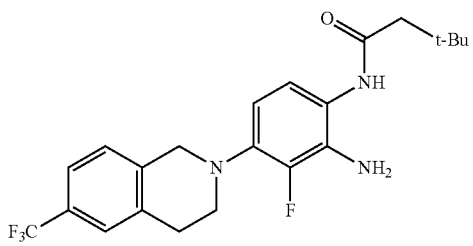 [SMILES: CC(C)(C)CC(=O)Nc1ccc(N2CCc3cc(C(F)(F)F)ccc3C2)c(F)c1N]

Step 1: Synthesis of tert-Butyl N-tert-butoxycarbonyl-N-[2-fluoro-6-nitro-3-[6-(trifluoromethyl)-3,4-dihydro-1H-isoquinolin-2-yl]phenyl]carbamate

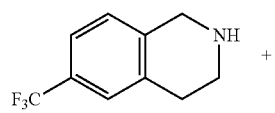 +

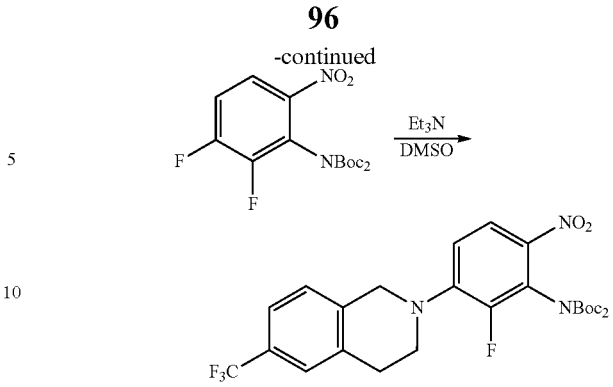

Under nitrogen, to 1-bis(tert-butoxylcarbonyl)amino-2,3-difluoro-6-nitrobenzene (1.87 g, 5.00 mmol, 1.00 equiv) in DMSO (5 mL) at 23° C. were added 6-(trifluoromethyl)-1,2,3,4-tetrahydroisoquinoline (1.01 g, 5.00 mmol, 1.00 equiv) and Et₃N (1.74 mL, 12.5 mmol, 2.50 equiv). After stirring for 1.5 hr at 23° C., the reaction mixture was cooled to 23° C. and water (10 mL) was added. The solution was then neutralized with 1N HCl (aq) and was extracted with EtOAc (2×10 mL). The combined organic phases were washed with brine (10 mL) and dried (MgSO₄). The filtrate was concentrated in vacuo and the residue was purified by chromatography on silica gel eluting with hexanes/EtOAc to afford 1.39 g of the title compound (50% yield).

NMR Spectroscopy: ¹H NMR (300 MHz, CDCl₃, 23° C., δ): 7.97 (d, J=9.0 Hz, 1H), 7.47 (d, J=8.1 Hz, 1H), 7.41 (s, 1H), 7.30 (d, J=8.1 Hz, 1H), 6.94 (dd, J=8.7, 8.4 Hz, 1H), 4.54 (s, 2H), 3.67 (t, J=6.0 Hz, 2H), 3.07 (t, J=6.0 Hz, 2H), 1.42 (s, 18H).

Step 2: Synthesis of tert-Butyl N-tert-butoxycarbonyl-N-[6-(3,3-dimethylbutanoylamino)-2-fluoro-3-[6-(trifluoromethyl)-3,4-dihydro-1H-isoquinolin-2-yl]phenyl]carbamate

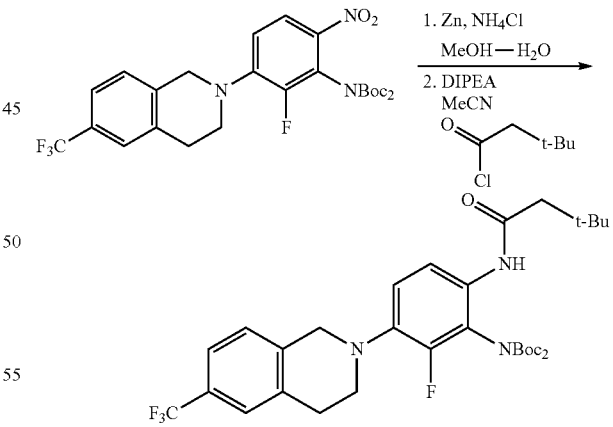

Under air, to tert-butyl N-tert-butoxycarbonyl-N-[2-fluoro-6-nitro-3-[6-(trifluoromethyl)-3,4-dihydro-1H-isoquinolin-2-yl]phenyl]carbamate (1.39 g, 2.50 mmol, 1.00 equiv) in MeOH (25 mL) at 23° C. were added Zn powder (817 mg, 12.5 mmol, 5.00 equiv) and NH₄Cl (669 mg, 12.5 mmol, 5.00 equiv) in H₂O (5 mL). After stirring for 3 hr at 23° C., the reaction mixture was filtered through a pad of celite. The filtrate was concentrated in vacuo, and H₂O (50 mL) and EtOAc (50 mL) were added to the residue. The phases were separated and the aqueous phase was extracted with EtOAc (2×50 mL). The combined organic phases were washed with brine (100 mL) and dried (MgSO₄). The filtrate was concentrated in vacuo to afford a crude reduction product, which was used in the next step without further purification.

Under nitrogen, to the crude reduction product obtained above in MeCN (2.5 mL) at 23° C. were added DIPEA (0.784 mL, 4.50 mmol, 1.80 equiv) and tert-butylacetyl chloride (0.628 mL, 4.50 mmol, 1.80 equiv). After stirring for 1 hr at 23° C., the reaction mixture was concentrated in vacuo, and the residue was purified by column chromatography on silica gel eluting with hexanes/EtOAc to afford 1.25 g of the title compound (80% yield over 2 steps).

NMR Spectroscopy: $^1$H NMR (300 MHz, CDCl₃, 23° C., δ): 7.95 (d, J=8.7 Hz, 1H), 7.44 (d, J=8.1 Hz, 1H), 7.37 (s, 1H), 7.30-7.18 (m, 2H), 7.09 (s, 1H), 4.37 (s, 2H), 3.48 (t, J=6.0 Hz, 2H), 3.10 (t, J=6.0 Hz, 2H), 2.20 (s, 2H), 1.42 (s, 18H), 1.08 (s, 9H).

Step 3: Synthesis of N-[2-amino-3-fluoro-4-[6-(trifluoromethyl)-3,4-dihydro-1H-isoquinolin-2-yl]phenyl]-3,3-dimethyl-butanamide (Compound 33)

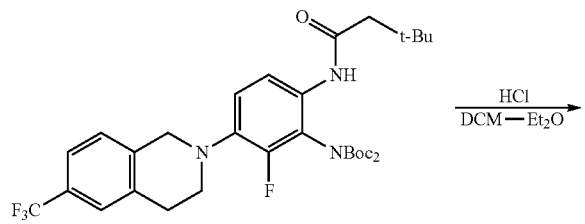

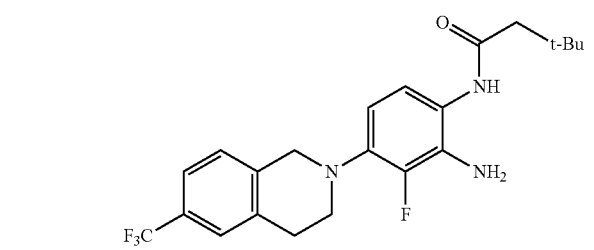

Under nitrogen, to tert-butyl N-tert-butoxycarbonyl-N-[6-(3,3-dimethylbutanoylamino)-2-fluoro-3-[6-(trifluoromethyl)-3,4-dihydro-1H-isoquinolin-2-yl]phenyl]carbamate (1.25 g, 2.00 mmol, 1.00 equiv) in DCM (5 mL) at 23° C. was added HCl (2.0 M in Et₂O, 10.0 mL, 20.0 mmol, 10.0 equiv). After stirring for 15 hr at 23° C., NaHCO₃ (aq) (10 mL) was added to the reaction mixture. The phases were separated and the aqueous phase was extracted with EtOAc (2×10 mL). The combined organic phases were washed with brine (10 mL) and dried (MgSO₄). The filtrate was concentrated in vacuo to afford 570 mg of the title compound (67% yield).

NMR Spectroscopy: $^1$H NMR (300 MHz, methanol-d4, 23° C., δ): 7.42-7.25 (m, 3H), 6.75 (d, J=8.7 Hz, 1H), 6.41 (dd, J=8.7, 8.7 Hz, 1H), 4.23 (s, 2H), 3.36 (t, J=6.0 Hz, 2H), 2.96 (t, J=6.0 Hz, 2H), 2.21 (s, 2H), 1.04 (s, 9H).

Example 32: Compound 34

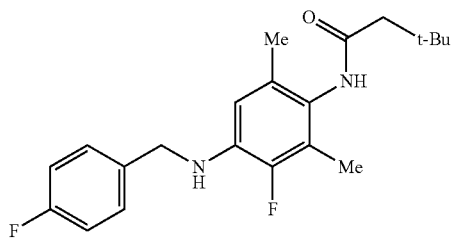 [SMILES: Cc1cc(NCc2ccc(F)cc2)c(F)c(C)c1NC(=O)CC(C)(C)C]

Step 1: Synthesis of 1-Fluoro-2,4-dimethyl-3-nitrobenzene

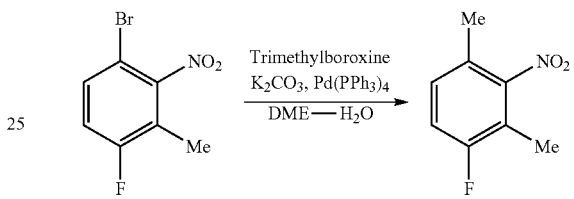

Under air, to 1-bromo-4-fluoro-3-methyl-2-nitro-benzene (4.68 g, 20.0 mmol, 1.00 equiv) in DME-H₂O (10 mL-10 mL) at 23° C. were added trimethylboroxine (1.76 g, 14.0 mmol, 0.700 equiv), K₂CO₃ (4.15 g, 30.0 mmol, 1.50 equiv), and Pd(PPh₃)₄ (2.31 g, 2.00 mmol, 10.0 mol %). After stirring for 3 d at 100° C., the reaction mixture was cooled to 23° C. The phases were separated and the aqueous phase was extracted with EtOAc (2×10 mL). The combined organic phases were washed with brine (10 mL) and dried (MgSO₄). The filtrate was concentrated in vacuo and the residue was purified by column chromatography on silica gel eluting with hexanes/EtOAc to afford 3.00 g of the title compound (89% yield).

NMR Spectroscopy: $^1$H NMR (300 MHz, CDCl₃, 23° C., δ): 7.05-6.99 (m, 2H), 2.21 (s, 3H), 2.15 (d, J=1.8 Hz, 3H).

Step 2: Synthesis of 3-Fluoro-2,6-dimethylaniline

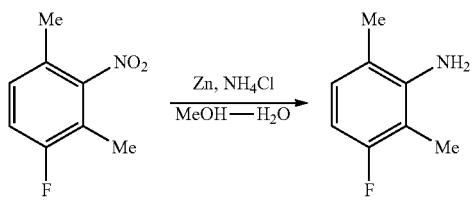

Under air, to 1-fluoro-2,4-dimethyl-3-nitrobenzene (3.00 g, 17.7 mmol, 1.00 equiv) in MeOH (177 mL) at 23° C. were added Zn powder (5.80 g, 88.7 mmol, 5.00 equiv) and NH₄Cl (4.74 g, 5.00 mmol, 5.00 equiv) in H₂O (10 mL). After stirring for 3 hr at 23° C., the reaction mixture was filtered through a pad of celite. The filtrate was concentrated in vacuo, and H₂O (100 mL) and EtOAc (100 mL) were added to the residue. The phases were separated and the aqueous phase was extracted with EtOAc (2×100 mL). The combined organic phases were washed with brine (200 mL) and dried (MgSO$_4$). The filtrate was concentrated in vacuo and the residue was purified by column chromatography on silica gel eluting with hexanes/EtOAc to afford 2.00 g of the title compound (81% yield).

NMR Spectroscopy: $^1$H NMR (300 MHz, CDCl$_3$, 23° C., δ): 6.87 (dd, J=7.5, 7.5 Hz, 1H), 6.48 (dd, J=9.0, 7.5 Hz, 1H), 2.19 (s, 3H), 2.14 (d, J=1.8 Hz, 3H).

Step 3: Synthesis of
4-Bromo-3-fluoro-2,6-dimethylaniline

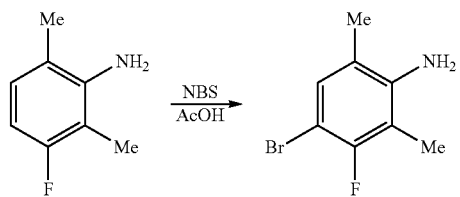

Under air, to 3-fluoro-2,6-dimethylaniline (2.00g, 14.4 mmol, 1.00 equiv) in AcOH (14 mL) at 23° C. was added NBS (2.56 g, 14.4 mmol, 1.00 equiv). After stirring for 10 min at 23° C., the reaction mixture was poured into water (100 mL). Potassium carbonate was added to neutralize the solution, after which was extracted with EtOAc (2×100 mL). The combined organic phases were washed with brine (200 mL) and dried (MgSO$_4$). The filtrate was concentrated in vacuo and the residue was purified by column chromatography on silica gel eluting with hexanes/EtOAc to afford 1.66 g of the title compound (53% yield).

NMR Spectroscopy: $^1$H NMR (300 MHz, CDCl$_3$, 23° C., δ): 7.07 (d, J=4.5 Hz, 1H), 2.14 (s, 6H).

Step 4: Synthesis of ethyl
(4-bromo-3-fluoro-2,6-dimethylphenyl)carbamate

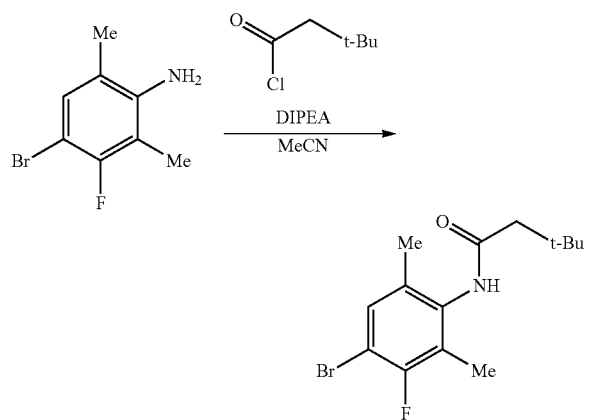

Under nitrogen, to 4-bromo-3-fluoro-2,6-dimethylaniline (830 mg, 3.81 mmol, 1.00 equiv) in MeCN (3.8 mL) at 0° C. were added DIPEA (797 μl, 5.72 mmol, 1.50 equiv) and ethyl chloroformate (798 μl, 5.72 mmol, 1.50 equiv). After stirring for 4 hr at 23° C., NaHCO$_3$ (aq) (10 mL) was added to the reaction mixture. The phases were separated and the aqueous phase was extracted with EtOAc (2×10 mL). The combined organic phases were washed with brine (10 mL) and dried (MgSO$_4$). The filtrate was concentrated in vacuo and the residue was purified by column chromatography on silica gel eluting with hexanes/EtOAc to afford 935 mg of the title compound (78% yield).

NMR Spectroscopy: $^1$H NMR (300 MHz, CDCl$_3$, 23° C., δ): 7.26 (d, J=4.5 Hz, 1H), 6.65 (br s, 1H), 2.18 (s, 2H), 2.14 (s, 6H), 1.14 (s, 9H).

Step 5: Synthesis of N-(3-fluoro-4-((4-fluorobenzyl)
amino)-2,6-dimethylphenyl)-3,3-dimethylbutana-
mide (Compound 34)

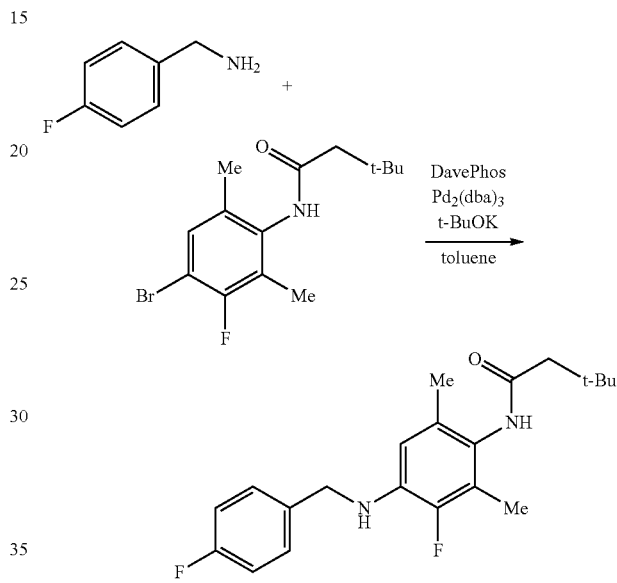

Under nitrogen, to N-(4-bromo-3-fluoro-2,6-dimethyl-phenyl)-3,3-dimethyl-butanamide (316 mg, 1.00 mmol, 1.00 equiv) in toluene (5 mL) at 23° C. are added 4-fluorobenzylamine (125 mg, 1.00 mmol, 1.00 equiv), DavePhos (47 mg, 0.12 mmol, 12 mol %), Pd$_2$(dba)$_3$ (37 mg, 0.040 mmol, 4.0 mol %), and t-BuOK (168 mg, 1.50 mmol, 1.50 equiv). After stirring for 2 hr at 90° C., the reaction mixture is concentrated in vacuo and the residue is purified by column chromatography on silica gel eluting with hexanes/EtOAc to afford the title compound.

Example 33: Compound 35

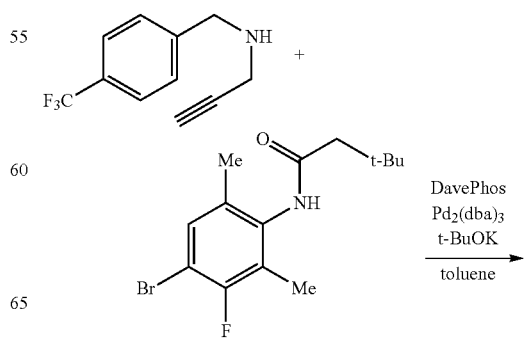

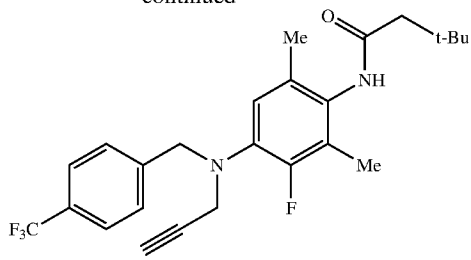

Under nitrogen, to N-(4-bromo-3-fluoro-2,6-dimethylphenyl)-3,3-dimethyl-butanamide (316 mg, 1.00 mmol, 1.00 equiv) in toluene (5 mL) at 23° C. were added N-[[4-(trifluoromethyl)phenyl]methyl]prop-2-yn-1-amine (235 mg, 1.10 mmol, 1.10 equiv), DavePhos (47 mg, 0.12 mmol, 12 mol %), Pd$_2$(dba)$_3$ (37 mg, 0.040 mmol, 4.0 mol %), and t-BuOK (168 mg, 1.50 mmol, 1.50 equiv). After stirring for 2 d at 110° C., the reaction mixture was concentrated in vacuo and the residue was purified by column chromatography on silica gel eluting with hexanes/EtOAc to afford 120 mg the title compound (27% yield).

NMR Spectroscopy: $^1$H NMR (300 MHz, CDCl$_3$, 23° C., δ): 7.57 (d, J=8.7 Hz, 2H), 7.50 (d, J=8.7 Hz, 2H), 7.08 (d, J=7.5 Hz, 1H), 6.96 (br s, 1H), 4.00 (s, 2H), 3.65 (s, 2H), 2.27 (s, 1H), 2.13-2.10 (m, 8H), 1.12 (s, 9H).

Example 34: Compound 36

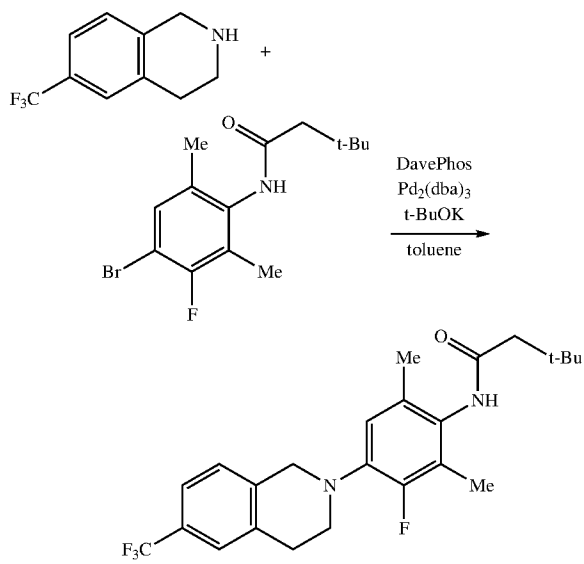

Under nitrogen, to N-(4-bromo-3-fluoro-2,6-dimethylphenyl)-3,3-dimethyl-butanamide (158 mg, 0.500 mmol, 1.00 equiv) in toluene (2.5 mL) at 23° C. were added 6-(trifluoromethyl)-1,2,3,4-tetrahydroisoquinoline hydrochloric acid salt (178 mg, 0.750 mmol, 1.50 equiv), DavePhos (47 mg, 0.12 mmol, 24 mol %), Pd$_2$(dba)$_3$ (37 mg, 0.040 mmol, 8.0 mol %), and t-BuOK (168 mg, 1.50 mmol, 3.00 equiv). After stirring for 1 hr at 100° C., the reaction mixture was concentrated in vacuo and the residue was purified by column chromatography on silica gel eluting with hexanes/EtOAc to afford 72 mg the title compound (33% yield).

NMR Spectroscopy: $^1$H NMR (300 MHz, CDCl$_3$, 23° C., δ): 7.40-7.32 (m, 2H), 7.14 (d, J=8.7 Hz, 1H), 6.79-6.70 (m, 1H), 6.54 (br s, 1H), 4.25 (br s, 2H), 3.37 (t, J=6.0 Hz, 2H), 3.03 (t, J=6.0 Hz, 2H), 2.23 (s, 2H), 2.13-2.08 (m, 6H), 1.08 (s, 9H).

Example 35: Assessment of KCNQ2/3 Channel Activation Activity

The in vitro effects of a compound of the application on cloned KCNQ2/3 potassium channels (encoded by the human KCNQ2/3 gene and expressed in HEK293 cells) are evaluated at room temperature using the QPatch HT® (Sophion Bioscience A/S, Denmark), an automatic parallel patch clamp system. Each test compound is evaluated at 0.01, 0.1, 1, 10 and 100 μM with each concentration tested in at least two cells (n≥2). The duration of exposure to each test compound concentration is 5 minutes.

The baseline for each recording is established using a 5-10 minute vehicle application (HBPS+0.3% DMSO). A single test compound concentration is applied for a period of 5 minutes after the vehicle, followed by a 3 minute application of 30 μM flupirtine. Each recording ends with a supramaximal dose of 30 μM linopirdine. The % activation is calculated using the following equation by using leak subtracted responses:

$$\frac{\text{vehicle\_response} - \text{compound\_response}}{\text{vehicle\_response} - \text{flupirtine\_response}}$$

Example 36: Electrophysiology (Kalappa et al., J. Neurosci., 35, 8829 (2015))

HEK293T cells are transfected with recombinant DNA (3-5 μg) using Lipofectamine 2000 (Invitrogen, Carlsbad, Calif.) and recorded 48 hours after transfection. All experiments are performed at room temperature using conventional whole-cell patch clamp technique. Recording electrodes are filled with internal solution containing (in mM): 132 K-Gluconate, 10 KCl, 4 Mg·ATP, 20 HEPES, and 1 EGTA·KOH, pH 7.2-7.3, and have resistances of 3-5 MΩ. The standard bath solution contains (in mM): 144 NaCl, 2.5 KCl, 2.25 CaCl$_2$, 1.2 MgCl$_2$, 10 HEPES, and 22 D-Glucose, pH 7.2-7.3. Series resistance is compensated by 75%. Osmolarity is adjusted to 300-305 mOsm and pH to 7.2-7.3 with NaOH. Voltage pulses are applied at 30s intervals from a holding potential of −85 mV to various test pulses before jumping down to −70 mV. These values are adjusted for the calculated junction potential of −15 mV. Data are acquired through a Multiclamp 700B amplifier (Molecular Devices, Sunnyvale, Calif.), low-pass filtered at 2 kHz and sampled at 10 kHz. The construct for testing KCNQ2/3 electrophysiology is created as described previously (Soh and Tzingounis, Mol. Pharmaco., 78, 1088 (2010)).

Example 37: Maximal Electroshock Seizure Test (MES)

In MES test, the ability of different doses of the test compound in preventing seizure induced by an electrical stimulus of 0.2 s in duration (50 mA at 60 Hz), delivered through the corneal electrodes primed with a drop of anesthetic/electrolyte solution (0.5% tetracaine hydrochloride in 0.9% saline) is tested. Mice are restrained by hand and released immediately following corneal stimulation that allows for the observation of the entire seizure episode. A maximal seizure in a test animal includes four distinct phases that includes, hind leg flexor component tonic phase (Phase I), hind leg extensor component of the tonic phase (Phase II), intermittent, whole-body clonus (Phase III), and muscular relaxation (Phase IV) followed by seizure termination (Woodbury & Davenport, 1952; Racine et al., 1972). Test compounds are tested for their ability to abolish hind limb tonic extensor component that indicates the compound's ability to inhibit MES-induced seizure spread. Compounds are pre-administered (i.p) and tested at 0.25, 0.5, 1 and 4 h time points for the abolishment of hind limb tonic extensor component after electrical stimulus.

Example 38: Corneal-Kindled Mouse Model of Partial Seizures

In corneal kindled seizure model, mice are kindled electrically with 3 s stimulation, 8 mA, 60 Hz delivered through corneal electrodes primed with 0.5% tetracaine hydrochloride in 0.9% saline, twice daily, until 5 consecutive stage V seizures are induced. Mice are considered kindled when they display at least 5 consecutive stage V seizures according to the Racine scale (Racine et al., 1972) including, mouth and facial clonus (stage I), Stage I plus head nodding (Stage II), Stage II plus forelimb clonus (Stage III), Stage III plus rearing (Stage IV), and stage IV plus repeated rearing and falling (Stage V) (Racine et al., 1972). At the completion of the kindling acquisition, mice are permitted a 3-day stimulation-free period prior to any drug testing. On the day of the experiment, fully kindled mice are pre-administered (i.p) with increasing doses of the test compound and challenged with the corneal kindling stimulus of 3 mA for 3 seconds 15 min. Mice are scored as protected (seizure score of <3) or not protected, (seizure score ≥4) based on the Racine scoring (Racine et al., 1972).

Example 39: Assessment of Recombinantly Expressed Human Kv7.2/7.3 Xhannels Activation Ability The in vitro effects of a compound of the present application recombinantly expressed human Kv7.2/7.3 channels are assessed on Syncropatch high throughput electrophysiology platform.

Cell Preparations: CHO cells stably expressing human Kv7.2/7.3 channels were cultured in Ham's F-12 media (Hyclone, Cat #SH30022.02) supplemented with 10% Fetal Bovine Serum, 1×MEM non-essential amino acids, and 400m/ml G418 at 37° C. in 5% $CO_2$. On the day of Syncropatch, the cells were washed once in DPBS (Hyclone, Cat #SH30028.03) for approximately 30 seconds. 1 ml of 1×0.015% Trypsin-EDTA GIBCO Cat #25300-054) was added and swirled around to cover the bottom of the flask, and allowed to sit on the cells for about 4 minutes (approximately 90% of the cells were lifted by light tapping of the flask). 10 ml of cold media (Ham's F-12 media (Hyclone, Cat #SH30022.02) supplemented with 10% Fetal Bovine Serum, 1×MEM non-essential amino acids, and 400m/ml G418) was added to inactivate Trypsin. The cells were then triturated until a single cell suspension was achieved, and the cell count was performed. The cells were then diluted to a concentration of $5×10^5$/ml and placed into the "cell hotel" on the deck of the Syncropatch at 10° C. for about 1 hour to recover. 40 µL of the cell suspension was dispensed into each well of a 384-well Syncropatch chip by the onboard pipettor at the beginning of each Syncropatch assay.

Test Solution Preparations: The compounds to be tested were dissolved in DMSO to give 10 mM stock solutions. Eight-point dose response curves were created by performing semi-log serial dilutions from 10 mM compound stock solutions in 100% DMSO. Concentration-response curves were transferred to assay plates to give two-fold final compound concentration to account for the two-fold dilution with drug addition on the SyncroPatch. Final DMSO concentration in the assay was 0.3%. Final assay test concentrations were 30 µM to 0.01 µM or 1 µM to 0.0003 µM. Negative (0.3% DMSO) and positive (30 µM ML213) controls were included in each test run to assess pharmacological responsiveness.

Assessment Protocol: Electrophysiological studies of the compounds were performed using the Nanion SyncroPatch automated patch clamp platform. Compound effects on Kv7 channels were assayed using a voltage protocol as shown in FIG. 1.

Kv7 channels were evaluated using a voltage protocol in which cells were voltage-clamped at a holding potential of −110 mV. Potassium currents were activated with a series of voltage steps from −110 mV to +50 mV in 10 mV intervals with 5.5 seconds between successive voltage steps. Each voltage step was 3 seconds in duration and immediately followed by a 1 second voltage step to −120 mV to generate an inward "tail" current to allow construction of activation (G-V) curves by plotting normalized peak tail current versus the potential of the activating voltage step. To obtain normalized values, peak current amplitudes for successive depolarizing pulses were normalized against the maximum tail current amplitude generated at +50 mV (Tatulian et al., Journal of Neuroscience 2001, 21 (15)).

Data Analysis: Data was collected on the Syncropatch platform using PatchControl software (Nanion) and processed and analyzed using DataControl Software (Nanion). Normalized percent activation was calculated and activation curves were fit with a Boltzmann function to determine the midpoint voltage of activation (G-V midpoint) for both pre-compound and post-compound conditions for each of the 384-wells of a sealchip with Pipeline Pilot (Accelrys). The difference in G-V midpoint between pre-compound and post-compound conditions (A V0.5) was plotted as a function of concentration and concentration-response curves were fit with a three-parameter logistic equation {Y=Bottom+(Top−Bottom)/(1+10^(Log EC50−X))} for determination of the $EC_{50}$ (Graphpad Prism).

Assessment Results: Exemplary compounds of the present application were tested for their ability to produce a concentration-dependent hyperpolarizing shift in the midpoint of activation for heteromeric Kv7.2/7.3 channels. Eight of the compounds produced a quantifiable hyperpolarizing shift in activation as determined by a concentration-dependent shift in the midpoint that could be fit with a 3-parameter logistic equation. These data were combined with the initial 8-point concentration-response data in a single fit. Potency and efficacy data for each compound are summarized in Table 2 and FIGS. 2A-2F.

TABLE 2

| Cmpd # | $EC_{50}$ (95% CI) | Cmpd # | $EC_{50}$ (95% CI) |
|---|---|---|---|
| 1 | B | 2 | A |
| 3 | C | 4 | A |
| 6 | A | 7 | A |
| 8 | A | 9 | A |
| 10 (control) | B | 11 | A |

TABLE 2-continued

| Cmpd # | EC$_{50}$ (95% CI) | Cmpd # | EC$_{50}$ (95% CI) |
|---|---|---|---|
| 12 | A | 17 | A |
| 18 | A | 19 | B |
| 20 | A | 21 | B |
| 22 | A | 23 | B |
| 24 | B | X (control) | A |

A: 0.1 to 1.0 μM,
B: 1.0 to 5 μM,
C: 5 to 25 μM,
D: 25 to 50 μM

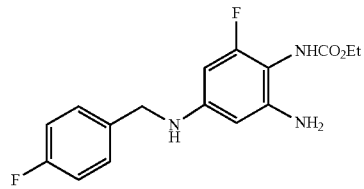

Compound X

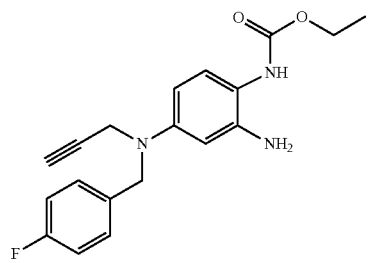

Compound 10

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound that is one of the following compounds set forth in Table 1A, Table 1B, or a pharmaceutically acceptable salt thereof:

TABLE 1A

| Cpd No. | Structure |
|---|---|
| 1 | |
| 2 | 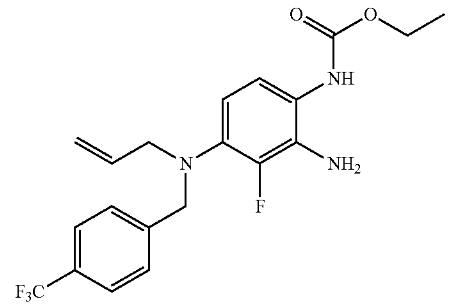 |
| 3 | 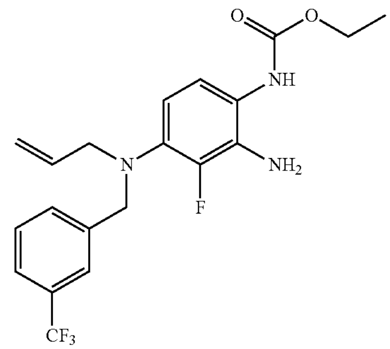 [SMILES: C=CCN(Cc1cccc(C(F)(F)F)c1)c1ccc(NC(=O)OCC)c(N)c1F] |
| 5 | 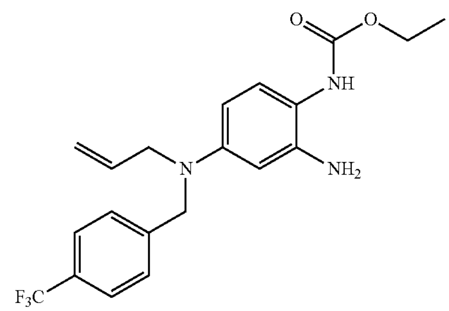 |
| 6 | 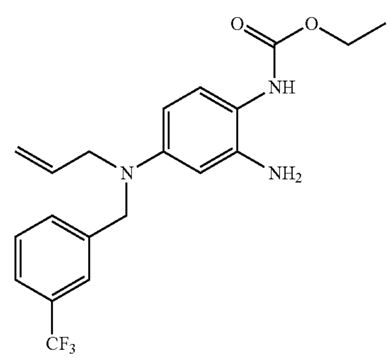 [SMILES: C=CCN(Cc1cccc(C(F)(F)F)c1)c1ccc(NC(=O)OCC)c(N)c1] |

TABLE 1A-continued
| Cpd No. | Structure |
|---|---|
| 7 | 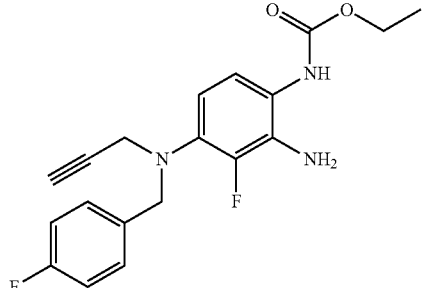 |
| 8 | 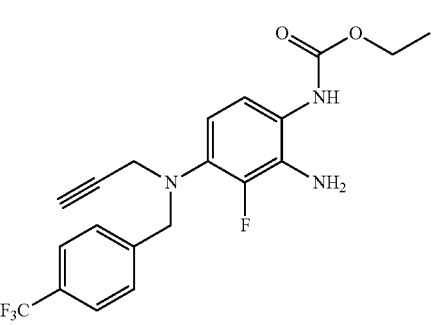 [SMILES: C#CCN(Cc1ccc(C(F)(F)F)cc1)c1ccc(NC(=O)OCC)c(N)c1F] |
| 9 | 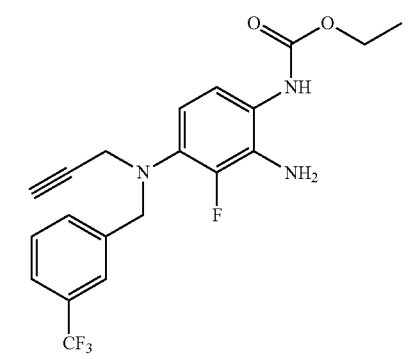 [SMILES: C#CCN(Cc1cccc(C(F)(F)F)c1)c1ccc(NC(=O)OCC)c(N)c1F] |
| 11 | 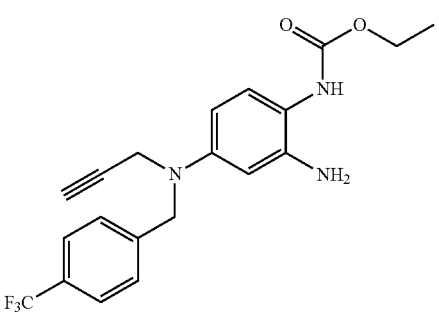 [SMILES: C#CCN(Cc1ccc(C(F)(F)F)cc1)c1ccc(NC(=O)OCC)c(N)c1] |
| 12 | 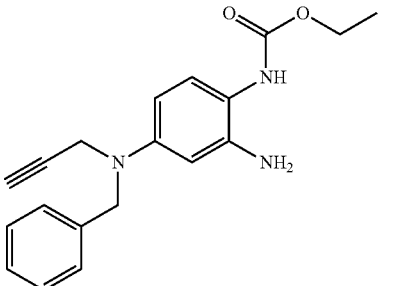 |
| 13 | 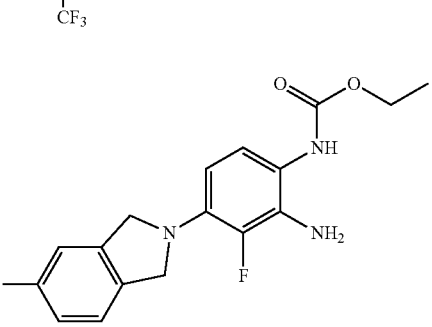 |
| 14 | 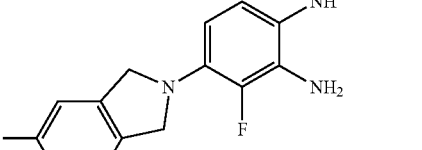 |
| 15 | 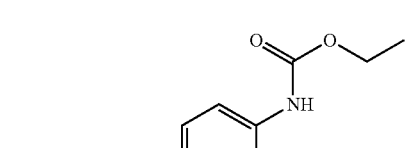 |
| 16 | 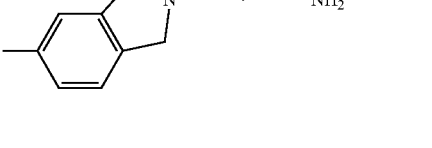 |

TABLE 1A-continued

| Cpd No. | Structure |
|---|---|
| 17 | (6-fluoro-1,2,3,4-tetrahydroisoquinolin-2-yl) attached to phenyl bearing NHC(O)OEt, NH₂, and F substituents |
| 18 | (7-trifluoromethyl-1,2,3,4-tetrahydroisoquinolin-2-yl) attached to phenyl bearing NHC(O)OEt, NH₂, and F substituents |
| 19 | (6-trifluoromethyl-1,2,3,4-tetrahydroisoquinolin-2-yl) attached to phenyl bearing NHC(O)OEt, NH₂, and F substituents |
| 20 | (7-fluoro-1,2,3,4-tetrahydroisoquinolin-2-yl) attached to phenyl bearing NHC(O)OEt, NH₂, and F substituents |
| 21 | (6-fluoro-1,2,3,4-tetrahydroisoquinolin-2-yl) attached to phenyl bearing NHC(O)OEt and NH₂ substituents |
| 22 | (7-trifluoromethyl-1,2,3,4-tetrahydroisoquinolin-2-yl) attached to phenyl bearing NHC(O)OEt and NH₂ substituents |

TABLE 1A-continued

| Cpd No. | Structure |
|---|---|
| 23 | (6-trifluoromethyl-1,2,3,4-tetrahydroisoquinolin-2-yl) attached to phenyl bearing NHC(O)OEt and NH₂ substituents |
| 24 | (7-fluoro-1,2,3,4-tetrahydroisoquinolin-2-yl) attached to phenyl bearing NHC(O)OEt and NH₂ substituents |
| 25 | (6-fluoro-1,2,3,4-tetrahydroisoquinolin-2-yl) attached to 2,6-dimethyl-3-fluorophenyl bearing NHC(O)OEt substituent |
| 26 | N-(4-fluorobenzyl)-N-(prop-2-yn-1-yl)amino group attached to 2,6-dimethyl-3-fluorophenyl bearing NHC(O)OEt substituent |

TABLE 1B

| Cpd No. | Structure |
|---|---|
| 27 | (6-fluoro-1,2,3,4-tetrahydroisoquinolin-2-yl) attached to 2,6-dimethyl-3-fluorophenyl bearing NHC(O)CH₂-t-Bu substituent |

TABLE 1B-continued

| Cpd No. | Structure |
|---|---|
| 28 | *[structure: 4-fluorobenzyl-propargyl-N on aryl with Me, F, Me substituents, NH-C(O)-CH2-t-Bu]* |
| 29 | *[structure: 4-fluorobenzylamino aryl with F, NH2, NH-C(O)-CH2-t-Bu]* |
| 30 | *[structure: 4-fluorobenzyl-propargyl-N aryl with F, NH2, NH-C(O)-CH2-t-Bu]* |
| 31 | *[structure: 4-(trifluoromethyl)benzyl-propargyl-N aryl with F, NH2, NH-C(O)-CH2-t-Bu]* |
| 32 | *[structure: 6-fluoro-tetrahydroisoquinolin-2-yl aryl with F, NH2, NH-C(O)-CH2-t-Bu]* |
| 33 | *[structure: 6-(trifluoromethyl)-tetrahydroisoquinolin-2-yl aryl with F, NH2, NH-C(O)-CH2-t-Bu]* |
| 34 | *[structure: 4-fluorobenzylamino aryl with Me, F, Me, NH-C(O)-CH2-t-Bu]* |
| 35 | *[structure: 4-(trifluoromethyl)benzyl-propargyl-N aryl with Me, F, Me, NH-C(O)-CH2-t-Bu]* |
| 36 | *[structure: 6-(trifluoromethyl)-tetrahydroisoquinolin-2-yl aryl with Me, F, Me, NH-C(O)-CH2-t-Bu]* |

2. The compound of claim 1, wherein the compound is

*[structure: 6-fluoro-tetrahydroisoquinolin-2-yl aryl with F, NH2, NH-C(O)-CH2-t-Bu]* or a pharmaceutically acceptable salt thereof.

3. The compound of claim 1, wherein the compound is

*[structure: 6-fluoro-tetrahydroisoquinolin-2-yl aryl with F, NH2, NH-C(O)-CH2-t-Bu]*.

4. The compound of claim 1, wherein the compound is

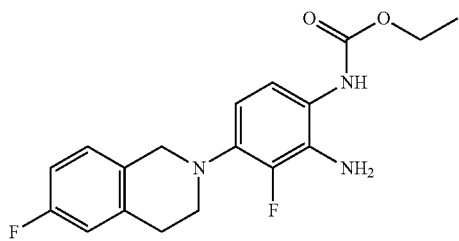 [SMILES: CCOC(=O)Nc1ccc(N2CCc3cc(F)ccc3C2)c(F)c1N]

or a pharmaceutically acceptable salt thereof.

5. The compound of claim 1, wherein the compound is

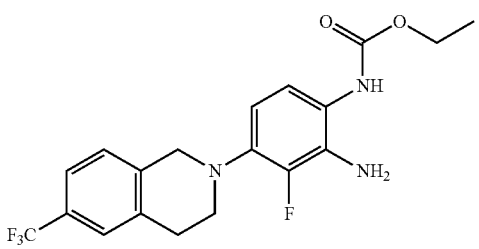 [SMILES: CCOC(=O)Nc1ccc(N2CCc3cc(C(F)(F)F)ccc3C2)c(F)c1N]

or a pharmaceutically acceptable salt thereof.

6. The compound of claim 1, wherein the compound is

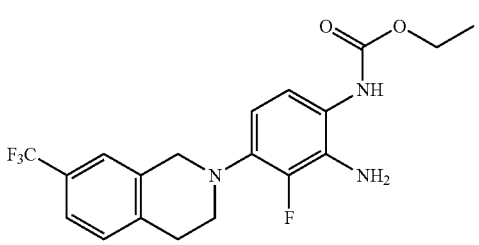 [SMILES: CCOC(=O)Nc1ccc(N2CCc3ccc(C(F)(F)F)cc3C2)c(F)c1N]

or a pharmaceutically acceptable salt thereof.

7. The compound of claim 1, wherein the compound is

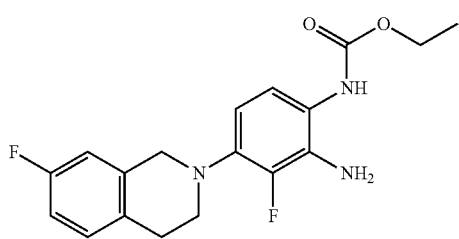 [SMILES: CCOC(=O)Nc1ccc(N2CCc3ccc(F)cc3C2)c(F)c1N]

or a pharmaceutically acceptable salt thereof.

8. The compound of claim 1, wherein the compound is

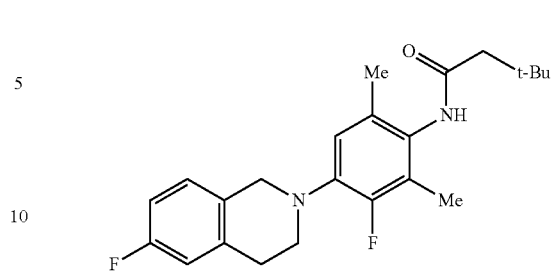

or a pharmaceutically acceptable salt thereof.

9. The compound of claim 1, wherein the compound is

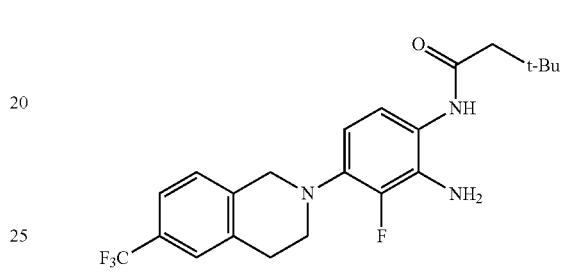

or a pharmaceutically acceptable salt thereof.

10. A pharmaceutical composition comprising a compound according to claim 1 and one or more pharmaceutically acceptable carrier or excipient.

11. A pharmaceutical composition comprising a compound according to claim 2 and one or more pharmaceutically acceptable carrier or excipient.

12. A pharmaceutical composition comprising a compound according to claim 3 and one or more pharmaceutically acceptable carrier or excipient.

13. A method of treating a disease or disorder which can be ameliorated by KCNQ2/3 potassium channel opening, comprising administering to a subject in need thereof a therapeutically effective amount of a compound of claim 1.

14. The method of claim 13, wherein the disease or disorder is epilepsy.

15. A method of treating a disease or disorder which can be ameliorated by KCNQ2/3 potassium channel opening, comprising administering to a subject in need thereof a therapeutically effective amount of a compound of claim 2.

16. The method of claim 15, wherein the disease or disorder is epilepsy.

17. A method of treating a disease or disorder which can be ameliorated by KCNQ2/3 potassium channel opening, comprising administering to a subject in need thereof a therapeutically effective amount of a compound of claim 3.

18. The method of claim 17, wherein the disease or disorder is epilepsy.

* * * * *